(12) United States Patent
Xu et al.

(10) Patent No.: US 8,349,210 B2
(45) Date of Patent: *Jan. 8, 2013

(54) MESOGENIC STABILIZERS

(75) Inventors: Ruisong Xu, Monroeville, PA (US); Xiao-Man Dai, Export, PA (US); Anil Kumar, Murrysville, PA (US); Meng He, Murrysville, PA (US); Chenguang Li, Monroeville, PA (US); Rachael L. Yoest, Gibsonia, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,835

(22) Filed: Aug. 8, 2011

(65) Prior Publication Data

US 2012/0003401 A1 Jan. 5, 2012

Related U.S. Application Data

(63) Continuation-in-part of application No. 13/051,130, filed on Mar. 18, 2011, which is a continuation-in-part of application No. 12/489,811, filed on Jun. 23, 2009, now Pat. No. 7,910,019, and a continuation-in-part of application No. 12/489,843, filed on Jun. 23, 2009, now Pat. No. 7,910,020, which is a continuation-in-part of application No. 12/163,180, filed on Jun. 27, 2008, now abandoned, said application No. 12/489,811 is a continuation-in-part of application No. 12/163,116, filed on Jun. 27, 2008, now abandoned.

(51) Int. Cl.
    *C09K 19/52* (2006.01)
    *C09K 19/06* (2006.01)
    *C09K 19/00* (2006.01)
    *C07D 211/00* (2006.01)
    *C07C 69/76* (2006.01)

(52) U.S. Cl. ............ 252/299.01; 252/299.5; 252/299.6; 252/299.61; 252/299.62; 428/1.1; 428/1.3; 546/188; 546/222; 549/415; 549/416; 560/59; 560/61; 560/81; 349/1; 349/56; 349/182

(58) Field of Classification Search ............ 252/299.01, 252/299.5, 299.6, 299.61, 299.62; 428/1.1, 428/1.3; 546/188, 222; 549/415, 416; 560/59, 560/61, 81; 349/1, 56, 182
See application file for complete search history.

(56) References Cited

U.S. PATENT DOCUMENTS

| | | | |
|---|---|---|---|
| 4,539,048 A | 9/1985 | Cohen | |
| 4,539,049 A | 9/1985 | Cohen | |
| 4,556,605 A | 12/1985 | Mogami et al. | |
| 4,650,526 A | 3/1987 | Claffey et al. | |
| 4,756,973 A | 7/1988 | Sakagami et al. | |
| 4,931,220 A | 6/1990 | Haynes et al. | |
| 5,458,814 A | 10/1995 | Kumar et al. | |
| 5,466,398 A | 11/1995 | Van Gemert et al. | |
| 5,514,817 A | 5/1996 | Knowles | |
| 5,573,712 A | 11/1996 | Kumar et al. | |
| 5,578,252 A | 11/1996 | Van Gemert et al. | |
| 5,637,262 A | 6/1997 | Van Gemert et al. | |
| 5,645,767 A | 7/1997 | Van Gemert | |
| 5,650,098 A | 7/1997 | Kumar et al. | |
| 5,651,923 A | 7/1997 | Kumar et al. | |
| 5,698,141 A | 12/1997 | Kumar | |
| 5,723,072 A | 3/1998 | Kumar | |
| 5,800,733 A | 9/1998 | Kelly | |
| 5,871,665 A | 2/1999 | Coates et al. | |
| 5,891,368 A | 4/1999 | Kumar | |

(Continued)

FOREIGN PATENT DOCUMENTS

GB      2311289 A      9/1997

(Continued)

OTHER PUBLICATIONS

Baron, M. et al., "Definitions of Basic Terms Relating to Polymer Liquid Crystals (IUPAC Recommendations, 2001)", Pure Appl. Chem, 2002, pp. 493-509, 74(3).

Scruggs, N. R., "Conformational Anisotropy of Side-Group Liquid Crystal Polymers in Nematic Liquid Crystal Solvent: Small-Angle Neutron Scattering of Semidilute Solutions", Chapter 5, 2007, pp. 122-142, etd.caltech.edu/etd/available/etd-02202007-131552/unrestricted/5_Chapter.pdf (last visited Aug. 28, 2008).

(Continued)

*Primary Examiner* — Geraldina Visconti
(74) *Attorney, Agent, or Firm* — Deborah M. Altman; Frank P Mallak

(57) ABSTRACT

The present invention relates to compounds represented by the following Formula I,

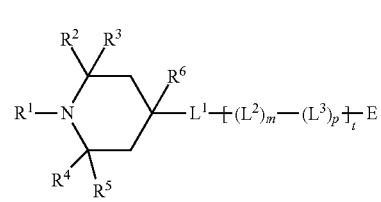

in which $R^1$-$R^6$ can each independently be selected from hydrogen or hydrocarbyl (e.g., methyl); $L^1$ is a divalent linking group, such as a bond or —OC(O)—$R^8$—C(O)O—, where $R^8$ can be divalent hydrocarbyl (e.g., —$CH_2CH_2$—); each $L^2$ independently represents a flexible segment, such as divalent linear or branched $C_1$-$C_{25}$ alkyl; each $L^3$ independently represents a rigid segment including, for example, optionally substituted phenylen-1,4-diyl groups; t is from 1 to 4; m and p are each independently from 0 to 4 for each t, provided that the sum of m and p is at least 1 for each t; and E can be hydrogen or hydrocarbyl. The present invention also relates to compositions, such as liquid crystal compositions, and articles, such as optical elements, that include the compound represented by Formula I.

21 Claims, No Drawings

U.S. PATENT DOCUMENTS

| | | | |
|---|---|---|---|
| 5,962,617 A | 10/1999 | Slagel | |
| 6,022,495 A | 2/2000 | Kumar | |
| 6,022,497 A | 2/2000 | Kumar | |
| 6,025,026 A | 2/2000 | Smith et al. | |
| 6,060,001 A | 5/2000 | Welch et al. | |
| 6,080,338 A | 6/2000 | Kumar | |
| 6,096,375 A | 8/2000 | Ouderkirk et al. | |
| 6,099,752 A | 8/2000 | Hall et al. | |
| 6,106,744 A | 8/2000 | Van Gemert et al. | |
| 6,113,814 A | 9/2000 | Van Gemert et al. | |
| 6,136,968 A | 10/2000 | Chamontin et al. | |
| 6,149,841 A | 11/2000 | Kumar | |
| 6,150,430 A | 11/2000 | Walters et al. | |
| 6,153,126 A | 11/2000 | Kumar | |
| 6,187,444 B1 | 2/2001 | Bowles, III et al. | |
| 6,217,948 B1 | 4/2001 | Verrall et al. | |
| 6,248,264 B1 | 6/2001 | Clarke et al. | |
| 6,268,055 B1 | 7/2001 | Walters et al. | |
| 6,296,785 B1 | 10/2001 | Nelson et al. | |
| 6,338,808 B1 | 1/2002 | Kawata et al. | |
| 6,348,604 B1 | 2/2002 | Nelson et al. | |
| 6,353,102 B1 | 3/2002 | Kumar | |
| 6,432,544 B1 | 8/2002 | Stewart et al. | |
| 6,433,043 B1 | 8/2002 | Misura et al. | |
| 6,436,525 B1 | 8/2002 | Welch et al. | |
| 6,459,847 B1 | 10/2002 | Van De Witte et al. | |
| 6,506,488 B1 | 1/2003 | Stewart et al. | |
| 6,531,076 B2 | 3/2003 | Crano et al. | |
| 6,555,028 B2 | 4/2003 | Walters et al. | |
| 6,597,856 B2 | 7/2003 | Van De Witte et al. | |
| 6,602,603 B2 | 8/2003 | Welch et al. | |
| 6,630,597 B1 | 10/2003 | Lin et al. | |
| 6,641,874 B2 | 11/2003 | Kuntz et al. | |
| 6,660,344 B2 | 12/2003 | Lub | |
| 6,713,536 B2 | 3/2004 | Misura et al. | |
| 6,733,689 B1 | 5/2004 | Meyer et al. | |
| 6,733,690 B1 | 5/2004 | Lukac et al. | |
| 6,736,998 B2 | 5/2004 | Petrovskaia et al. | |
| 6,773,626 B2 | 8/2004 | Sanada et al. | |
| 6,875,483 B2 | 4/2005 | Ichihashi et al. | |
| 6,941,051 B2 | 9/2005 | Xu et al. | |
| 6,958,176 B2 | 10/2005 | Li et al. | |
| 7,029,728 B2 | 4/2006 | Dunn et al. | |
| 7,058,249 B2 | 6/2006 | Purchase et al. | |
| 7,094,368 B2 | 8/2006 | Kim et al. | |
| 7,097,303 B2 | 8/2006 | Kumar et al. | |
| 7,098,359 B2 | 8/2006 | Wellinghoff et al. | |
| 7,169,448 B2 | 1/2007 | Coates et al. | |
| RE39,605 E | 5/2007 | Verrall et | |
| 7,238,831 B2 | 7/2007 | Wellinghoff et al. | |
| 7,256,921 B2 | 8/2007 | Kumar et al. | |
| 7,262,295 B2 | 8/2007 | Walters et al. | |
| 7,282,551 B2 | 10/2007 | Hoff et al. | |
| 7,320,826 B2 | 1/2008 | Kumar et al. | |
| 7,342,112 B2 | 3/2008 | Kumar et al. | |
| 7,410,691 B2 | 8/2008 | Blackburn et al. | |
| 7,481,955 B2 | 1/2009 | Xiao | |
| 7,505,189 B2 * | 3/2009 | Kumar et al. | 359/241 |
| 7,618,690 B2 | 11/2009 | Nagayama et al. | |
| 7,632,540 B2 | 12/2009 | Kumar et al. | |
| 7,632,906 B2 | 12/2009 | Studer et al. | |
| 7,910,019 B2 * | 3/2011 | He et al. | 252/299.01 |
| 7,910,020 B2 * | 3/2011 | He et al. | 252/299.01 |
| 2002/0039627 A1 | 4/2002 | Ichihashi et al. | |
| 2002/0191945 A1 | 12/2002 | Van De Witte et al. | |
| 2003/0045612 A1 | 3/2003 | Misura et al. | |
| 2004/0207809 A1 | 10/2004 | Blackburn et al. | |
| 2005/0003107 A1 | 1/2005 | Kumar et al. | |
| 2005/0004361 A1 | 1/2005 | Kumar et al. | |
| 2005/0012998 A1 | 1/2005 | Kumar et al. | |
| 2005/0040364 A1 | 2/2005 | Cherkaoui et al. | |
| 2006/0049381 A1 | 3/2006 | Klein et al. | |
| 2007/0278460 A1 | 12/2007 | Xiao | |
| 2008/0081133 A1 | 4/2008 | Kato | |
| 2009/0146104 A1 | 6/2009 | He et al. | |
| 2009/0247782 A1 | 10/2009 | Irisawa et al. | |
| 2009/0309076 A1 | 12/2009 | He et al. | |
| 2011/0129678 A1 | 6/2011 | He et al. | |
| 2011/0140056 A1 | 6/2011 | He et al. | |
| 2011/0143141 A1 | 6/2011 | He et al. | |
| 2011/0216273 A1 * | 9/2011 | He et al. | 349/96 |

FOREIGN PATENT DOCUMENTS

| | | |
|---|---|---|
| JP | 55023169 A | 2/1980 |
| WO | 0102449 A2 | 1/2001 |
| WO | 0248282 A1 | 6/2002 |
| WO | 2006003435 A1 | 1/2006 |
| WO | 2008091090 A1 | 7/2008 |

OTHER PUBLICATIONS

Kirk-Othmer, "Kirk-Othmer Encyclopedia of Chemical Technology", 4th ed., 1997, pp. 322-325, vol. 6.

Lewis, R.J., "Hawley's Condensed Chemical Dictionary", 13th ed., John Wiley & Sons, New York 1997, pp. 901-902.

Dieterich, D. et al., "Structure-Property-Relationship in Polyurethanes", 2nd ed., Oertel, G., ed., Polyurethane Handbook, 1994, pp. 37-53, Hanser Publishers.

"Photochromism", Techniques in Chemistry, 1971, vol. III, John Wiley & Sons, New York.

Ullmann's Encyclopedia of Industrial Chemistry, 5th Ed., 1992, pp. 665-716, vol. A21.

* cited by examiner

MESOGENIC STABILIZERS

CROSS REFERENCE TO RELATED APPLICATIONS

This application is entitled to and claims priority to the following United States Patent Applications as a continuation-in-part under 35 U.S.C. §120: U.S. patent application Ser. No. 13/051,130, filed on Mar. 18, 2011; U.S. patent application Ser. No. 12/489,811, filed Jun. 23, 2009; U.S. patent application Ser. No. 12/489,843, filed Jun. 23, 2009; U.S. patent application Ser. No. 12/163,116, filed Jun. 27, 2008; and U.S. patent application Ser. No. 12/163,180, filed Jun. 27, 2008, each of which is incorporated herein by reference in its entirety.

FIELD OF THE INVENTION

The present invention relates to compounds having one or more stabilizer groups, such as hindered amine light stabilizer groups, and one or more mesogen groups or segments, and to compositions, such as liquid crystal compositions, and articles of manufacture, such as optical elements, containing such compounds.

BACKGROUND OF THE INVENTION

The molecules of a liquid crystal tend to align with one another in substantially one direction, which results in a fluid material having anisotropic optical, electromagnetic, and mechanical properties. A mesogen is typically described as the primary or fundamental unit (or segment or group) of a liquid crystal material that induces, and/or is induced into, structural order amongst and between liquid crystals (e.g., other liquid crystal materials that are present).

Liquid crystal polymers are polymers capable of forming regions of highly ordered structure while in a liquid phase. Liquid crystal polymers have a wide range of uses, including engineering plastics, and gels for LC displays. The structure of liquid crystal polymers is typically composed of densely packed fibrous polymer chains that provide self-reinforcement almost to the melting point of the polymer.

Dichroism can occur in liquid crystals due to the optical anisotropy of the molecular structure, or the presence of impurities, or the presence of dichroic dyes. As used herein, the term "dichroism," and similar terms, such as "dichroic" means the ability to absorb one of two orthogonal plane polarized components of radiation (e.g., transmitted and/or reflected radiation) more strongly than the other orthogonal plane polarized component.

Linearly polarizing elements, such as linearly polarizing lenses for sunglasses and linearly polarizing filters, are typically formed from orientated, such as unilaterally orientated, polymer sheets containing a dichroic material, such as a static dichroic dye. Consequently, conventional linearly polarizing elements are static elements having a single, linearly polarizing state. Accordingly, when a conventional linearly polarizing element is exposed to either randomly polarized radiation or reflected radiation of the appropriate wavelength, some percentage of the radiation transmitted through the element is linearly polarized. As used herein the term "linearly polarized" means to confine or effectively limit the vibrations of the electromagnetic vector of light waves to one direction or plane.

In addition, conventional linearly polarizing elements are often tinted. For example, conventional linearly polarizing elements can contain a coloring agent, such as a static dichroic dye, and correspondingly have an absorption spectrum that does not vary in response to actinic radiation. The color of conventional linearly polarizing elements typically depends upon the coloring agent present in the element, and is often a neutral color (e.g., brown or gray). As such, while conventional linearly polarizing elements are useful in reducing glare associated with reflected light, they are not, however, well suited for use under certain low-light conditions, because of the static coloring agent. In addition, because conventional linearly polarizing elements have only a single, tinted linearly polarizing state, they are limited in their ability to store or display information.

As discussed above, conventional linearly polarizing elements are typically formed using sheets of orientated polymer films containing a dichroic material. Thus, while dichroic materials are capable of selectively absorbing one of two orthogonal plane polarized components of transmitted radiation, if the molecules of the dichroic material are not suitably positioned or aligned, no net linear polarization of transmitted radiation will be achieved. Due to the random positioning of the molecules of the dichroic material, selective absorption by the individual molecules will cancel each other such that no net or overall linear polarizing effect is achieved. As such, suitable positioning of the molecules of the dichroic material is typically achieved by alignment thereof with another material, which results in a net linear polarization.

In contrast to the dichroic elements discussed above, conventional photochromic elements, such as photochromic lenses that are formed using conventional thermally reversible photochromic materials, are generally capable of converting from a first state, for example, a "clear state," to a second state, for example, a "colored state," in response to exposure to actinic radiation, and then reverting back to the first state in response to, actinic radiation, such as the absence or reduction of exposure to actinic radiation, and/or thermal energy. As such, conventional photochromic elements are generally well suited for use in both low-light conditions and bright conditions. Conventional photochromic elements, however, that do not include linearly polarizing filters are generally not adapted to linearly polarize radiation. That is, the absorption ratio of conventional photochromic elements, in either state (e.g., clear state and/or colored state), is generally less than two. As used herein, the term "absorption ratio" refers to the ratio of absorbance of radiation linearly polarized in a first plane to the absorbance of the same wavelength radiation linearly polarized in a plane orthogonal to the first plane, in which the first plane is defined as the plane with the highest absorbance. Therefore, conventional photochromic elements are not capable of reducing glare associated with reflected light to the same extent as conventional linearly polarizing elements. To address this deficiency, photochromic-dichroic materials have been developed. Photochromic-dichroic materials provide both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

Photochromic materials and photochromic-dichroic materials can be incorporated into a substrate or an organic material, for example a polymer substrate, including liquid crystal polymer substrates. When photochromic materials and photochromic-dichroic materials undergo a change from one state to another (e.g., from a clear state to a colored state), the molecule(s) of the photochromic compound or photochromic-dichroic compound typically undergo a conformational change from a first conformational state to a second conformational state. This conformational change can result in a change in the amount of physical space that the compound occupies. For certain photochromic materials and certain photochromic-dichroic materials, however, to effectively transition from one state to another state (e.g., to transition from a clear state to a colored state, or to transition from a colored state to a clear state, and/or to transition from a non-polarized state to a polarized state, or to transition from a polarized state to a non-polarized state) the photochromic compound or photochromic-dichroic compound typically requires a chemical environment that is sufficiently flexible to allow the compound to transition from a first conformational state to a second conformational state at a rate that is at least sufficient to provide the desired response on over an acceptable time frame. Liquid crystal polymers can provide such a sufficiently flexible environment.

Organic materials, such as polymers and/or liquid crystal polymers, typically include stabilizers, such as thermal stabilizers and/or ultraviolet light stabilizers, to limit and/or delay degradation of the organic material due to exposure to elevated temperatures and/or ultraviolet light. The presence of stabilizers in organic materials containing dichroic materials, such as photochromic-dichroic materials, can disrupt alignment of the dichroic materials, resulting in an undesirable reduction in absorption ratio values. Alternatively or additionally, when the organic material is composed of or contains liquid crystal materials, such as liquid crystal polymers, the presence of stabilizers can undesirably disrupt alignment of the liquid crystal materials. Still further alternatively or additionally, to disrupting liquid crystal alignment, the stabilizers may not be sufficiently soluble in the liquid crystal material, such as a liquid crystal polymer matrix, resulting in an undesirable reduction in clarity (e.g., an increase in haze) of the material.

It would be desirable to develop new stabilizers that can be used in compositions containing liquid crystal materials. In addition, it would be desirable that such newly developed stabilizers minimize or result in no disruption of liquid crystal alignment and/or have improved solubility in compositions containing liquid crystal materials. It would be further desirable that such newly developed stabilizers enhance liquid crystal alignment in compositions containing liquid crystal materials.

SUMMARY OF THE INVENTION

In accordance with the present invention, there is provided a compound represented by the following Formula I,

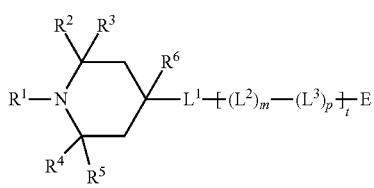

With reference to the compound represented by Formula I, $R^1$ is selected from hydrogen, hydrocarbyl and substituted hydrocarbyl each optionally interrupted with at least one of —O—, —S—, —C(O)—, —C(O)O—, —OC(O)O—, —S(O)—, —SO$_2$—, —N($R^9$)— and —Si($R^9$)($R^{10}$)—, and combinations of two or more thereof. The $R^9$ and $R^{10}$ groups, for example, of the interrupting —N($R^9$)— and —Si($R^9$)($R^{10}$)— groups, are each independently selected from hydrogen, hydrocarbyl and substituted hydrocarbyl.

The $R^2$, $R^3$, $R^4$ and $R^5$ groups of Formula I are each independently selected from hydrocarbyl and substituted hydrocarbyl.

The $R^6$ group of Formula I is selected from hydrogen, OH, hydrocarbyl and substituted hydrocarbyl each optionally interrupted with at least one of —O—, —S—, —C(O)—, —C(O)O—, —OC(O)O—, —S(O)—, —SO$_2$—, —N($R^9$)— and —Si($R^9$)($R^{10}$)— and combinations of two or more thereof. The $R^9$ and $R^{10}$ groups, for example, of the interrupting —N($R^9$)— and —Si($R^9$)($R^{10}$)— groups, are each independently selected from hydrogen, hydrocarbyl and substituted hydrocarbyl.

The $L^1$ linking group of Formula I is a divalent linking group selected from a bond, or one of the following Formulas IIa, IIb, IIc, IId, or IIe,

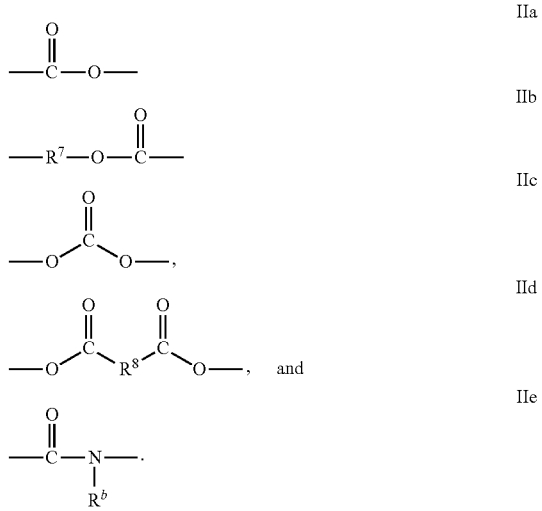

With the divalent linking group represented by Formula IIb, $R^7$ is selected from divalent hydrocarbyl (e.g., hydrocarbylene) and divalent substituted hydrocarbyl (e.g., substituted hydrocarbylene). With the divalent linking group represented by Formula IId, $R^8$ is selected from divalent hydrocarbyl (e.g., hydrocarbylene) and divalent substituted hydrocarbyl (e.g., substituted hydrocarbylene). With the divalent linking group represented by Formula IIe, $R^b$ is selected from hydrogen, hydrocarbyl and substituted hydrocarbyl.

Subscript t of Formula I is 1 to 4. Subscript m of Formula I is, independently for each t, from 0 to 4.

Each $L^2$ of Formula I is, independently for each m, selected from divalent linear or branched $C_1$-$C_{25}$ alkyl (e.g., linear or branched $C_1$-$C_{25}$ alkylene) and divalent linear or branched $C_2$-$C_{25}$ alkenyl (e.g., linear or branched $C_2$-$C_{25}$ alkenylene), in each case optionally interrupted with at least one of —O—, —S—, —C(O)—, —C(O)O—, —OC(O)O—, —S(O)—, —SO$_2$—, —N($R^9$)—, and —Si($R^9$)($R^{10}$)—, and combinations of two or more thereof. The $R^9$ and $R^{10}$ groups, for example, of the interrupting —N($R^9$)— and —Si($R^9$)($R^{10}$)— groups, are each independently selected from hydrogen, hydrocarbyl and substituted hydrocarbyl.

Subscript p of Formula I is, independently for each t, from 0 to 4, provided the sum of m and p is at least 1 for each t.

Each $L^3$ of Formula I is, independently for each p, represented by the following Formula VI,

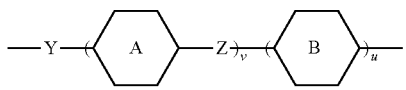

With Formula VI: Y is, independently for each p, a divalent linking group selected from a bond, —O—, and —S—; v and u are each independently, for each p, selected from 0 to 5, provided that the sum of v and u is at least 1 for each p that is greater than zero; and Z is, independently for each v, a divalent linking group selected from a bond, —O—, —S—, —C(O)—, —C(O)O—, —OC(O)O—, —S(O)—, —SO$_2$—, —N(R$^9$)—, —N(R$^9$)—C(O)—O—, —C(O)—N(R$^9$)—, and —Si(R$^9$)(R$^{10}$)— wherein R$^9$ and R$^{10}$ are each independently selected from hydrogen, hydrocarbyl and substituted hydrocarbyl.

The divalent rings of Formula VI,

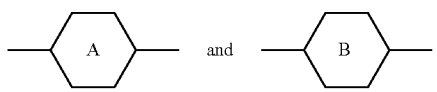

are each independently selected, for each v and each u, respectively, from phenylen-1,4-diyl, or substituted phenylen-1,4-diyl, or cyclohexan-1,4-diyl, or substituted cyclohexan-1,4-diyl, or pyrimidin-2,5-diyl, or substituted pyrimidin-2,5-diyl, or pyridine-2,5-diyl, or substituted pyridine-2,5-diyl, or naphthalene-2,6-diyl, or substituted naphthalene-2,6-diyl, or 1,2,3,4-tetrahydronaphthalene-2,6-diyl, or 1,2,3,4-tetrahydronaphthalene-2,6-diyl in which the aromatic ring is substituted, or decahydronaphthalene-2,6-diyl, or indane-2,5 (6)-diyl, or fluorene-2,-7-diyl, or phenanthrene-2,7-diyl, or 9,10-dihydrophenanthrene-2,7-diyl, or (1,3,4)thiadiazol-2,5-diyl, or (1,3)thiazol-2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl.

With further reference to Formula I, E is selected from hydrogen, hydrocarbyl and substituted hydrocarbyl each optionally interrupted with at least one of —O—, —S—, —C(O)—, —C(O)O—, —OC(O)O—, —S(O)—, —SO$_2$—, —N(R$^9$)—, and —Si(R$^9$)(R$^{10}$)— and combinations of two or more thereof. The R$^9$ and R$^{10}$ groups of the interrupting —N(R$^9$)— and —Si(R$^9$)(R$^{10}$)— groups are each independently selected from hydrogen, hydrocarbyl and substituted hydrocarbyl.

In accordance with some embodiments of the compounds of the present invention, a direct link between any two L groups (such as, between $L^1$ and $L^2$, $L^1$ and $L^3$, and/or $L^2$ and $L^3$) is free of two heteroatoms linked (or bonded) together. In addition, and with some embodiments of the compounds of the present invention, a direct link between E and any L group (such as, between E and $L^1$, E and $L^2$, and/or E and $L^3$) is free of two heteroatoms linked (or bonded) together.

With further reference to Formula I, and in accordance with some embodiments, when $L^1$ is directly linked to $L^2$ (and equivalently, when $L^2$ is directly linked to $L^1$), the direct link therebetween (e.g., a direct $L^1$-$L^2$ link) is free of two heteroatoms linked (or bonded) together. When $L^1$ is directly linked to $L^3$ (and equivalently, when $L^3$ is directly linked to $L^1$), the direct link therebetween (e.g., a direct $L^1$-$L^3$ link) is free of two heteroatoms linked (or bonded) together. For each instance when $L^2$ is directly linked to $L^3$ (and equivalently, when $L^3$ is directly linked to $L^2$), in each case the direct link therebetween (e.g., each direct $L^2$-$L^3$ link) is free of two heteroatoms linked (or bonded) together.

DETAILED DESCRIPTION OF THE INVENTION

As used herein, the term "actinic radiation" means electromagnetic radiation that is capable of causing a response in a material, such as, but not limited to, transforming a photochromic material from one form or state to another form or state, as will be discussed in further detail herein.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "photochromic compound" includes, but is not limited to, thermally reversible photochromic compounds and non-thermally reversible photochromic compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein, the term "photochromic-dichroic" and similar terms, such as "photochromic-dichroic materials" means compounds and materials that possess and/or provide both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

As used herein, the term "photosensitive material" means materials that physically or chemically respond to electromagnetic radiation, including, but not limited to, phosphorescent materials and fluorescent materials.

As used herein, the term "non-photosensitive materials" means materials that do not physically or chemically respond to electromagnetic radiation, including, but not limited to, static dyes.

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species).

As used herein, recitations of "linear or branched" groups, such as linear or branched alkyl, are understood to include: a methylene group or a methyl group; groups that are linear, such as linear $C_2$-$C_{25}$ alkyl groups; and groups that are appropriately branched, such as branched $C_3$-$C_{25}$ alkyl groups.

As used herein, the term "halo" and similar terms, such as halo group, halogen, and halogen group means F, Cl, Br and/or I, such as fluoro, chloro, bromo and/or iodo.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, the term "precursor" and related terms, such as "precursors" with regard to the various groups, for example, groups $R^1$ through $R^6$ of the compounds of the present invention represented by Formula I, and groups of photochromic compounds (e.g., B and B' groups) that can be included in compositions and articles of the present invention, means a group that can be converted in one or more steps to the final or desired group. For purposes of non-limiting illustration: a precursor of a hydroxyl group (—OH) includes, but is not limited to, a carboxylic acid ester group (—OC(O)R where R is hydrogen or an optionally substituted hydrocarbyl); and a precursor of a carboxylic acid ester group (—OC(O)R) includes, but is not limited to, a hydroxyl group (—OH), which can be reacted, for example, with a carboxylic acid halide, such as acetic acid chloride (or acetyl chloride).

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

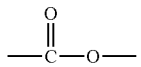

or equivalently —C(O)O—, is inclusive of the right-to-left representation thereof,

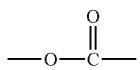

or equivalently —O(O)C— or —OC(O)—.

As used herein, the articles "a," "an," and "the" include plural referents unless otherwise expressly and unequivocally limited to one referent.

Unless otherwise indicated, all U.S. patents and published U.S. patent applications cited herein are incorporated herein by reference in their entirety and/or with regard to those specific portions thereof cited herein.

Other than in the operating examples, or where otherwise indicated, all numbers expressing quantities of ingredients, reaction conditions, and so forth used in the specification and claims are to be understood as modified in all instances by the term "about."

The compounds of the present invention include groups, such as, but not limited to, $R^1$-$R^{10}$, $R^{12}$, and $R^{13}$, that can in each case be independently selected from hydrocarbyl and/or substituted hydrocarbyl. As used herein the term "hydrocarbyl" and similar terms, such as "hydrocarbyl substituent," means: linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{12}$ cycloalkyl (e.g., $C_3$-$C_{10}$ cycloalkyl); $C_5$-$C_{18}$ aryl (including polycyclic aryl groups) (e.g., $C_5$-$C_{10}$ aryl); and $C_6$-$C_{24}$ aralkyl (e.g., $C_6$-$C_{10}$ aralkyl). As used herein the term "hydrocarbyl" is inclusive of "heterohydrocarbyl," which is a hydrocarbyl in which at least one carbon, but less than all of the carbons thereof, has been replaced with a heteroatom, such as, but not limited to, O, N, S, and combinations thereof. Examples of heterohydrocarbyls from which a hydrocarbyl can be selected include, but are not limited to: $C_3$-$C_{12}$ heterocycloalkyl (having at least one hetero atom in the cyclic ring); and $C_5$-$C_{18}$ heteroaryl (having at least one hetero atom in the aromatic ring).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to tetrahydrofuranyl, tetrahydropyranyl and piperidinyl, including but not limited to piperidin-4-yl. Representative aryl groups include but are not limited to phenyl, naphthyl, anthracenyl, phenanthrenyl and triptycenyl. Representative heteroaryl groups include but are not limited to furanyl, pyranyl and pyridinyl. Representative aralkyl groups include but are not limited to benzyl, and phenethyl.

The term "substituted hydrocarbyl" as used herein means a hydrocarbyl group in which at least one hydrogen thereof has been replaced or substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl; heterocycloalkyl, such as piperidinyl, including but not limited to piperidin-4-yl, optionally substituted with, for example, at least one linear or branched $C_1$-$C_{10}$ alkyl group; aryl, including hydroxyl substituted aryl, such as phenol, optionally substituted with, for example, at least one linear or branched $C_1$-$C_{10}$ alkyl group; heteroaryl; and aralkyl groups), and amine groups, such as —N($R_{11}$')($R_{12}$') where $R_{11}$' and $R_{12}$' are each independently selected from hydrogen, hydrocarbyl and substituted hydrocarbyl.

For purposes of non-limiting illustration, the hydrocarbyl, of a substituted hydrocarbyl, can be selected from one or more of the hydrocarbyl groups described previously herein, such as a $C_3$-$C_{12}$ heterocycloalkyl group, such as piperidinyl, which can be substituted with one or more of the substituting groups described previously herein, such as one or more linear or branched $C_1$-$C_{25}$ alkyl groups. For purposes of further non-limiting illustration, the hydrocarbyl, of a substituted hydrocarbyl, can be selected from one or more of the hydrocarbyl groups described previously herein, such as an aryl group, such as phenyl, which can be substituted with one or more of the substituting groups described previously herein, such as one or more hydroxyl groups and/or one or more linear or branched $C_1$-$C_{25}$ alkyl groups.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein may each be independently selected, such as, but not limited to, $R^1$-$R^{10}$, $R^{12}$, and $R^{13}$, can in each case be independently and optionally interrupted with at least one of —O—, —S—, —C(O)—, —C(O)O—, —OC(O)O—, —S(O)—, —SO$_2$—, —N($R^9$)— and —Si($R^9$)($R^{10}$)—. As used herein, by interrupted with at least one of —O—, —S—, —C(O)—, —C(O)O—, —OC(O)O—, —S(O)—, —SO$_2$—, —N($R^9$)—, and —Si($R^9$)($R^{10}$)—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two or more of the above recited linking groups, which can be adjacent to each other or separated by one or more carbons. For purposes of non-limiting illustration, a combination of adjacent —C(O)— and —N($R^9$)— can provide a divalent amide linking or interrupting group, —C(O)—N($R^9$)—. For purposes of further non-limiting illustration, a combination of adjacent —N($R^9$)—, —C(O)— and —O— can provide a divalent carbamate (or urethane) linking or interrupting group, —N($R^9$)—C(O)—O—, where $R^9$ is hydrogen.

The compounds of the present invention, for example as represented by Formula I, and the various groups thereof will be described in further detail herein as follows.

With some embodiments of the present invention, $R^1$ of the compound represented by Formula I is selected from hydrogen, linear or branched $C_1$-$C_{25}$ alkyl, linear or branched $C_2$-$C_{25}$ alkenyl, each optionally interrupted with a group selected from cyclohexylen-1,4-diyl, —O—, —C(O)—, and —Si(CH$_3$)$_2$—, and each optionally having at least one hydrogen replaced with F. With some further embodiments, $R^1$ of Formula I is selected from hydrogen, or linear or branched $C_1$-$C_8$ alkyl, such as methyl, ethyl, n-propyl, iso-propyl, n-butyl, iso-butyl, pentyl, hexyl, heptyl, and octyl (including structural isomers thereof, and at least partially fluorinated species thereof, such as —CF$_3$).

With some embodiments of the present invention, $R^2$, $R^3$, $R^4$ and $R^5$ of the compound represented by Formula I are each independently selected from hydrogen, linear or branched $C_1$-$C_{10}$ alkyl. With some further embodiments, $R^2$, $R^3$, $R^4$ and $R^5$ of Formula I are each independently selected from linear or branched $C_1$-$C_8$ alkyl, such as methyl, ethyl, n-propyl, iso-propyl, n-butyl, iso-butyl, pentyl, and hexyl (including structural isomers thereof).

With some embodiments of the present invention, $R^6$ of the compound represented by Formula I is selected from hydrogen, linear or branched $C_1$-$C_{25}$ alkyl, linear or branched $C_2$-$C_{25}$ alkenyl, each optionally interrupted with a group selected from cyclohexylen-1,4-diyl, —O—, —C(O)—, and —Si(CH$_3$)$_2$—, and each optionally having at least one hydrogen replaced with F. In accordance with some further embodiments, $R^6$ of Formula I is selected from hydrogen, and linear or branched $C_1$-$C_8$ alkyl, such as methyl, ethyl, n-propyl, iso-propyl, n-butyl, iso-butyl, pentyl, hexyl, heptyl, and octyl (including structural isomers thereof, and at least partially fluorinated species thereof, such as —CF$_3$).

According to some embodiments of the present invention, $R^1$, $R^2$, $R^3$, $R^4$ and $R^5$ are each methyl, and $R^6$ is hydrogen. With such embodiments, the piperidinyl portion of the compound represented by Formula I, can be represented by the following Formula A,

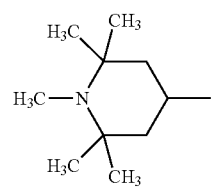

Formula A

The divalent linking group $L^1$ of the compound represented by Formula I is selected from a bond, or one of Formulas IIa, IIb, IIc, IId or IIe, as described previously herein. With Formulas IIb and IId, $R^7$ and $R^8$ can, in some embodiments, each be independently selected from divalent linear or branched $C_1$-$C_{25}$ alkyl (e.g., linear or branched $C_1$-$C_{25}$ alkylene), divalent linear or branched $C_2$-$C_{25}$ alkenyl (e.g., linear or branched $C_2$-$C_{25}$ alkenylene), divalent $C_3$-$C_{12}$ cycloalkyl (e.g., $C_3$-$C_{12}$ cycloalkylene), divalent $C_3$-$C_{12}$ heterocycloalkyl (e.g., $C_3$-$C_{12}$ heterocycloalkylene), divalent aryl (e.g., arylene), and divalent heteroaryl (e.g., heteroarylene). In accordance with further embodiments, $R^7$ and $R^8$ of Formulas IIb and IId, are each independently selected from divalent linear or branched $C_1$-$C_6$ alkyl (e.g., linear or branched $C_1$-$C_6$ alkylene), such as divalent methyl and divalent ethyl (e.g., methylene or ethylene, such as ethan-1,1-diyl or ethan-1,2-diyl). For purposes of non-limiting illustration, when $R^7$ and $R^8$ are each selected from divalent ethyl, —$R^7$— and —$R^8$— can each be represented by, —CH$_2$CH$_2$— (which can be referred to as ethan-1,2-diyl). With some embodiments of the present invention, $R^b$ of Formula IIe can be selected from linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl. In accordance with further embodiments, $R^b$ of Formula IIe can be selected from linear or branched $C_1$-$C_6$ alkyl, such as methyl and ethyl.

According to some embodiments, $L^1$ of Formula I is selected from Formula IId, and $R^8$ thereof is selected from divalent linear or branched $C_1$-$C_6$ alkyl. For purposes of non-limiting illustration, when $R^8$ is divalent methyl (or methyl ene), Formula IId can be represented by the following Formula Va,

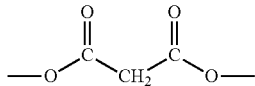
Formula Va

For purposes of further non-limiting illustration, when $R^8$ is divalent ethyl (or ethylene, or ethan-1,2-diyl), Formula IId can be represented by the following Formula Vb,

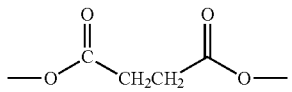
Formula Vb

With further reference to the compound represented by Formula I, at least one $L^2$ and/or at least one $L^3$ is present. With some embodiments, at least one $L^3$ is present, and optionally at least one $L^2$ group is present in the compound represented by Formula I. With some embodiments, at least one $L^3$ is present, and no $L^2$ groups are present in the compound represented by Formula I. In accordance with some embodiments of the present invention, at least one $L^2$ is present, and at least one $L^3$ is present, in which case m is at least 1 for at least one t, and p is at least one for at least one t.

The $L^2$ segments of the compound represented by Formula I can be described as flexible segments or moieties, relative to the $L^3$ segments which can be described as rigid segments or moieties. The terms flexible with regard to $L^2$, and rigid with regard to $L^3$ are relative to each other.

With some embodiments, $L^2$ of Formula I, is independently for each m, selected from divalent linear or branched $C_1$-$C_{25}$ alkyl (e.g., linear or branched $C_1$-$C_{25}$ alkylene), which is optionally interrupted with at least one of —O—, —C(O)O—, and —OC(O)O—, and combinations of two or more thereof. In accordance with further embodiments, $L^2$ of Formula I, is independently for each m, selected from divalent linear or branched $C_1$-$C_{10}$ alkyl, which is optionally interrupted with at least one of —O—, —C(O)O—, and —OC(O)O—.

According to some embodiments, at least one $L^2$ is selected from at least one group represented by the following Formulas B, C, and/or D,

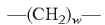          Formula B

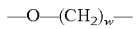          Formula C

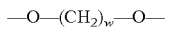          Formula D

With reference to Formulas B, C, and D each w is independently 1 to 25, or 1 to 10, or 1 to 8, or 1 to 6.

In accordance with some further embodiments, at least one $L^2$ is selected from a group represented by the following Formula E,

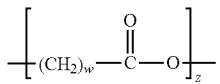
Formula E

With reference to Formula E, w is independently, for each z, 1 to 25, or 1 to 10, or 1 to 8, or 1 to 6, and z is from 1 to 25, or 1 to 10, or 1 to 8, or 1 to 6. When selected from groups represented by Formula E, $L^2$ can be derived from cyclic lactones, such as 6-caprolactone when w is 5.

According to some embodiments, at least one $L^2$ is a combination of: (i) a group represented by Formula E; and (ii) at least one group represented by Formula B, Formula C, and/or Formula D.

With some embodiments of the present invention, Z of Formula VI of $L^3$ is, independently for each v, selected from a bond, —O— and —C(O)O—.

With reference to Formula VI of $L^3$, the optional substituents of divalent ring-A and divalent ring-B can in each case be selected from substituents including, but not limited to, hydrocarbyl and substituted hydrocarbyl each optionally interrupted with at least one of —O—, —S—, —C(O)—, —C(O)O—, —OC(O)O—, —S(O)—, —SO$_2$—, and —Si($R^9$)($R^{10}$)— wherein $R^9$ and $R^{10}$ are each independently selected from hydrocarbyl and substituted hydrocarbyl, and combinations of two or more thereof. With some embodiments, the optional substituents of divalent ring-A and divalent ring-B can in each case be selected from substituents including, but not limited to, linear or branched $C_1$-$C_{25}$ alkyl, linear or branched $C_1$-$C_{25}$ alkenyl, linear or branched $C_1$-$C_{25}$ alkynyl, $C_3$-$C_{12}$ cycloalkyl, $C_3$-$C_{12}$ heterocycloalkyl (e.g., tetrahydrofuranyl, tetrahydropyranyl and piperidinyl), aryl (e.g., phenyl, benzyl, naphthyl, and anthracenyl), heteroaryl (e.g., furanyl, pyranyl and pyridinyl), halogen (e.g., F, Cl, Br and I), and combinations of two or more thereof.

With further reference to Formula VI of $L^3$, the divalent rings,

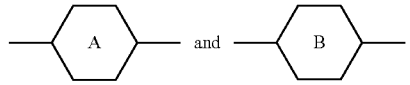

are, with some embodiments, each independently selected, for each v (for divalent ring-A) and each u (for divalent ring-B), from phenylen-1,4-diyl, or substituted phenylen-1,4-diyl, or cyclohexan-1,4-diyl, or substituted cyclohexan-1,4-diyl. With some further embodiments: at least one divalent ring-A is selected from phenylen-1,4-diyl, or substituted phenylen-1,4-diyl; and at least one divalent ring-B is selected from phenylen-1,4-diyl, or substituted phenylen-1,4-diyl.

As used herein, the term "divalent ring-A" means a divalent ring represented by the following formula,

In addition, as used herein, the term "divalent ring-B' means a divalent ring represented by the following formula,

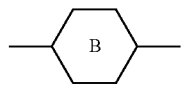

In accordance with some embodiments of the present invention, each $L^3$ is independently selected from (or $L^3$ is independently selected for each p from) the following Formulas VII(A) through VII(J),

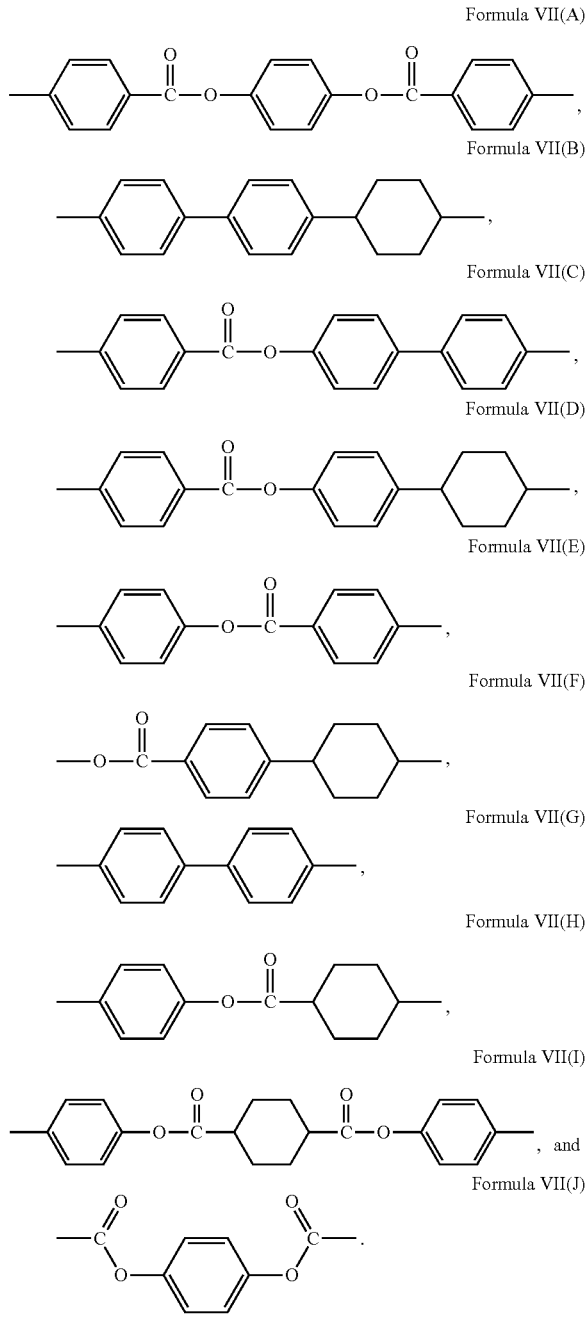

According to some embodiments of the present invention, E of the compound represented by Formula I is selected from hydrogen, linear or branched $C_1$-$C_{25}$ alkyl optionally interrupted with at least one of —O— and —C(O)O—, and linear or branched $C_2$-$C_{25}$ alkenyl optionally interrupted with at least one of —O— and —C(O)O—. With some further embodiments, E is selected from hydrogen and linear or branched $C_1$-$C_{10}$ alkyl optionally interrupted with at least one of —O— and —C(O)O—. According to some additional embodiments, E is selected from hydrogen and linear or branched $C_1$-$C_{10}$ alkyl.

The group E of Formula I, with some embodiments, can include a divalent group selected from at least one divalent group represented by Formulas B, C, D, and/or E, as described previously herein with reference to $L^2$.

The group E of the compound represented by Formula I can, in some embodiments, be substituted with at least one group represented by the following Formula F,

With reference to Formula F, $R^{11}$ is selected from hydrogen and linear or branched $C_1$-$C_8$ alkyl, such as methyl and ethyl.

The compounds of the present invention represented by Formula I can, in some embodiments, include at least one additional piperidinyl group represented by the following Formula G,

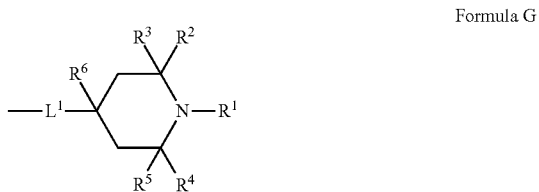

With reference to Formula G, $R^1$, $R^2$, $R^3$, $R^4$, $R^5$, $R^6$, and $L^1$ are each independently as described and defined previously herein with reference to Formula I.

Additionally or alternatively to including at least one additional piperidinyl group represented by Formula G, the compounds of the present invention represented by Formula I can, in some embodiments, include at least one hindered phenol group represented by the following Formula H,

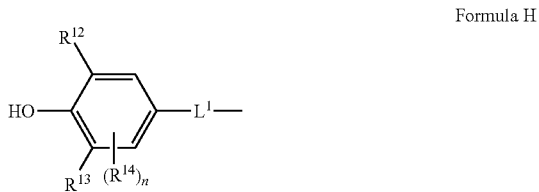

With reference to Formula H, $L^1$ is independently as described and defined previously herein with reference to Formula I, $R^{12}$ and $R^{13}$ are each independently selected from hydrogen, hydrocarbyl, and substituted hydrocarbyl, provided that at least one of $R^{12}$ and $R^{13}$ is selected from hydrocarbyl or substituted hydrocarbyl, and n is 0, 1 or 2, and $R^{14}$ is independently for each n selected from hydrocarbyl and substituted hydrocarbyl.

With some embodiments, at least one of: (i) E can be substituted with at least one piperidinyl group represented by Formula G, and/or E can be substituted with at least one hindered phenol group represented by Formula H; and/or (ii) at least one $L^2$ can be substituted with at least one piperidinyl group represented by Formula G, and/or at least one $L^2$ can be substituted with at least one hindered phenol group represented by Formula H; and/or (iii) at least one $L^3$ can be substituted with at least one piperidinyl group represented by Formula G, and/or at least one $L^3$ can be substituted with at least one hindered phenol group represented by Formula H.

With some embodiments, when E is directly linked to $L^1$ (and equivalently, when $L^1$ is directly linked to E) of Formulas G and/or H, the direct link therebetween (e.g., each direct E-L¹ link) is free of two heteroatoms linked (or bonded) together. With some additional embodiments, when $L^2$ is directly linked to $L^1$ (and equivalently, when $L^1$ is directly linked to $L^2$) of Formulas G and/or H, the direct link therebetween (e.g., each direct $L^2$-$L^1$ link) is free of two heteroatoms linked (or bonded) together. With some further embodiments, when $L^3$ is directly linked to $L^1$ (and equivalently, when $L^1$ is directly linked to $L^3$) of Formulas G and/or H, the direct link therebetween (e.g., each direct $L^3$-$L^1$ link) is free of two heteroatoms linked (or bonded) together.

In accordance with some embodiments of the present invention, at least one of: (i) E is substituted with at least one group selected from, a piperidinyl group represented by Formula G, and/or a hindered phenol group represented by Formula H; and/or (ii) at least one $L^3$ is substituted with at least one group selected from, a piperidinyl group represented by Formula G, and/or a hindered phenol group represented by Formula H.

According to some further embodiments of the present invention, with reference to the compound represented by Formula I: E is substituted with at least one hindered phenol group represented by Formula H; and at least one $L^3$ is substituted with a piperidinyl group represented by Formula G.

Compounds according to the present invention represented by Formula I more particularly include, but are not limited to, compounds represented by the following Formulas VIII(A) through VIII(N), Formula VIII(A)

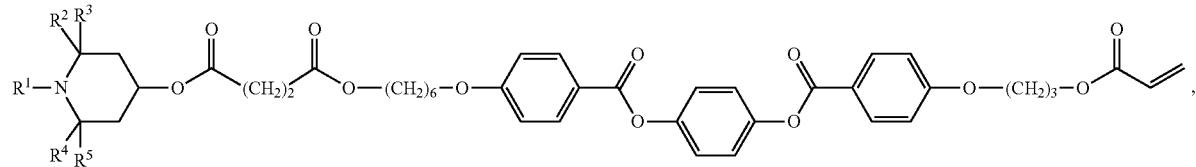

Formula VIII(B)

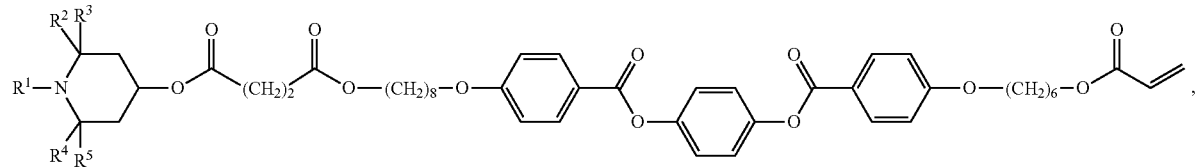

Formula VIII(C)

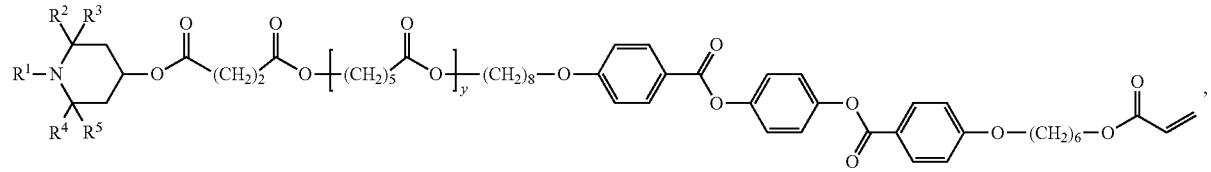

wherein y is from 1 to 25, such as 1 to 15, or 1 to 10, or 1 to 5,

Formula VIII(D)

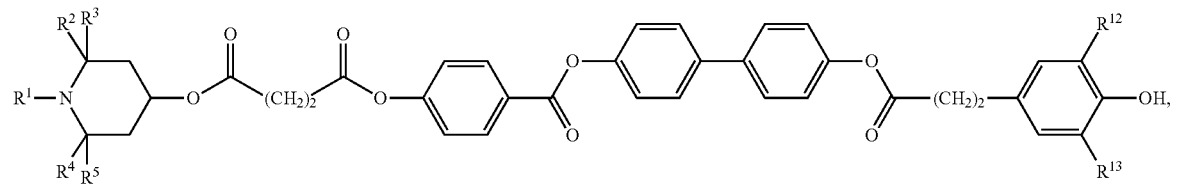

Formula VIII(E)

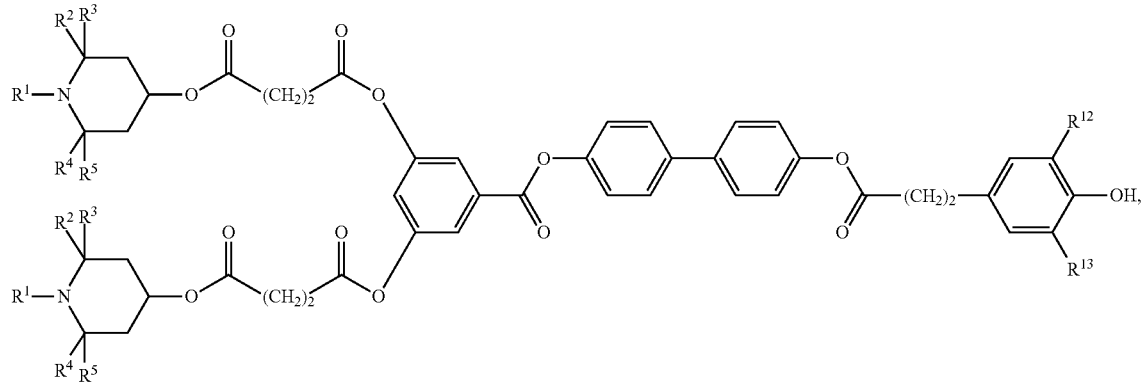

-continued
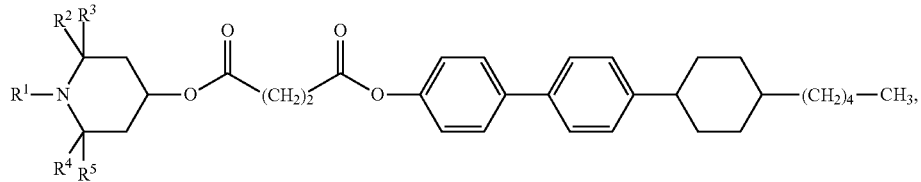
Formula VIII(F)
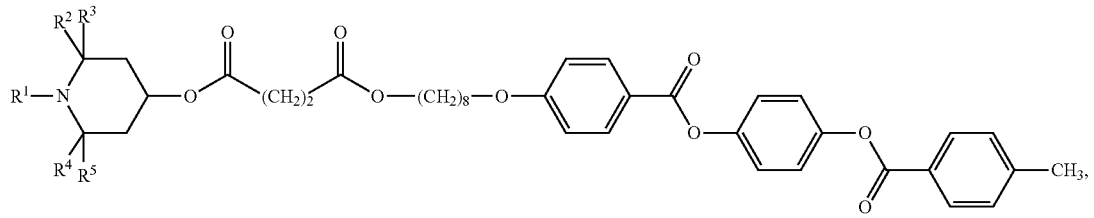
Formula VIII(G)
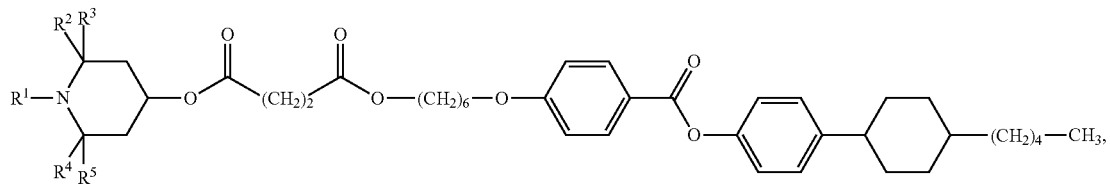
Formula VIII(H)
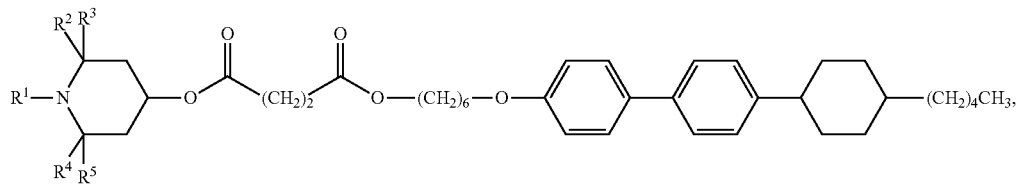
Formula VIII(I)
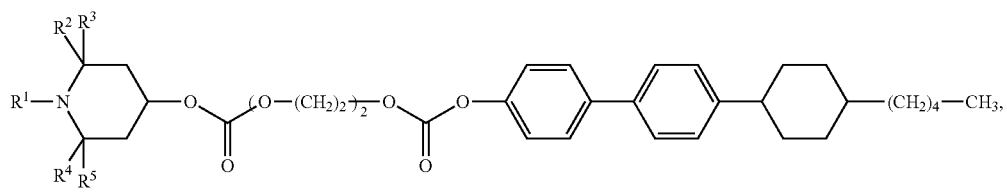
Formula VIII(J)
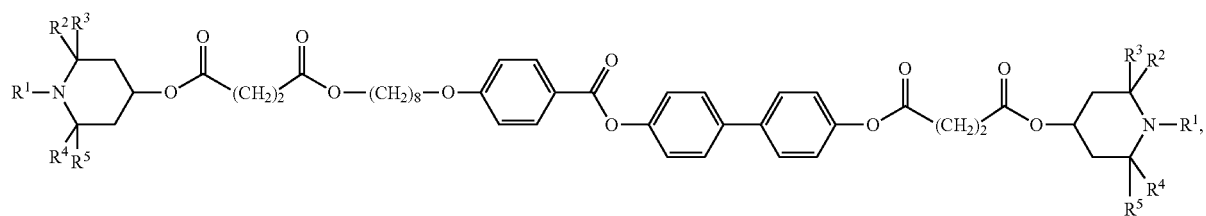
Formula VIII(K)
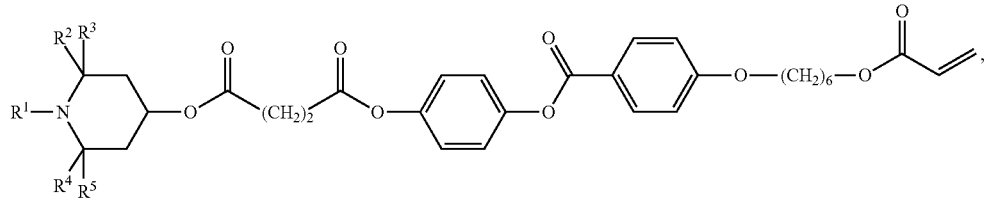
Formula VIII(L)

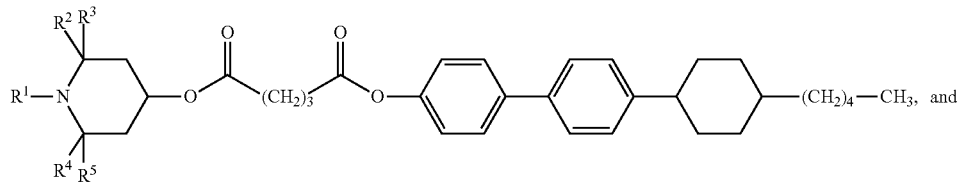

Formula VIII(M)

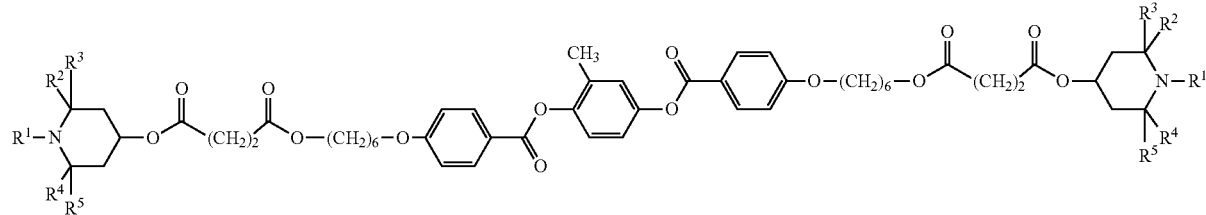

Formula VIII(N)

With reference to the compounds represented by Formulas VIII(A) through VIII(N), $R^1$, $R^2$, $R^3$, $R^4$, and $R^5$ are in each case independently selected from those groups as described previously herein with reference to Formula I, and $R^{12}$ and $R^{13}$ are in each case independently selected from those groups as described previously herein with reference to the hindered phenol group represented by Formula H. With some embodiments of the present invention and with further reference to the compounds represented by Formulas VIII(A) through VIII(N), $R^1$, $R^2$, $R^3$, $R^4$, and $R^5$ are in each case methyl, and $R^{12}$ and $R^{13}$ are in each case tertiary butyl.

With some embodiments, compounds according to the present invention, including those represented by Formula I, are mesogenic compounds, which include at least one mesogen segment (or unit or group). As discussed previously herein, a mesogen is the fundamental unit (or segment or group) of a liquid crystal material that induces, and/or is induced into, structural order amongst and between liquid crystals, such as liquid crystal materials that are together present in a liquid crystal composition. With reference to Formula I, the $L^3$ segment or segments (or unit/units) typically represent the mesogen (or mesogenic) segments or portions of the compounds of the present invention. Since the compounds of the present invention include at least one stabilizer group, such as the piperidinyl group of the compound represented by Formula I, the compounds of the present invention can be described as mesogenic stabilizers when also including at least one mesogen segment or group.

The present invention also relates to liquid crystal corn positions that include at least one compound represented by Formula I. Liquid crystal compositions according to the present invention, in some embodiments, in addition to at least one compound represented by Formula I, can further include at least one of a photochromic compound, a dichroic compound, and/or a photochromic-dichroic compound.

Liquid crystal compositions according to the present invention can optionally further include at least one additive. Examples of such optional additives include, but are not limited to, liquid crystal materials, liquid crystal property control additives, non-linear optical materials, dyes (e.g., static dyes), alignment promoters, kinetic enhancers, photoinitiators, thermal initiators, surfactants, polymerization inhibitors, solvents, light stabilizers, thermal stabilizers, mold release agents, rheology control agents, gelators, leveling agents, free radical scavengers, coupling agents, tilt control additives, block or non-block polymeric materials, and/or adhesion promoters.

The photochromic compounds that can be present in the liquid crystal compositions of the present invention can each independently have at least one photochromic group selected from, for example, thermally reversible pyrans, non-thermally reversible pyrans, thermally reversible oxazines, non-thermally reversible oxazines, thermally reversible fulgides, and/or non-thermally reversible fulgides. Photochromic compounds present in the liquid crystal compositions of the present invention, can alternatively or additionally include inorganic photochromic materials.

Examples of thermally reversible photochromic pyrans from which photochromic compound(s) can be chosen and that can be used with various embodiments of the present invention, such as the liquid crystal compositions of the present invention, include, but are not limited to: benzopyrans; naphthopyrans, e.g., naphtho[1,2-b]pyrans, naphtho[2,1-b]pyrans; indeno-fused naphthopyrans, such as those disclosed in U.S. Pat. No. 5,645,767 at col. 2, line 16 to col. 12, line 57; heterocyclic-fused naphthopyrans, such as those disclosed in U.S. Pat. No. 5,723,072 at col. 2, line 27 to col. 15, line 55, U.S. Pat. No. 5,698,141 at col. 2, line 11 to col. 19, line 45, U.S. Pat. No. 6,153,126 at col. 2, line 26 to col. 8, line 60, and U.S. Pat. No. 6,022,497 at col. 2, line 21 to col. 11, line 46; spiro-9-fluoreno[1,2-b]pyrans; phenanthropyrans; quinopyrans; fluoroanthenopyrans; spiropyrans, e.g., spiro (benzindoline)naphthopyrans, spiro(indoline)benzopyrans, spiro(indoline)naphthopyrans, spiro(indoline)quinopyrans and spiro(indoline)pyrans. Additional examples of naphthopyrans and related organic photochromic substances are described, for example, in U.S. Pat. No. 5,658,501 at col. 1, line 64 to col. 13, line 17. The pertinent cited portions of the preceding U.S. patents are incorporated herein by reference. Spiro(indoline)pyrans are also described in the text, *Techniques in Chemistry*, Volume III, "Photochromism", Chapter 3, Glenn H. Brown, Editor, John Wiley and Sons, Inc., New York, 1971.

Examples of thermally reversible photochromic oxazines from which photochromic compound(s) can be chosen and that can be used with various embodiments of the present invention, such as the liquid crystal compositions of the present invention, include, but are not limited to, benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine.

Examples of thermally reversible photochromic fulgides from which photochromic compound(s) can be chosen and that can be used with various embodiments of the present invention, such as the liquid crystal compositions of the present invention, include, but are not limited to: fulgimides, such as, 3-furyl and 3-thienyl fulgimides; fulgides, such as 3-furyl and 3-thienyl fulgides, which are disclosed in U.S. Pat. No. 4,931,220 at column 2, line 51 to column 10, line 7, and mixtures of any of the aforementioned photochromic materials/compounds. Examples of further non-thermally reversible photochromic compounds that can be used with various embodiments of the present invention, such as the liquid crystal compositions of the present invention include, but are not limited to the photochromic compounds disclosed in U.S. Pat. No. 7,342,112 at column 69, line 62 to column 71, line 20.

Examples of inorganic photochromic compounds from which photochromic compound(s) can be chosen and that can be used with various embodiments of the present invention, such as the liquid crystal compositions of the present invention, include, but are not limited to: metal halides, such as, silver halide, cadmium halide and/or copper halide; and inorganic photochromic materials may be prepared by the addition of europium(II) and/or cerium(II) to a mineral glass, such as a soda-silica glass. With some embodiments, the inorganic photochromic materials can be added to molten glass and formed into microparticles that are incorporated into the compositions of the present invention. The glass particulates can be formed by any of a number of various methods known in the art. Additional examples of suitable inorganic photochromic materials are further described in Kirk Othmer Encyclopedia of Chemical Technology, 4th ed., volume 6, pages 322-325.

The compositions of the present invention can include photosensitive materials, such as dyes, and in particular non-photochromic dyes including, but not limited to, luminescent dyes, such as phosphorescent dyes and/or a fluorescent dyes. While not intending to be bound by any theory, after activation, phosphorescent dyes and fluorescent dyes emit visible radiation when one or more activated/excited electrons thereof transitions from a higher to a lower electronic state. One difference between the two dye types is that the emission of luminescence after exposure to radiation from the fluorescent dye occurs sooner than that from a phosphorescent dye.

Examples of fluorescent dyes that can be used with compositions of the present invention include, but are not limited to, anthracenes tetracenes, pentacenes, rhodamines, benzophenones, coumarins, fluoresceins, perylenes, and mixtures thereof. Fluorescent dyes that can be used with compositions of the present invention are described in further detail in, for example, Haugland, R. P. *Molecular Probes Handbook for Fluorescent Probes and Research Chemicals,* 6th ed., 1996.

Examples of phosphorescent dyes that can be used with compositions of the present invention include, but are not limited to, metal-ligand complexes such as tris(2-phenylpyridine)iridium [Ir(ppy)$_3$] and 2,3,7,8,12,13,17,18-octaethyl-21H,23H-porphyrin platimum(II) [PtOEP]; and organic phosphorescent dyes such as eosin (2',4',5',7'-tetrabromofluorescein), 2,2'-bipyridine and erthrosin (2',4',5',7'-tetraiodofluorescein).

Examples of non-photosensitive materials that can be present in the compositions of the present invention include, but are not limited to, fixed-tint dyes (or static dyes). Examples of suitable fixed-tint dyes include, but are not limited to, nitrobenzene dyes, azo dyes, anthraquinone dyes, naphthoquinone dyes, benzoquinone dyes, phenothiazine dyes, indigoid dyes, xanthene dyes, pheanthridine dyes, phthalocyanin dyes, and dyes derived from triarylmethane. Fixed-tint dyes, such as those classes and examples cited herein, can be used alone or as mixtures with other fixed-tint dyes and/or other chromophoric compounds, such as photochromic compounds.

With some embodiments of the present invention, dyes can be used in combination with other chemical compounds to form thermochromic materials. Examples of dyes, that can be used in combination with other chemical compounds to form thermochromic materials, include, but are not limited to: substituted phenylmethanes and fluorans, such as 3,3'-dimethoxyfluoran (yellow); 3-chloro-6-phenylaminofluoran (orange); 3-diethylamino-6-methyl-7-chlorofluoran (vermilion); 3-diethyl-7,8-benzofluoran (pink); Crystal Violet lactone (blue); 3,3',3"-tris(p-dimethylaminophenyl)phthalide (purplish blue); Malachite Green lactone (green); 3,3-bis(pdimethylaminophenyl)phthalide (green); 3-diethylamino-6-methyl-7-phenylaminofluoran (black); indolyl phthalides; spiropyrans; coumarins; fulgides; etc. Additional classes of thermochromic materials include, but are not limited to, cholesteric liquid crystals and mixtures of cholesteric liquid crystals and nematic liquid crystals.

With some embodiments of the compositions according to the present invention, the photochromic compound can include at least two photochromic groups, in which the photochromic groups are linked to one another by way of linking group substituents on the individual photochromic groups. For example, the photochromic groups can be polymerizable photochromic groups, or photochromic groups that are adapted to be compatible with a host material, which can be referred to herein as "compatibilized photochromic groups." Examples of polymerizable photochromic groups include, but are not limited to, those disclosed in U.S. Pat. No. 6,113,814 at column 2, line 24 to column 22, line 7. Examples of compatibilized photochromic groups include, but are not limited to, those disclosed in U.S. Pat. No. 6,555,028 at column 2, line 40 to column 24, line 56.

Examples of additional photochromic groups and complementary photochromic groups, that can be included with or used in conjunction with the compositions of the present invention include, but are not limited to, those described in U.S. Pat. No. 6,080,338 at column 2, line 21 to column 14, line 43; U.S. Pat. No. 6,136,968 at column 2, line 43 to column 20, line 67; U.S. Pat. No. 6,296,785 at column 2, line 47 to column 31, line 5; U.S. Pat. No. 6,348,604 at column 3, line 26 to column 17, line 15; U.S. Pat. No. 6,353,102 at column 1, line 62 to column 11, line 64; and U.S. Pat. No. 6,630,597 at column 2, line 16 to column 16, line 23.

With some embodiments, the liquid crystal compositions of the present invention can include a photochromic compound and/or a photochromic-dichroic compound that in each case is independently selected from indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, non-thermally reversible photochromic compounds, and mixtures thereof.

Photochromic compounds and photochromic-dichroic compounds that can be included in the compositions of the present invention, include, indeno-fused naphthopyrans represented by the following Formula IX, in which the ring atoms are numbered as shown,

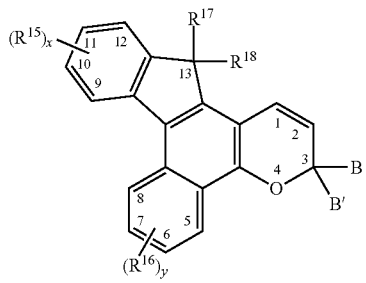

The indeno-fused naphthopyran represented by Formula IX can be referred to as an indeno[2',3':3,4]naphtho[1,2-b]pyran. Subscript x and subscript y of Formula IX can each independently be from 1 to 4. Each $R^{15}$ for each x, each $R^{16}$ for each y, $R^{17}$, $R^{18}$, B and B' can each be independently selected from hydrogen, hydrocarbyl groups and substituted hydrocarbyl groups, which each can be optionally interrupted with at least one of —O—, —S—, —C(O)—, —C(O)O—, —S(O)—, —SO$_2$—, —Si($R^9$)$R^{10}$)— —N($R_{11}$')—, where $R_{11}$' is selected from hydrocarbyl.

With some embodiments of the present invention, $R^{15}$ for each x, and $R^{16}$ for each y, are in each case independently selected from: a reactive substituent; a compatibilizing substituent; halogen selected from fluoro and chloro; $C_1$-$C_{20}$ alkyl; $C_3$-$C_{10}$ cycloalkyl; substituted or unsubstituted phenyl; or —O—$R_{10}$' or —C(O)—$R_{10}$' or —C(O)—O$R_{10}$', wherein $R_{10}$' is hydrogen, $C_1$-$C_{20}$ alkyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl. The phenyl substituents (i.e., the substituents of the substituted phenyl) can be selected from hydroxyl, halogen, carbonyl, $C_1$-$C_{20}$ alkoxycarbonyl, cyano, halo($C_1$-$C_{20}$)alkyl, $C_1$-$C_{20}$ alkyl or $C_1$-$C_{20}$ alkoxy.

With some embodiments of the present invention, $R^{15}$ for each x, and $R^{16}$ for each y, are in each case independently selected from: $C_1$-$C_6$ alkyl; $C_3$-$C_7$ cycloalkyl; substituted or unsubstituted phenyl; —O$R_{10}$' or —OC(=O)$R_{10}$', wherein $R_{10}$' is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$) alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl. The phenyl substituents (i.e., the substituents of the substituted phenyl) can be more particularly selected from hydroxyl, halogen, carbonyl, $C_1$-$C_6$ alkoxycarbonyl, cyano, halo($C_1$-$C_6$)alkyl, $C_1$-$C_6$ alkyl or $C_1$-$C_6$ alkoxy.

Alternatively or in addition to the previously recited classes and examples, $R^{15}$ for each x, and $R^{16}$ for each y, are in each case independently selected from, —N($R_{11}$')$R_{12}$', wherein $R_{11}$' and $R_{12}$' are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}$' and $R_{12}$' come together with the nitrogen atom to form a $C_3$-$C_{20}$ hetero-bicycloalkyl ring or a $C_4$-$C_{20}$ hetero-tricycloalkyl ring.

Further alternatively or in addition to the previously recited classes and examples, $R^{15}$ for each x, and $R^{16}$ for each y, are in each case independently selected from, a nitrogen containing ring represented by the following graphic Formula IXA,

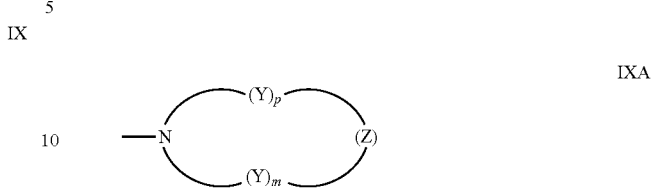

With the nitrogen ring substituent represented by general Formula IXA, each —Y— is independently chosen for each occurrence from —CH$_2$-, —CH($R_{13}$')—, —C($R_{13}$')$_2$—, —CH(aryl)-, —C(aryl)$_2$-, and —C($R_{13}$')(aryl)-, and Z is —Y—, —O—, —S—, —S(O)—, —SO$_2$—, —NH—, —N($R_{13}$')—, or —N(aryl)-, wherein each $R_{13}$' is independently $C_1$-$C_{20}$ alkyl (e.g., $C_1$-$C_6$ alkyl), each aryl is independently phenyl or naphthyl, m is an integer 1, 2 or 3, and p is an integer 0, 1, 2, or 3 and provided that when p is 0, Z is —Y—.

Additionally or alternatively, $R^{15}$ for each x, and $R^{16}$ for each y, can in each case also be independently selected from a nitrogen containing ring substituent represented by general formula IXB and/or general formula IXC:

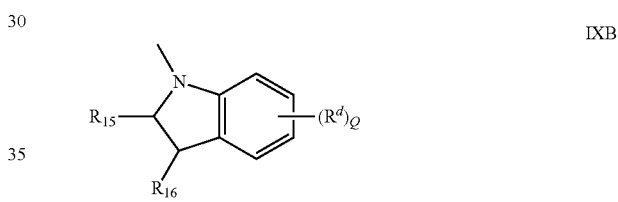

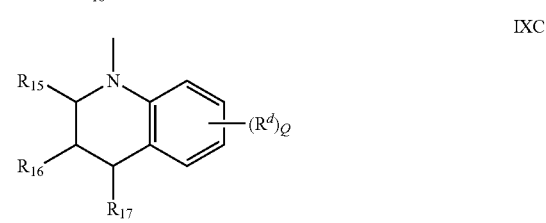

For the nitrogen containing ring substituents represented by general formulas IXB and IXC, $R_{15}$, $R_{16}$, and $R_{17}$ are each independently hydrogen, $C_1$-$C_{20}$ alkyl (e.g., $C_1$-$C_6$ alkyl), phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl (e.g., $C_1$-$C_6$ alkyl), $C_1$-$C_{20}$ alkoxy (e.g., $C_1$-$C_6$ alkoxy), fluoro or chloro, and Q is an integer 0, 1, 2, or 3.

Further alternatively or additionally, $R^{15}$ for each x, and $R^{16}$ for each y, can in each case also be independently selected from, unsubstituted, mono-, or di-substituted $C_4$-$C_{18}$ spirobicyclic amine, or unsubstituted, mono-, and di-substituted $C_4$-$C_{18}$ spirotricyclic amine, wherein the substituents are independently aryl, $C_1$-$C_{20}$ alkyl (e.g., $C_1$-$C_6$ alkyl), $C_1$-$C_{20}$ alkoxy (e.g., $C_1$-$C_6$ alkoxy), or phenyl($C_1$-$C_{20}$)alkyl (e.g., phenyl($C_1$-$C_6$)alkyl).

With some embodiments of the present invention, two adjacent $R^{15}$ groups, and/or two adjacent $R^{16}$ groups, can together form a group represented by the following general formula IXD or general formula IXE,

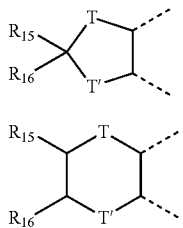
IXD

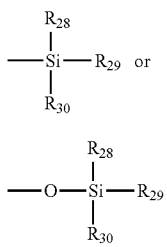
IXE

With the groups represented by general formulas IXD and IXE, T and T' are each independently oxygen or the group —$NR_{11}$—, where $R_{11}$, $R_{15}$, and $R_{16}$ are each as set forth and described previously herein.

With some embodiments, $R^{15}$ for each x, and $R^{16}$ for each y, can in each case also be independently selected from a silicon-containing group represented by one of the following Formulas IXF and IXG, $$-\underset{\underset{R_{30}}{|}}{\overset{\overset{R_{28}}{|}}{Si}}-R_{29} \text{ or}$$  IXF $$-O-\underset{\underset{R_{30}}{|}}{\overset{\overset{R_{28}}{|}}{Si}}-R_{29}$$  IXG in which $R_{28}$, $R_{29}$, and $R_{30}$ are each independently $C_1$-$C_{10}$ alkyl, $C_1$-$C_{10}$ alkoxy or phenyl; hydrogen, hydroxy, $C_1$-$C_6$ alkyl, chloro, fluoro, $C_3$-$C_7$ cycloalkyl, allyl or $C_1$-$C_8$ haloalkyl.

The $R^{17}$ and $R^{18}$ groups of Formula IX, with some embodiments of the present invention, can each be independently selected from: a reactive substituent; a compatibilizing substituent; hydrogen; hydroxy; $C_1$-$C_{20}$ alkyl (e.g., $C_1$-$C_6$ alkyl); $C_1$-$C_{20}$ haloalkyl (e.g., $C_1$-$C_6$ haloalkyl); $C_3$-$C_{10}$ cycloalkyl (e.g., $C_3$-$C_7$ cycloalkyl); allyl; benzyl; or mono-substituted benzyl. The benzyl substituents can be chosen from halogen, $C_1$-$C_{20}$ alkyl (e.g., $C_1$-$C_6$ alkyl) or $C_1$-$C_{20}$ alkoxy (e.g., $C_1$-$C_6$ alkoxy).

The $R^{17}$ and $R^{18}$ groups of Formula IX, with some further embodiments of the present invention, can each be independently selected from, an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl. The group substituents can in each case be independently chosen from halogen, $C_1$-$C_{20}$ alkyl (e.g., $C_1$-$C_6$ alkyl) or $C_1$-$C_{20}$ alkoxy (e.g., $C_1$-$C_6$ alkoxy).

The $R^{17}$ and $R^{18}$ groups can also, with some embodiments of the present invention, each be independently selected from a mono-substituted phenyl, in which the phenyl has a substituent located at the para position thereof, which is a linking group, —$(CH_2)_t$— or —O—$(CH_2)_t$—, that is connected to an aryl group which is a member of a (or another) photochromic material, such as a naphthopyran, an indeno-fused naphthopyran, or benzopyran, and t is chosen from the integer 1, 2, 3, 4, 5 or 6.

Alternatively, the $R^{17}$ and $R^{18}$ groups can each be independently selected from the group —$CH(R^{10})G$, in which $R^{10}$ is hydrogen, $C_1$-$C_{20}$ alkyl (e.g., $C_1$-$C_6$ alkyl) or the unsubstituted, mono- or di-substituted aryl groups phenyl or naphthyl, and G is —$CH_2OR^{11}$, in which $R^{11}$ is hydrogen, —$C(O)R^{10}$, $C_1$-$C_{20}$ alkyl (e.g., $C_1$-$C_6$ alkyl), $C_1$-$C_{20}$ alkoxy($C_1$-$C_{20}$)alkyl (e.g., $C_1$-$C_3$ alkoxy($C_1$-$C_6$)alkyl), phenyl($C_1$-$C_{20}$)alkyl (e.g., phenyl($C_1$-$C_3$)alkyl), mono($C_1$-$C_{20}$)alkoxy substituted phenyl($C_1$-$C_{20}$)alkyl (e.g., mono($C_1$-$C_6$)alkoxy substituted phenyl($C_1$-$C_3$)alkyl), or the unsubstituted, mono- or di-substituted aryl groups phenyl or naphthyl. The substituents of the phenyl and naphthyl groups can each be independently selected from $C_1$-$C_{20}$ alkyl (e.g., $C_1$-$C_6$ alkyl) or $C_1$-$C_{20}$ alkoxy (e.g., $C_1$-$C_6$ alkoxy).

With some further embodiments of the present invention, $R^{17}$ and $R^{18}$ can together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom. The spiro-carbocyclic ring and the spiro-heterocyclic ring are each annellated with 0, 1 or 2 benzene rings. The substituents of the spiro rings can be chosen from hydrogen or $C_1$-$C_{20}$ alkyl (e.g., $C_1$-$C_6$ alkyl).

With some embodiments of the present invention, $R^{15}$ for each x, and $R^{16}$ for each y, are in each case independently selected from unsubstituted phenyl, substituted phenyl, $C_1$-$C_6$ alkyl, $C_3$-$C_7$ cycloalkyl, $C_1$-$C_8$ haloalkyl, fluoro, chloro, and —O—$R_{10}$'. With further embodiments of the present invention, $R^{17}$ and $R^{18}$ are each independently selected from hydrogen, $C_1$-$C_8$ alkyl, $C_1$-$C_8$ haloalkyl, and $C_3$-$C_7$ cycloalkyl, or $R^{17}$ and $R^{18}$ together form a spiro substituent selected from a substituted or unsubstituted spiro-carbocyclic ring containing 3 to 6 carbon atoms.

In accordance with some further embodiments of the present invention, $R^{15}$ for each x, and $R^{16}$ for each y, can in each case be independently selected from a group represented by the following Formula X, $$-(S_1)_c-(Q_1-(S_2)_d)_{d'}-(Q_2-(S_3)_e)_{e'}-(Q_3-(S_4)_f)_{f'}-S_5-P \qquad X$$

With reference to Formula X, $Q_1$, $Q_2$, and $Q_3$ are each independently chosen from, a divalent group chosen from, an unsubstituted or a substituted aromatic group, an unsubstituted or a substituted alicyclic group, an unsubstituted or a substituted heterocyclic group, and mixtures thereof.

The substituents of the substituted aromatic groups, substituted alicyclic groups and substituted heterocyclic groups from which each of $Q_1$, $Q_2$, and $Q_3$ can be selected, are independently chosen from: a group represented by P (as will be described in further detail herein); liquid crystal mesogens; halogen; poly($C_1$-$C_{18}$ alkoxy); $C_1$-$C_{18}$ alkoxycarbonyl; $C_1$-$C_{18}$ alkylcarbonyl; $C_1$-$C_{18}$ alkoxycarbonyloxy; aryloxycarbonyloxy; perfluoro($C_1$-$C_{18}$)alkoxy; perfluoro($C_1$-$C_{18}$)alkoxycarbonyl; perfluoro($C_1$-$C_{18}$)alkylcarbonyl; perfluoro($C_1$-$C_{18}$)alkylamino; di-(perfluoro($C_1$-$C_{18}$)alkyl)amino; perfluoro($C_1$-$C_{18}$)alkylthio; $C_1$-$C_{18}$ alkylthio; $C_1$-$C_{18}$ acetyl; $C_3$-$C_{10}$ cycloalkyl; $C_3$-$C_{10}$ cycloalkoxy; or a straight-chain or branched $C_1$-$C_{18}$ alkyl group that is mono-substituted with cyano, halo, or $C_1$-$C_{18}$ alkoxy, or poly-substituted with halo.

Additionally or alternatively, the substituents of the substituted aromatic groups, substituted alicyclic groups and substituted heterocyclic groups from which each of $Q_1$, $Q_2$, and $Q_3$ can be selected, can be further independently chosen from a group represented by one of the following formulas XIIIA and XIIIB, —$M(T)_{(t-1)}$ \hfill XIIIA —$M(OT)_{(t-1)}$, \hfill XIIIB With reference to Formulas XIIIA and XIIIB, M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M.

Liquid crystal mesogens from which each of $Q_1$, $Q_2$, and $Q_3$ can each be independently selected, include but are not limited to art-recognized liquid crystal mesogens. With some embodiments, the liquid crystal mesogens can be selected from those described in U.S. Pat. Nos. 7,910,019 A1 and 7,910,020, the disclosures of which are incorporated herein by reference in their entirety.

With some further embodiments of the present invention, liquid crystal mesogens from which each of $Q_1$, $Q_2$, and $Q_3$ can each be independently selected, include but are not limited to the $L^3$ groups as described previously herein with reference to Formula I. For purposes of non-limiting illustration, $Q_1$, $Q_2$, and $Q_3$ can each be independently selected from Formulas VII(A) through VII(J) as described previously herein with regard to $L^3$ of Formula I.

With further reference to Formula X, the subscripts c, d, e, and f are each independently chosen from an integer ranging from 1 to 20, inclusive of the upper and lower limits (e.g., from 2 to 15, or from 3 to 10).

The $S_1$, $S_2$, $S_3$, $S_4$, and $S_5$ groups of Formula X are each independently chosen from a spacer unit. The spacer unit can in each case be independently chosen from, $—(CH_2)_g—$, $—(CF_2)_h—$, $—Si(CH_2)_g—$, $—(Si(CH_3)_2O)_h—$, in which g is independently chosen for each occurrence from 1 to 20, and h is a whole number from 1 to 16 inclusive. Alternatively, or additionally, the spacer unit can be independently chosen from $—N(Z)—$, $—C(Z)=C(Z)—$, $—C(Z)=N—$, $—C(Z')—C(Z')—$, or a single bond, in which Z is independently chosen for each occurrence from hydrogen, $C_1$-$C_{18}$ alkyl, $C_3$-$C_{10}$ cycloalkyl and aryl, and Z' is independently chosen for each occurrence from $C_1$-$C_{18}$ alkyl, $C_3$-$C_{10}$ cycloalkyl and aryl. Further alternatively, or additionally, the spacer unit can be independently chosen from $—O—$, $—C(O)—$, $—C\equiv C—$, $—N=N—$, $—S—$, $—S(O)—$, $—S(O)(O)—$, $—(O)S(O)O—$, $—O(O)S(O)O—$, or straight-chain or branched $C_1$-$C_{24}$ alkylene residue, said $C_1$-$C_{24}$ alkylene residue being unsubstituted, mono-substituted by cyano or halo, or poly-substituted by halo.

With further reference to Formula X: when two spacer units comprising heteroatoms are linked together, the spacer units are linked so that heteroatoms are not directly linked to each other; each bond between $S_1$ and the ring having positions 9-12 and $S_1$ and the ring having positions 5-8 is free of two heteroatoms linked together; and the bond between $S_5$ and P is free of two heteroatoms linked to each other.

The P group of Formula X is chosen from, hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylenyl, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof. The substituents of the groups from which P can be selected are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof. With some embodiment P can be a structure having from 2 to 4 reactive groups. With further embodiments, P can be an unsubstituted or substituted ring opening metathesis polymerization precursor.

With further reference to Formula X, subscripts d', e' and f' are each independently chosen from 0, 1, 2, 3, and 4, provided that the sum of d'+e'+f' is at least 1.

The B and B' groups of the indeno-fused naphthopyran represented by Formula IX are each independently selected from substituted and unsubstituted aromatic groups, and substituted and unsubstituted heteroaromatic groups, or B and B' taken together form an unsubstituted or substituted fluoren-9-ylidene. More particularly, B and B' can each independently be selected from: an aryl group that is mono-substituted with a reactive substituent or a compatibilizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl. The phenyl, aryl, 9-julolindinyl, or heteroaromatic substituents are selected from: a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

The phenyl, aryl and heteroaromatic substituents (i.e., the substituents of the substituted phenyl, aryl and heteroaromatic groups) of the B and B' groups can each be independently selected from: hydroxyl, a group $—C(=O)R_{21}$, wherein $R_{21}$ is $—OR_{22}$, $—N(R_{23})R_{24}$, piperidino, or morpholino, wherein $R_{22}$ is allyl, $C_1$-$C_{20}$ alkyl, phenyl, mono($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and said halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$ cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$)alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$)alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen.

The phenyl, aryl and heteroaromatic substituents (i.e., the substituents of the substituted phenyl, aryl and heteroaromatic groups) of the B and B' groups can, in some embodiments, each be independently and more particularly selected from: hydroxyl, a group —C(=O)$R_{21}$, wherein $R_{21}$ is —$OR_{22}$, —N($R_{23}$)$R_{24}$, piperidino, or morpholino, wherein $R_{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, $R_{23}$ and $R_{24}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy, and said halo substituent is chloro or fluoro, aryl, mono($C_1$-$C_{12}$)alkoxyaryl, di($C_1$-$C_{12}$)alkoxyaryl, mono($C_1$-$C_{12}$)alkylaryl, di($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl ($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, nnono($C_1$-$C_{12}$)alkoxy($C_1$-$C_{12}$)alkyl, acryloxy, methacryloxy, or halogen.

The B and B' groups can also each independently be an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{20}$ alkyl (e.g., $C_1$-$C_{12}$ alkyl), $C_1$-$C_{20}$ alkoxy (e.g., $C_1$-$C_{12}$ alkoxy), phenyl, or halogen.

In addition, the B and B' groups can each be independently selected from a group represented by the following general Formulas XIA or XIB,

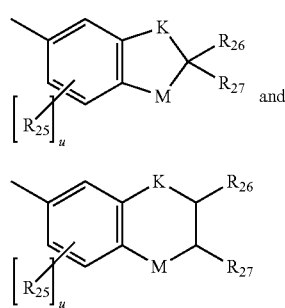

XIA

XIB

Independently with each of general formulas XIA and XIB, K is —$CH_2$— or —O—, and M is —O— or substituted nitrogen, provided that when M is substituted nitrogen, K is —$CH_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{20}$ alkoxy, hydroxy, and halogen, $R_{26}$ and $R_{27}$ each being independently hydrogen or $C_1$-$C_{20}$ alkyl, and u is an integer ranging from 0 to 2.

Each B and B' group can independently be a group represented by the following general Formula XIC,

XIC

With the group represented by general Formula XIC, $R_{28}$ is hydrogen or $C_1$-$C_{12}$ alkyl, and $R_{29}$ is an unsubstituted, mono- or di-substituted group chosen from naphthyl, phenyl, furanyl, and thienyl. The substitutents of the mono- or di-substituted naphthyls, phenyls, furanyls, and thienyls, are in each case independently selected from $C_1$-$C_{12}$ alkyl, $C_1$-$C_{12}$ alkoxy, or halogen.

The B and B' groups can together form a member selected from, a fluoren-9-ylidene, a mono-substituted fluoren-9-ylidene, or a di-substituted fluoren-9-ylidene. The substituents of the mono-substituted fluoren-9-ylidene, and the di-substituted fluoren-9-ylidene can in each case be independently selected from $C_1$-$C_{20}$ alkyl (e.g., $C_1$-$C_{12}$ alkyl), $C_1$-$C_{20}$ alkoxy (e.g., $C_1$-$C_{12}$ alkoxy), or halogen.

With some embodiments of the present invention, with the indeno-fused ring pyran compounds, for example, represented by Formula IX: $R^{15}$ for each x, and $R^{16}$ for each y, are in each case independently selected from $C_1$-$C_6$ alkyl, $C_3$-$C_7$ cycloalkyl, $C_1$-$C_8$ haloalkyl, fluoro, chloro, and —O—$R_{10}$'; $R^{17}$ and $R^{18}$ are each independently selected from hydrogen, $C_1$-$C_8$ alkyl, $C_1$-$C_8$ haloalkyl, and $C_3$-$C_7$ cycloalkyl, or together form a Spiro substituent selected from a substituted or unsubstituted spiro-carbocyclic ring containing 3 to 6 carbon atoms; and B and B' are each independently selected from aryl (e.g., phenyl) substituted with $C_1$-$C_6$ alkoxy, and aryl (e.g., phenyl) substituted with morpholino.

With some embodiments of the present invention, B and B' of the indeno-fused ring pyran compound represented by Formula IX can each be independently selected from polyalkoxy, and polyalkoxy having a polymerizable group. The polyalkoxy, and polyalkoxy having a polymerizable group from which B and B' can each be independently selected can be represented by the following Formulas XID and XIE.

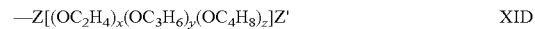

XID

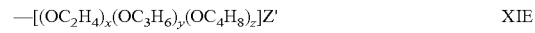

XIE

With Formulas XID and XIE, —Z is chosen from —C(O)— or —$CH_2$—, Z' is chosen from $C_1$-$C_3$ alkoxy or a polymerizable group. As used herein, the term "polymerizable group" means any functional group capable of participating in a polymerization reaction.

With some embodiments, polymerization of polymerizable photochromic compounds, such as polymerizable indeno-fused ring pyran compounds, including polymerizable indeno-fused naphthopyrans, can occur by mechanisms described with regard to the definition of "polymerization" in *Hawley's Condensed Chemical Dictionary*, Thirteenth Edition, 1997, John Wiley & Sons, pages 901-902. Those mechanisms include: by "addition," in which free radicals are the initiating agents that react with the ethylenically unsaturated double bond of the monomer by adding to it on one side at the same time producing a new free electron on the other side; by "condensation," involving the splitting out of a component, such as water molecules, by two reacting monomers; and by so-called "oxidative coupling."

Examples of polymerizable groups include, but are not limited to, hydroxy, thiol, isocyanate groups, oxirane groups (e.g., oxiranylmethyl), radically polymerizable ethylenically unsaturated groups, allyl groups, (meth)acryloxy, and 2-(methacryloxy)ethylcarbamyl. When there are 2 or more polymerizable groups on the indeno-fused ring pyran compound, they can be the same or different.

With some embodiments and with further reference to Formulas XID and XIE: the group, $—(OC_2H_4)_x—$, can represent poly(ethylene oxide); the group $—(OC_3H_6)_y—$, can represent poly(propylene oxide); and the group $—(OC_4H_8)_z—$, can represent poly(butylene oxide). When used in combination, the poly(ethylene oxide), poly(propylene oxide) and poly(butylene oxide) groups of Formulas XID and XIE can be in a random or block order within the polyalkoxy moiety. The subscript letters x, y and z of Formulas XID and XIE are each independently a number between 0 and 50, and the sum of x, y and z is between 2 and 50. The sum of x, y and z can be any number that falls within the range of 2 to 50 (e.g., 2, 3, 4 . . . 50). This sum can also range from any lower number to any higher number within the range of 2 to 50 (e.g., 6 to 50, 31 to 50). The numbers for x, y, and z are average values and can be partial numbers (e.g., 9.5).

As previously discussed, some of the groups of the photochromic compounds that can be included in the compositions of the present invention, such as each of the $R^{15}$, $R^{16}$, $R^{17}$, $R^{18}$, B and B' groups of the indeno-fused naphthopyran represented by Formula IX, can independently be selected from or include at least one of a reactive substituent and/or a compatibilizing substituent. If the photochromic compounds, such as the indeno-fused naphthopyran compound represented by Formula IX, include multiple reactive substituents and/or multiple compatibilizing substituents, each reactive substituent and each compatibilizing substituent can be independently chosen.

The reactive substituent and the compatibilizing substituent can each independently be represented in each case by one of:

| -A'-D-E-G-J (XVII); | -G-E-G-J (XX); | -D-E-G-J (XXIII); |
| -A'-D-J (XVIII); | -D-G-J (XXI); | -D-J (XXIV); |
| -A'-G-J (XIX); | -G-J (XXII); and | -A'-J (XXV). |

With formulas (XVII) through (XXV), non-limiting examples of groups that -A'- can represent according to various non-limiting embodiments disclosed herein include —O—, —C(=O)—, —CH₂—, —OC(=O)— and —NHC (=O)—, provided that if -A'- represents —O—, -A'- forms at least one bond with -J.

Non-limiting examples of groups that -D- can represent according to various non-limiting embodiments include a diamine residue or a derivative thereof, wherein a first amino nitrogen of said diamine residue can form a bond with -A'-, or a substituent or an available position on the compound (such as the indeno-fused naphthol or indeno-fused naphthopyran), and a second amino nitrogen of said diamine residue can form a bond with -E-, -G- or -J; and an amino alcohol residue or a derivative thereof, wherein an amino nitrogen of the amino alcohol residue can form a bond with -A'-, or a substituent or an available position on the compound (such as the indeno-fused naphthol or indeno-fused naphthopyran), and an alcohol oxygen of said amino alcohol residue can form a bond with -E-, -G- or -J. Alternatively, according to various non-limiting embodiments disclosed herein the amino nitrogen of said amino alcohol residue can form a bond with -E-, -G- or -J, and said alcohol oxygen of said amino alcohol residue can form a bond with -A'-, or a substituent or an available position on the compound (such as the indeno-fused ring compound or indeno-fused ring pyran compound).

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. Specific non-limiting examples diamine residues that can be used in conjunction with various non-limiting embodiments disclosed herein include the following:

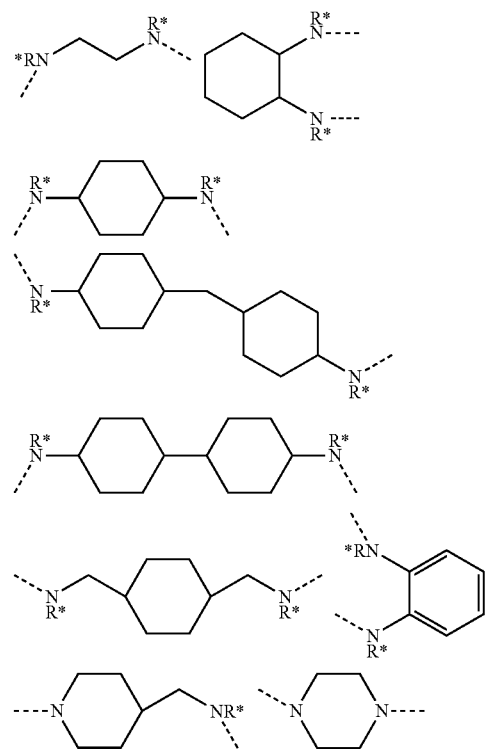

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. Specific non-limiting examples amino alcohol residues that can be used in conjunction with various non-limiting embodiments disclosed herein include the following:

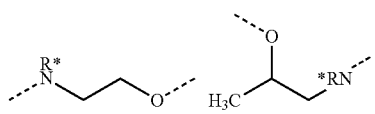

-continued

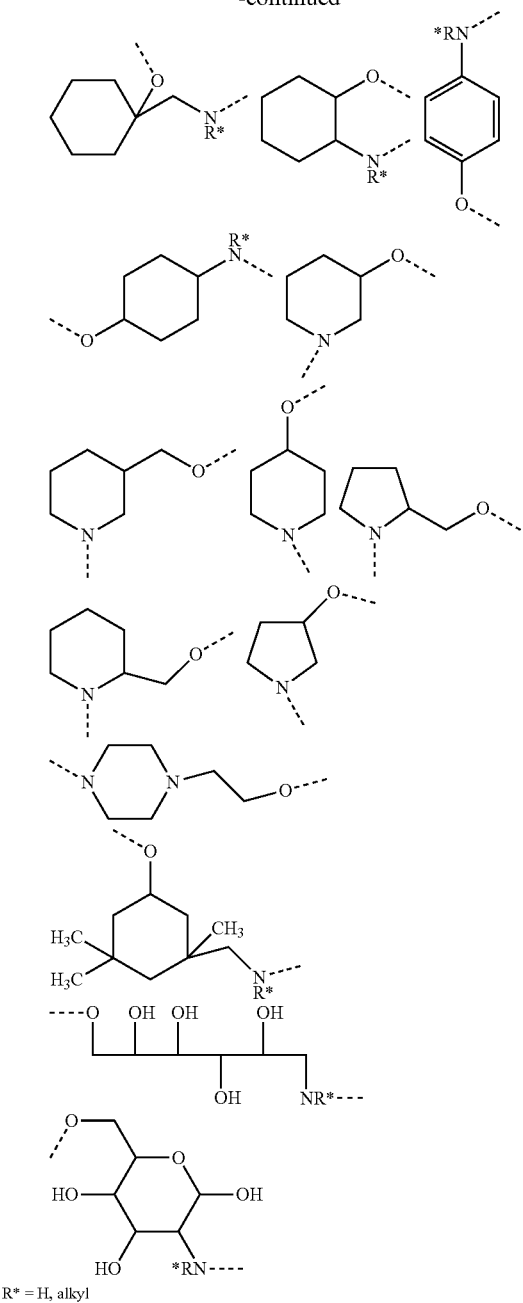

R* = H, alkyl

With continued reference to formulas (XVII) through (XXV) above, according to various non-limiting embodiments disclosed herein, -E- can represent a dicarboxylic acid residue or a derivative thereof, wherein a first carbonyl group of said dicarboxylic acid residue can form a bond with -G- or -D-, and a second carbonyl group of said dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. Specific non-limiting examples of dicarboxylic acid residues that can be used in conjunction with various non-limiting embodiments disclosed herein include the following:

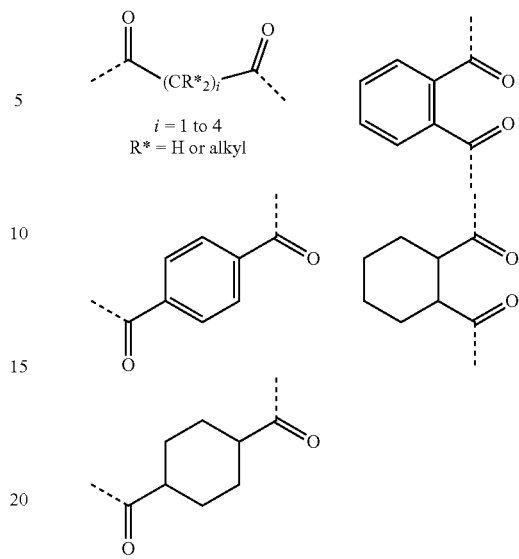

i = 1 to 4
R* = H or alkyl

According to various non-limiting embodiments disclosed herein, -G- can represent a group —[(OC$_2$H$_4$)$_x$(OC$_3$H$_6$)$_y$(OC$_4$H$_8$)$_z$]—O—, wherein x, y and z are each independently chosen and range from 0 to 50, and a sum of x, y, and z ranges from 1 to 50; a polyol residue or a derivative thereof, wherein a first polyol oxygen of said polyol residue can form a bond with -A'-, -D-, -E-, or a substituent or an available position on the indeno-fused naphthopyran, and a second polyol oxygen of said polyol can form a bond with -E- or -J; or a combination thereof, wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$(OC$_4$H$_8$)$_z$]—O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particularly, illustrative and non-limiting examples of polyols from which the polyol residues that -G- can represent can be formed according to various non-limiting embodiments disclosed herein include: (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XVII) through (XXV), according to various non-limiting embodiments disclosed herein, -J can represent a group —K, wherein —K represents a group such as, but not limited to, —$CH_2COOH$, —$CH(CH_3)COOH$, —$C(O)(CH_2)_wCOOH$, —$C_6H_4SO_3H$, —$C_5H_{10}SO_3H$, —$C_4H_8SO_3H$, —$C_3H_6SO_3H$, —$C_2H_4SO_3H$ and —$SO_3H$, wherein "w" ranges from 1 to 18. According to other non-limiting embodiments -J can represent hydrogen that forms a bond with an oxygen or a nitrogen of linking group to form a reactive moiety such as —OH or —NH. For example, according to various non-limiting embodiments disclosed herein, -J can represent hydrogen, provided that if -J represents hydrogen, -J is bonded to an oxygen of -D- or -G-, or a nitrogen of -D-.

According to still further non-limiting embodiments, -J can represent a group -L or residue thereof, wherein -L can represent a reactive moiety. For example, according to various non-limiting embodiments disclosed herein -L can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

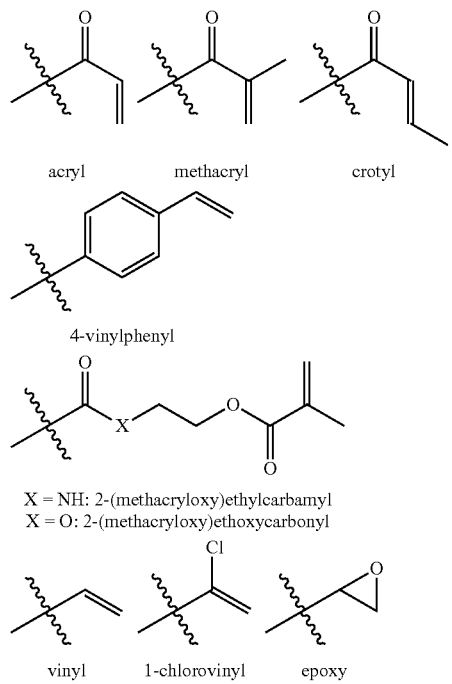

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by q-$(OH)_a$ and the residue of the polyol can be represented by the formula —O-q-$(OH)_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatibilizing substituent comprises the group -G-J, if -G- represents a polyol residue and -J represents a group —K that contains a carboxyl terminating group, -G-J can be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfa or sulfono terminating group, although not limiting herein, -G-J can be produced by acidic condensation of one or more of the polyol hydroxyl groups with $HOC_6H_4SO_3H$; $HOC_5H_{10}SO_3H$; $HOC_4H_8SO_3H$; $HOC_3H_6SO_3H$; $HOC_2H_4SO_3H$; or $H_2SO_4$, respectively. Further, although not limiting herein, if -G- represents a polyol residue and -J represents a group -L chosen from acryl, methacryl, 2-(methacryloxy)ethylcarbamyl and epoxy, -L can be added by condensation of the polyol residue with acryloyl chloride, methacryloyl chloride, 2-isocyanatoethyl methacrylate or epichlorohydrin, respectively.

As discussed previously herein, the compositions of the present invention, include the liquid crystal compositions of the present invention, in addition to a photochromic compound and/or a photochromic-dichroic compound, can further include a dichroic compound. Examples of dichroic compounds that can be included in the compositions of the present invention include, but are not limited to, the dichroic compounds described in U.S. Pat. No. 7,097,303 at column 7, lines 6 to 60. Further examples of dichroic compounds that can be used in the compositions of the present invention include azomethines, indigoids, thioindigoids, merocyanines, indans, quinophthalonic dyes, perylenes, phthaloperines, triphenodioxazines, indoloquinoxalines, imidazotriazines, tetrazines, azo and (poly)azo dyes, benzoquinones, naphthoquinones, anthroquinone and (poly)anthroquinones, anthropyrimidinones, iodine and iodates. The dichroic compounds can be in some embodiments selected from polymerizable dichroic compounds, that include at least one group that is capable of being polymerized. The polymerizable groups of the polymerizable dichroic compounds can be selected from those polymerizable groups as described previously herein with regard to the photochromic compounds, and in particular the indeno-fused naphthopyrans. As discussed previously herein, to ensure that a net linear polarization is obtained, the dichroic compounds, such as dichroic dyes, are typically aligned. A non-limiting example of an alignment facility that can be used for purposes of aligning dichroic compounds is described in U.S. Pat. No. 7,632,540 column 2, line 6 to column 28, line 24.

The compositions of the present invention can also include one or more photochromic-dichroic compounds. Examples of photochromic-dichroic compounds that can be included in the compositions of the present invention include, but are not limited to, those disclosed in U.S. Pat. No. 7,256,921 at column 19, line 3 to column 66, line 60; U.S. Patent Application Publication No. US 2009/0309076 at paragraphs [0029] to [0137]; and U.S. patent application Ser. Nos. 12/928,671, 12/928,681, and 12/928,687, each filed on Dec. 16, 2010. In addition, a general structure for photochromic-dichroic compounds is presented in U.S. Pat. No. 7,342,112 at column 5, line 35 to column 31, line 3 and Table V spanning columns 97-102.

The compositions of the present invention can include photochromic compounds and/or photochromic-dichroic compounds alone or in conjunction with other conventional organic photochromic compounds (as discussed above), in amounts or ratios such that the compositions into which the photochromic and/or photochromic-dichroic compounds are incorporated, exhibit a desired color or colors, either in an activated state (e.g., colored state) or an non-activated state (e.g., a bleached state). Thus the amount of the photochromic and/or photochromic-dichroic compounds used is not critical provided that a sufficient amount is present to produce a desired photochromic effect. As used herein, the term "photochromic amount" refers to the amount of the photochromic and/or photochromic-dichroic compound necessary to produce the desired photochromic effect.

The compositions and other articles according to various embodiments of the present invention can include any amount of the photochromic compound, dichroic compound and/or photochromic-dichroic compound necessary to achieve the desired optical properties, such as photochromic properties and dichroic properties.

The compositions, including liquid crystal compositions, of the present invention, can further include an additive selected from a liquid crystal, a liquid crystal property control agent, a non-linear optical material, a dye, an alignment promoter, a kinetic enhancer, a photoinitiator, a thermal initiator, a surfactant, a polymerization inhibitor, a solvent, a conventional light stabilizer (e.g., ultraviolet light absorbers and light stabilizers including hindered amine groups), a conventional thermal stabilizer, a mold release agent, a rheology control agent, a gelator, a leveling agent (e.g., a surfactant), a free radical scavenger, and/or an adhesion promoter/coupling agent (e.g., hexane diol diacrylate). The conventional light stabilizers and thermal stabilizers would be optionally used in addition to the compounds of the present invention represented by Formula I.

Liquid crystal materials that can be present in the compositions of the present invention, can be chosen from liquid crystal polymers, liquid crystal pre-polymers, and liquid crystal monomers. As used herein the term "pre-polymer" means partially polymerized materials, are capable of undergoing further polymerization or polymer chain extension.

Liquid crystal monomers that can be included in the compositions of the present invention include mono-functional and multi-functional liquid crystal monomers. With some embodiments, the liquid crystal monomer can be a cross-linkable liquid crystal monomer, and can further be a photo-cross-linkable liquid crystal monomer. As used herein the term "photocross-linkable" means a material, such as a monomer, a pre-polymer or a polymer, that undergoes crosslinking after exposure to actinic radiation.

Examples of cross-linkable liquid crystal monomers include, but are not limited to, liquid crystal monomers having functional groups chosen from acrylates, methacrylates, allyl, allyl ethers, alkynes, amino, anhydrides, epoxides, hydroxides, isocyanates, blocked isocyanates, siloxanes, thiocyanates, thiols, urea, vinyl, vinyl ethers and blends thereof. Examples of photocross-linkable liquid crystal monomers include, but are not limited to, liquid crystal monomers having functional groups chosen from acrylates, methacrylates, alkynes, epoxides, thiols, and blends thereof.

Liquid crystal polymers and pre-polymers that can be included in the compositions of the present invention include thermotropic liquid crystal polymers and pre-polymers, and lyotropic liquid crystal polymers and pre-polymers. Further, the liquid crystal polymers and pre-polymers can be main-chain polymers and pre-polymers or side-chain polymers and pre-polymers. Additionally, according to various embodiments of the present invention, the liquid crystal polymer or pre-polymer can be cross-linkable, and further can be photo-cross-linkable.

Examples of liquid crystal polymers and pre-polymers that can be included in the compositions of the present invention, include main-chain and side-chain polymers and pre-polymers having functional groups chosen from acrylates, methacrylates, allyl, allyl ethers, alkynes, amino, anhydrides, epoxides, hydroxides, isocyanates, blocked isocyanates, siloxanes, thiocyanates, thiols, urea, vinyl, vinyl ethers, and blends thereof. Examples of photocross-linkable liquid crystal polymers and pre-polymers that can be included in the compositions of the present invention include polymers and pre-polymers having functional groups chosen from acrylates, methacrylates, alkynes, epoxides, thiols, and blends thereof. The liquid crystal polymers and prepolymers can be selected from art-recognized polymers and prepolymers, such as, polyethers, polyesters, polyurethanes, polyacrylates, and combinations of two or more thereof.

Surfactants that can be included in the compositions of the present invention, include materials also referred to as wetting agents, anti-foaming agents, emulsifiers, dispersing agents, leveling agents etc. The surfactant can be selected from anionic surfactants, cationic surfactants, nonionic surfactants, and combinations thereof. Surfactants that can be included in the compositions and articles of the present invention, include art-recognized and commercially available surfactants. Examples of nonionic surfactants include, but are not limited to, ethoxylated alkyl phenols, such as the IGEPAL® DM surfactants or octyl-phenoxypolyethoxyethanol sold as TRITON® X-100, acetylenic diols such as 2,4,7, 9-tetramethyl-5-decyne-4,7-diol sold as SURFYNOL® 104, ethoxylated acetylenic diols, such as the SURFYNOL® 400 surfactant series, fluoro-surfactants, such as the FLUORAD® fluorochemical surfactant series, and capped nonionics such as the benzyl capped octyl phenol ethoxylates sold as TRITON® CF87, the propylene oxide capped alkyl ethoxylates, which are available as the PLURAFAC® RA series of surfactants, octylphenoxyhexadecylethoxy benzyl ether, polyether modified dimethylpolysiloxane copolymer in solvent sold as BYK®-306 additive by Byk Chemie and mixtures of such surfactants.

The compositions and articles of the present invention can optionally further include non-linear optical (NLO) materials. Non-linear optical materials include, but are not limited to, organic materials that exhibit non-linear optical properties and form crystals. Examples of non-linear optical materials include, but are not limited to: N-(4-nitrophenyl)-(L)-prolinol (NPP); 4-N,N-dimethylamino-4'-N'-methyl-stilbazolium tosylate (DAST); 2-methyl-4-nitroaniline (MNA); 2-amino-5-nitropyridine (2A5NP); p-chlorophenylurea (PCPU); and 4-(N,N-dimethylamino)-3-acetamidonitrobenzene (DAN). Further examples of non-linear optical materials include those disclosed in U.S. Pat. No. 6,941,051 at column 4, lines 4-37.

Examples of thermal stabilizers that can be included in the compositions and articles of the present invention include basic nitrogen-containing compounds, such as, biurea, allantoin or a metal salt thereof, a carboxylic acid hydrazide (e.g., an aliphatic or aromatic carboxylic acid hydrazide), a metal salt of an organic carboxylic acid, an alkali or alkaline earth metal compound, a hydrotalcite, a zeolite and an acidic compound (e.g., a boric acid compound, a nitrogen-containing cyclic compound having a hydroxyl group, a carboxyl group-containing compound, a (poly)phenol, butylated hydroxytoluene, and an aminocarboxylic acid) or mixtures thereof.

Examples of mold release agents that can be included or used in conjunction with the compositions and articles of the present invention include, but are not limited to, esters of long-chain aliphatic acids and alcohols such as pentaerythritol, guerbet alcohols, long-chain ketones, siloxanes, alpha.-olefin polymers, long-chain alkanes and hydrocarbons having 15 to 600 carbon atoms.

Rheology control agents that can be used with the compositions of the present invention can also be referred to as thickeners, and include, but are not limited to powders (or particulate materials), such as inorganic particulate materials (e.g., silica), and organic particulate materials, such as microcrystalline cellulose or particulate polymeric materials.

Gelators (or gelling agents) that can be included in the compositions of the present invention, include, but are not limited to, organic materials that can also affect the thixotropy of the composition into which they are incorporate. Examples of gelators include, but are not limited to, natural gums, starches, pectins, agar-agar, and gelatins. Gelators that can be used in the present invention include materials based on polysaccharides or proteins.

The compositions of the present invention can include free radical scavengers, examples of which include, but are not limited to: synthetic pseudopeptides resistant to hydrolysis, such as Carcinine hydrochloride; lipoamino acids, such as L-lysine lauroylmethionine; plant extracts containing multi-enzymes; natural tocopherol and related compounds, as well as compounds containing an active hydrogen such as —OH, —SH, or —NRH group, where R is a hydocarbyl group. Further examples of free radical scavengers include, but are not limited to, sterically hindered amines.

Adhesion promoters that can be included in the compositions and articles of the present invention include organosilane compounds, such as aminoorganosilane materials, silane coupling agents, organic titanate coupling agents and organic zirconate coupling agents described in U.S. Pat. No. 7,410,691 at column 6, line 12 to column 8, line 23. Further examples of adhesion promoters include zirco-aluminate adhesion promoting compounds that are commercially available from Rhone-Poulenc. Preparation of aluminum-zirconium complexes is described in the U.S. Pat. Nos. 4,539,048 and 4,539,049. These patents describe zirco-aluminate complex reaction products represented by the empirical formula:

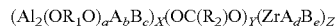

$(Al_2(OR_1O)_a A_b B_c)_X (OC(R_2)O)_Y (ZrA_d B_e)_Z$ wherein X, Y, and Z are at least 1, $R_2$ is an alkyl, alkenyl, aminoalkyl, carboxyalkyl, mercaptoalkyl, or epoxyalkyl group, having from 2 to 17 carbon atoms, and the ratio of X:Z is from about 2:1 to about 5:1. Additional zirco-aluminate complexes are described in U.S. Pat. No. 4,650,526.

Examples of dyes that can be present in the compositions and articles of the present invention include, but are not limited to, organic dyes that are capable of imparting a desired color or other optical property to the composition and/or article.

The compositions of the present invention can optionally include one or more alignment promoters. Alignment promoters include materials that are capable of facilitating the rate of alignment and/or uniformity of alignment, of a material to which it is added. Examples of alignment promoters include, but are not limited to, those described in U.S. Pat. No. 6,338,808 and U.S. Pat. No. 6,875,483.

Kinetic enhancing additives can also optionally be included in the compositions of the present invention. Examples of kinetic enhancing additives include, but are not limited to, epoxy-containing compounds, organic polyols, and/or plasticizers. More specific examples of kinetic enhancing additives are disclosed in U.S. Pat. No. 6,433,043 and U.S. Pat. No. 6,713,536.

Examples of photoinitiators that can be present in the compositions of the present invention include, but are not limited to, cleavage-type photoinitiators and abstraction-type photoinitiators. Examples of cleavage-type photoinitiators include, but are not limited to, acetophenones, α-aminoalkylphenones, benzoin ethers, benzoyl oximes, acylphosphine oxides and bisacylphosphine oxides or mixtures of such initiators. A commercial example of a cleavage-type photoinitiator is DAROCURE® 4265 photoinitiator, which is available from Ciba Chemicals, Inc. Examples of abstraction-type photoinitiators include, but are not limited to, benzophenone, Michler's ketone, thioxanthone, anthraquinone, camphorquinone, fluorone, ketocoumarin or mixtures of such photoinitiators.

Photoinitiators that can be present in the compositions of the present invention, also include visible light photoinitiators. Examples of suitable visible light photoinitiators are described at column 12, line 11 to column 13, line 21 of U.S. Pat. No. 6,602,603.

The compositions of the present invention can optionally include one or more thermal initiators. Examples of thermal initiators include, but are not limited to, organic peroxy compounds and azobis(organonitrile) compounds. Examples of organic peroxy compounds include, but are not limited to, peroxymonocarbonate esters, such as tertiarybutylperoxy isopropyl carbonate; peroxydicarbonate esters, such as di(2-ethylhexyl)peroxydicarbonate, di(secondary butyl)peroxydicarbonate and diisopropylperoxydicarbonate; diacyperoxides, such as 2,4-dichlorobenzoyl peroxide, isobutyryl peroxide, decanoyl peroxide, lauroyl peroxide, propionyl peroxide, acetyl peroxide, benzoyl peroxide and p-chlorobenzoyl peroxide; peroxyesters such as t-butylperoxy pivalate, t-butylperoxy octylate and t-butylperoxyisobutyrate; methylethylketone peroxide, and acetylcyclohexane sulfonyl peroxide. With some embodiments, the thermal initiators used include those that do not discolor the resulting polymerizate. Examples of azobis(organonitrile) compounds include, but are not limited to, azobis(isobutyronitrile), azobis(2,4-dimethylvaleronitrile) and mixtures thereof.

The compositions of the present invention can optionally include one or more polymerization inhibitors. Examples of polymerization inhibitors include, but are not limited to: nitrobenzene, 1,3,5,-trinitrobenzene, p-benzoquinone, chloranil, DPPH, $FeCl_3$, $CuCl_2$, oxygen, sulfur, aniline, phenol, p-dihydroxybenzene, 1,2,3-trihydroxybenzene, and 2,4,6-trimethylphenol.

The compositions of the present invention can optionally include one or more solvents. Solvents that can be present in the compositions of the present invention include solvents: that are capable of dissolving solid components of the compositions; that are compatible with the compositions, optical elements and/or substrates; and/or that can ensure uniform coverage of surfaces to which the composition is applied. Examples of solvents include, but are not limited to: propylene glycol monomethyl ether acetate and their derivates (sold as DOWANOL® industrial solvents), acetone, amyl propionate, anisole, benzene, butyl acetate, cyclohexane, dialkyl ethers of ethylene glycol, e.g., diethylene glycol dimethyl ether and their derivates (sold as CELLOSOLVE® industrial solvents), diethylene glycol dibenzoate, dimethyl sulfoxide, dimethyl formamide, dimethoxybenzene, ethyl acetate, isopropyl alcohol, methyl cyclohexanone, cyclopentanone, methyl ethyl ketone, methyl isobutyl ketone, methyl propionate, propylene carbonate, tetrahydrofuran, toluene, xylene, 2-methoxyethyl ether, 3-propylene glycol methyl ether, and mixtures thereof.

The compounds and compositions of the present invention can be incorporated into an organic host material. Examples of organic host materials include synthetic and natural polymer materials. Organic host materials into which the compounds and compositions of the present invention can be incorporated include, but are not limited to, those materials described further herein with regard to the substrates of the articles of the present invention.

The present invention also relates to an article of manufacture that includes one or more compounds according to the present invention represented by Formula I. Articles of manufacture according to the present invention can have one or more compounds represented by Formula I: incorporated directly therein, for example, prior to forming the article by molding; or applied to at least a portion of a surface of the article in the form of, one or more coatings that can optionally be cured or imbibed into the surface of the article, and/or a film, such as one or more laminated films.

With some embodiments of the present invention, the article of manufacture is an optical element that includes: (i) a substrate; and (ii) a layer on at least a portion of a surface of the substrate, in which the layer includes at least one compound of the present invention represented by Formula I. The layer can be selected from one or more coating compositions, one or more films (such as laminated films), and combinations thereof.

Substrates that can be used with the articles according to the present invention, include substrates formed from organic materials, inorganic materials, or combinations thereof (for example, composite materials).

Examples of organic materials that can be used as substrates of the articles according to the present invention, include polymeric materials, such as homopolymers and copolymers, prepared from the monomers and mixtures of monomers disclosed in U.S. Pat. No. 5,962,617 and in U.S. Pat. No. 5,658,501 from column 15, line 28 to column 16, line 17. For example, such polymeric materials can be thermoplastic or thermoset polymeric materials, can be transparent or optically clear, and can have any refractive index required. Examples of such monomers and polymers include: polyol (allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol)bismethacrylate monomers; urethane acrylate monomers; poly(ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly (ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products.

With some embodiments of the present invention, the substrate can be an ophthalmic substrate. As used herein the term "ophthalmic substrate" means lenses, partially formed lenses, and lens blanks. Examples of organic materials suitable for use in forming ophthalmic substrates include art-recognized polymers that are useful as ophthalmic substrates, e.g., organic optical resins that are used to prepare optically clear castings for optical applications, such as ophthalmic lenses.

Examples of additional organic materials suitable for use as substrates according to various embodiments of the present invention include natural and synthetic textiles, and cellulosic materials such as, paper and wood.

Examples of inorganic materials that can be used as substrates with the articles of the present invention include glasses, minerals, ceramics, and metals. With some embodiments, the substrate can comprise glass. In other embodiments, the substrate can have a reflective surface, for example, a polished ceramic substrate, metal substrate, or mineral substrate. In other embodiments, a reflective coating or layer (e.g., a metal layer, such as a silver layer) can be deposited or otherwise applied to a surface of an inorganic or an organic substrate to make it reflective or to enhance its reflectivity.

In accordance with some embodiments of the present invention, the substrates can have a protective coating, for example, an abrasion-resistant coating, such as a "hard coat," on an exterior surface thereof. For purposes of illustration, commercially available thermoplastic polycarbonate ophthalmic lens substrates are often sold with an abrasion-resistant coating already applied to its exterior surfaces because these surfaces tend to be readily scratched, abraded or scuffed. Correspondingly, as used herein the term "substrate" includes a substrate having a protective coating, such as an abrasion-resistant coating, on its surface(s).

Substrates that can be used with articles according to the present invention also include untinted, tinted, linearly polarizing, circularly polarizing, elliptically polarizing, photochromic, or tinted-photochromic substrates. As used herein with reference to substrates the term "untinted" means substrates that are essentially free of coloring agent additions (such as conventional dyes) and have an absorption spectrum for visible radiation that does not vary significantly in response to actinic radiation. Further, with reference to substrates the term "tinted" means substrates that have a coloring agent addition (such as conventional dyes) and an absorption spectrum for visible radiation that does not vary significantly in response to actinic radiation.

As used herein, the term "linearly polarizing" with reference to substrates refers to substrates that are adapted to linearly polarize radiation (i.e., confine the vibrations of the electric vector of light waves to one direction). As used herein, the term "circularly polarizing" with reference to substrates refers to substrates that are adapted to circularly polarize radiation. As used herein, the term "elliptically polarizing" with reference to substrates refers to substrates that are adapted to elliptically polarize radiation. Further, as used herein, with reference to substrates, the term "tinted-photochromic" means substrates containing a coloring agent addition as well as a photochromic material, and having an absorption spectrum for visible radiation that varies in response to at least actinic radiation. Thus, for example, the tinted-photochromic substrate can have a first color characteristic of the coloring agent and a second color characteristic of the combination of the coloring agent the photochromic material when exposed to actinic radiation.

With some embodiments of the present invention, the layer of the article of the present invention is at least partially aligned by exposing at least a portion of said layer to at least one of a magnetic field, an electric field, linearly polarized radiation, and shear force. As used herein the term "aligned" means to bring into suitable arrangement or position by interaction with another material, compound and/or structure. With some embodiments, at least partial alignment of the layer results in a net linear polarization of transmitted radiation relative to the layer. Additional methods of aligning the layer include, but are not limited to, exposing the layer to plane-polarized ultraviolet radiation, exposing the layer to infrared radiation, etching the layer, rubbing the layer, and aligning the layer with another structure or material, such as an at least partially ordered alignment medium. Examples of alignment methods for layers are described in greater detail in U.S. Pat. No. 7,097,303, at column 27, line 17 to column 28, line 45.

With some embodiments of the present invention, the layer of the articles and optical elements of the present invention includes a liquid crystal phase having at least one of a nematic phase, a smectic phase, or a chiral nematic phase.

The layer including the compound of the present invention, that is present on at least a portion of a surface of the substrate, can be selected from those compositions according to the present invention as described previously herein. The layer can be in the form of a curable coating, a thermoplastic coating, a laminated thermoset film, and/or a laminated thermoplastic film. The layer can be applied by art-recognized methods, such as, but not limited to, spin coating, spray coating, spray and spin coating, curtain coating, flow coating, dip coating, injection molding, casting, roll coating, wire coating, and overmolding. The coating including the compound of the present invention can be applied to an interior surface of a mold and the substrate can be formed on (e.g., on top of) the coating (i.e., overmolding).

Non-limiting examples of coating compositions of film forming polymers that can include the compounds of the present invention are as follows: those described in U.S. Pat. No. 7,256,921 at column 2, line 60 to column 94, line 23; polyurethane coatings, such as those described in U.S. Pat. No. 6,187,444 at column 3, line 4 to column 12, line 15; aminoplast resin coatings, such as those described in U.S. Pat. No. 6,432,544 at column 2, line 52 to column 14, line 5 and U.S. Pat. No. 6,506,488 at column 2, line 43 to column 12, line 23; polysiloxane coatings, such as those described in U.S. Pat. No. 4,556,605 at column 2, line 15 to column 7, line 27; poly(meth)acrylate coatings, such as those described in U.S. Pat. No. 6,602,603 at column 3, line 15 to column 7, line 50, U.S. Pat. No. 6,150,430 at column 8, lines 15-38, and U.S. Pat. No. 6,025,026 at column 8, line 66 to column 10, line 32; polyanhydride coatings, such as those described in U.S. Pat. No. 6,436,525 at column 2, line 52 to column 11, line 60; polyacrylamide coatings such as those described in U.S. Pat. No. 6,060,001 at column 2, line 6 to column 5, line 40; epoxy resin coatings, such as those described in U.S. Pat. No. 6,268,055 at column 2, line 63 to column 15, line 12; and poly(urea-urethane) coatings, such as those described in U.S. Pat. No. 6,531,076 at column 2, line 60 to column 10, line 49. The disclosures in the aforementioned U.S. patents that relate to the film-forming polymers are hereby incorporated herein by reference.

Non-limiting methods of applying films and sheets including the compounds of the present invention to a substrate include, for example, at least one of: laminating, fusing, in-mold casting, and adhesively bonding the polymeric sheet to the at least a portion of the substrate. As used herein, in-mold casting includes a variety of casting techniques, such as but not limited to: overmolding, wherein the sheet is placed in a mold and the substrate is formed (for example by casting) over at least a portion of the substrate; and injection molding, wherein the substrate is formed around the sheet.

The polymeric film or sheet can include a polymeric composition of any of a wide variety of polymers, including both thermosetting polymers and thermoplastic polymers. As used herein, the term "polymer" is intended to include both polymers and oligomers, as well as both homopolymers and copolymers. Such polymers can include, for example, acrylic polymers, polyester polymers, polyurethane polymers, poly(urea)urethane polymers, polyamine polymers, polyepoxide polymers, polyamide polymers, polyether polymers, polysiloxane polymers, polysulfide polymers, copolymers thereof, and mixtures thereof. Generally these polymers can be any polymers of these types made by any method known to those skilled in the art.

The polymers used to form the polymeric film or sheet also can include functional groups including, but not limited to, carboxylic acid groups, amine groups, epoxide groups, hydroxyl groups, thiol groups, carbamate groups, amide groups, urea groups, isocyanate groups (including blocked isocyanate groups) mercaptan groups, groups having ethylenic unsaturation e.g., acrylate groups), vinyl groups, and combinations thereof. Appropriate mixtures of film-forming resins can also be used in the preparation of the coating compositions. If the polymer composition from which the polymeric sheet is formed includes functional group-containing polymers (such as any of the previously mentioned functional group-containing polymers), the polymer composition can further include a material having functional groups reactive with those of said polymer. Reaction can be facilitated, for example, by thermal, photoinitiated, oxidative, and/or radiative curing techniques. Also contemplated are mixtures of any of the foregoing polymers.

Further non-limiting examples of polymers suitable for use in forming the polymeric film or sheet of the present invention include thermoplastic block copolymers of polyalkyl(meth)acrylate and polyamide described in Published U.S. Pat. No. 7,282,551 at column 4, line 24 to column 9, line 17, the specified portions of which are incorporated by reference herein; and U.S. Pat. No. 6,096,375 at column 18, line 8 to column 19, line 5, the specified portions of which are incorporated by reference herein.

In a particular embodiment of the present invention, the polymeric film or sheet includes an elastomeric polymer, for example thermoplastic elastomeric polymers. As used herein, by "elastomeric polymer" is meant a polymer that has a high degree of resiliency and elasticity such that it is capable of at least partially reversible deformation or elongation. In some instances, when stretched, the molecules of an elastomer are aligned and can take on aspects of a crystalline arrangement;

and upon release, the elastomer can, to some extent, return to its natural disordered state. For purposes of the present invention, elastomeric polymers can include thermoplastic, thermoplastic elastomeric polymers, and thermosetting polymers provided such polymers fall within the description provided above for "elastomeric polymer."

The elastomeric polymer can include any of wide variety of art recognized elastomers including but not limited to copolymers of any of the previously mentioned polymers. In an embodiment of the present invention, the elastomeric polymer can include a block copolymer having ether and/or ester linkages in the polymer backbone. Examples of suitable block copolymers can include, but are not limited to, poly(amide-ether) block copolymers, poly(ester-ether) block copolymers, poly(ether-urethane) block copolymers, poly(ester-urethane) block copolymers, and/or poly(ether-urea) block copolymers. Suitable specific examples of such elastomeric polymers can include, but are not limited to, those commercially available under the tradenames DESMOPAN® and TEXIN® from Bayer Material Science; ARNITEL® from Royal DSM; and PEBAX® from Atofina Chemicals or Cordis Corporation.

Curing the compositions and/or layers that include the compound of the present invention can include at least partially polymerizing the composition or layer. Methods for at least partially polymerizing the composition/layer include exposing at least a portion of the composition/layer to at least one of thermal energy (for example to activate a thermal initiator), infrared radiation, ultraviolet radiation, visible radiation, gamma radiation, microwave radiation, electron radiation or combinations thereof so as to initiate the polymerization reaction of the polymerizable components or cross-linking with or without a catalyst or initiator. If desired or required, this can be followed by a heating step. According to some embodiments, the composition/layer can be cured to a specific or target surface hardness. For example, with some embodiments, the composition/layer can be cured to have a Fischer microhardness ranging from 0 to 150 Newtons/mm$^2$ that also exhibits good photochromic and/or dichroic response characteristics. With other embodiments, the composition/layer can be cured to a Fischer microhardness of less than 60 Newtons/mm$^2$, e.g. from 0 to 59.9 Newtons/mm$^2$, or alternatively from 5 to 25 N/mm$^2$. With additional embodiments, the composition/layer can be cured to have a Fischer microhardness ranging from 150 N/mm$^2$ to 250 N/mm$^2$ or alternatively from 150 N/mm$^2$ to 200 N/mm$^2$.

In accordance with further embodiments of the present invention, the optical element of the present invention is selected from an ophthalmic element, a display element, a window, a mirror, and a liquid crystal cell element. As used herein the term "optical" means pertaining to or associated with light and/or vision. The optical element or device can also be chosen from ophthalmic elements and devices, display elements and devices, windows, mirrors, packaging material such as shrinkwrap, and active and passive liquid crystal cell elements and devices.

As used herein the term "ophthalmic" means pertaining to or associated with the eye and vision. Non-limiting examples of ophthalmic elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intraocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, including without limitation, security marks and authentication marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

With some embodiments, the optical element can be a security element. Examples of security elements include, but are not limited to, security marks and authentication marks that are connected to at least a portion of a substrate, such as: access cards and passes, e.g., tickets, badges, identification or membership cards, debit cards, etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

With further embodiments, the security element can be connected to at least a portion of a substrate chosen from a transparent substrate and a reflective substrate. Alternatively, according to further embodiments in which a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Additionally or alternatively, the security element can be connected to at least a portion of a substrate chosen from untinted substrates, tinted substrates, photochromic substrates, tinted-photochromic substrates, linearly polarizing, circularly polarizing substrates, and elliptically polarizing substrates.

Furthermore, security elements according to the aforementioned embodiments can further include one or more other coatings or films or sheets to form a multi-layer reflective security element with viewing angle dependent characteristics, such as described in U.S. Pat. No. 6,641,874.

With some embodiments, the article of manufacture according to the present invention is a liquid crystal cell that includes: (i) a first substrate having a first surface; (ii) a second substrate having a second surface, said first surface of said first substrate and said second surface of said second substrate being in spaced opposition from each other, and together defining a space there-between; and (iii) a liquid crystal composition residing within at least a portion of said space, said liquid crystal composition comprising the compound of the present invention represented by Formula I. The first and second substrates of the liquid crystal cell can each be independently selected from those classes and examples of substrates as described previously herein with regard to the optical element of the present invention.

As used herein the term "liquid crystal cell" refers to a structure containing a liquid crystal material that is capable of being ordered. Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. A non-limiting example of an active liquid crystal cell element or device is a liquid crystal display.

The present invention also relates to a method of forming an ophthalmic element, that includes: (i) forming a liquid crystal composition comprising the compound of the present invention represented by Formula I; (ii) applying the liquid crystal composition to at least a portion of a substrate; (iii) at least partially aligning at least a portion of the liquid crystal composition applied to the substrate, thereby forming an at least partially aligned liquid crystal composition; and (iv) curing, at least partially, the aligned liquid crystal composition.

The liquid crystal composition can be selected from those liquid crystal compositions as described previously herein. The substrate can be selected from those substrates as described previously herein. Application of the liquid crystal composition to the substrate can be conducted in accordance with those application methods described previously herein. Aligning the liquid crystal composition can be achieved in accordance with those methods as described previously herein. The aligned liquid crystal composition can be cured in accordance with those methods as described previously herein, such as by exposure to actinic radiation, high energy particles (e.g., electron beam) and/or elevated temperature. The term "at least partially cured" means the curable or crosslinkable components of the liquid crystal composition are at least partially cured, crosslinked and/or reacted. In alternate non-limiting embodiments, the degree of reacted components, can vary widely, e.g., from 5% to 100% of all the possible curable, crosslinkable and/or reactable components.

The present invention is more particularly described in the following examples, which are intended to be illustrative only, since numerous modifications and variations therein will be apparent to those skilled in the art. Unless otherwise specified, all parts and all percentages are by weight.

EXAMPLES

Part 1 describes the preparation of Examples 1-14. Part 2 describes the liquid crystal coating components and formulations. Part 3 describes the preparation of the photoalignment coating solution. Part 4 describes the preparation of the transitional layer coating formulation. Part 5 describes the procedures used for preparing and coating the substrates. Part 6 describes the measurements made to determine the clearing temperature upon heating and cooling reported in Table 2 and the photochromic performance test results including absorbance ratios, optical response and fatigue reported in Tables 3, 4 and 5.

Part 1—Preparation of Examples

Example 1

Step 1

To a reaction flask containing 2000 mL of N,N-dimethylacetamide was added methyl 4-hydroxy benzoate (609 g, 4 mol), 6-chloro-1-hexanol (656 g, 4.8 mol), sodium iodide hydrate (74.4 g, 0.4 mol), and sodium carbonate anhydrous (848 g, 8 mol). The resulting suspension was stirred and heated to about 115° C. for 8 hours. The solution was cooled to room temperature and filtered. The recovered solid was washed with 500 mL of N,N-dimethylacetamide. The filtrate was concentrated under reduced pressure and the resulting residue was poured into 10 L of distilled water under stirring. A white solid was obtained after filtration followed by rinsing with distilled water. The product was used for next step without further purification.

Step 2

To a reaction flask containing the product from Step 1 was added sodium hydroxide (192 g, 4.8 mol), water (768 mL), and ethanol (2000 mL). The resulting suspension was heated to reflux for 30 minutes. The solution was cooled to 65° C. and acidified by the addition of 912 mL of 10 weight % hydrochloric acid solution to adjust pH to 4. A large amount of white solid formed. The solid was filtered and washed with water and dried to give 892 g of product. The product was recovered as a white solid. Nuclear Magnetic Resonance (NMR) showed that the product had a structure consistent with 4-((6-hydroxyhexyl)oxy)benzoic acid. This material was scaled up using same procedures from Step 1 and Step 2 so that enough material was available for Step 3.

Step 3

To a reaction flask containing 6500 mL of tetrahydrofuran (THF) was added the product of Step 2 (2.14 Kg, 9.00 mol) and p-toluenesulfonic acid (17.13 g, 0.09 mol). The resulting suspension was stirred at room temperature and dihydropyran (984 ml, 10.80 mol) was added dropwise within a one hour interval. The reaction mixture was heated to 50° C. After stirring for 24 hours at this temperature, dihydropyran (654 ml, 7.17 mol) was added dropwise within a one hour interval and the reaction mixture was stirred for 24 hours. The solution was cooled to room temperature and filtered through CELITE® filter aid, and the filtrate was concentrated. The recovered product was dissolved in 9000 ml of methylene chloride and filtered through CELITE® filter aid, and the filtrate was concentrated and poured into 9000 ml of petroleum ether. The precipitate that formed was collected by filtration. The recovered product was purified by recrystallization in petroleum ether and dried in vacuum to give the product (1.70 Kg) as a white solid. Nuclear Magnetic Resonance (NMR) showed that the product had a structure consistent with 4-((6-((tetrahydro-2H-pyran-2-yl)oxy)hexyl)oxy)benzoic acid.

Step 4

To a reaction flask containing 200 mL of methylene chloride was added 2-methylhydroquinone (5.0 g, 40.3 mmol), the product from Step 3 (26.62 g, 82.6 mmol), dicyclohexylcarbodiimide (18.28 g, 88.6 mmol), and 4-dimethylaminopyridine (1.97 g, 16.1 mmol). The resulting mixture was stirred at room temperature under nitrogen atmosphere overnight. The white precipitate that formed during the reaction was discarded by filtration through a Buchner funnel. Evaporation of the solvent yielded the product, in a form of viscous material, which was used directly for the next step without further purification.

Step 5

To a reaction flask containing 500 mL of methanol was added the product from Step 4 and p-toluenesulfonic acid (1.57 g, 8.26 mmol). The resulting mixture was heated to gently reflux for 4 hours. The resulting solution was cooled in a dry-ice/acetone bath and a large amount of white precipitate formed. The white precipitate was collected by filtration and dried under vacuum to yield the product (17.2 g). Nuclear Magnetic Resonance (NMR) showed that the product had a structure consistent with 2-methyl-1,4-phenylene bis(4-((6-hydroxyhexyl)oxy)benzoate).

Step 6

To a reaction flask containing 200 mL of toluene was added the product from Step 5 (5.0 g, 8.9 mmol), succinic anhydride (1.83 g, 18.2 mmol) and 4-dimethylaminopyridine (0.11 g, 0.9 mmol). The resulting mixture was heated to reflux overnight under a nitrogen atmosphere. The resulting solution was allowed to cool to room temperature and a large amount of white precipitate formed, which was collected by filtration. The recovered product was used directly for the next step without purification. Nuclear Magnetic Resonance (NMR) showed that the product had a structure consistent with 4,4'-(((((((2-methyl-1,4-phenylene)bis(oxy))bis(carbonyl))bis(4,1-phenylene))bis(oxy))bis(hexane-6,1-diyl))bis(oxy))bis(4-oxobutanoic acid).

Step 7

The procedure of Step 4 was followed except that the product from Step 6 and 1,2,2,6,6-pentamethylpiperidin-4-ol were used in place of 4'4-(6-(tetrahydro-2H-pyran-2-yloxy)hexyloxy)-benzoic acid and 2-methylhydroquinone. The resulting product was purified by column chromatography on silica gel eluting with hexane/ethyl acetate (50/50, v/v) plus 5 v % triethylamine produced the final product in a form of liquid (2.4 g). Nuclear Magnetic Resonance (NMR) showed that the product had a structure consistent with 1,2,2,6,6-pentamethyl-4-((4-((6-(4-((3-methyl-4-((4-((6-((4-oxo-4-((1,2,2,6,6-pentamethylpiperidin-4-yl)oxy)butanoyl)oxy)hexyl)oxy)benzoyl)oxy)phenoxy)carbonyl)phenoxy)hexyl)oxy)-4-oxobutanoyl)oxy)piperidine as represented by the following graphic formula.

Step 3

The procedures of Steps 1 to 4 of Example 1 were followed except that one equivalent of 4-(benzyloxy)phenol was used in place of 0.5 equivalent of methyl hydroquinone in Step 4. At Step 4, after the filtration, the filtrate was poured into methanol under stirring. After overnight, the solid was collected by filtration, rinsed with methanol and dried. The product was used directly for the next step without further purification. A white solid was recovered as the product. This material was scaled up using same procedures from Step 1 to Step 3 so that enough material was available for Step 4.

Step 4

To a reaction flask containing 2.5 L of tetrahydrofuran was added the product from Step 3 (756.9 g, 1.5 mol) and 10% Pd/C (Palladium on Carbon) (20.00 g). The resulting mixture was hydrogenated up to 50 atm hydrogen pressure at room temperature for 24 hours. The resulting mixture was filtered through CELITE® filter aid, and concentrated. The residue was poured into petroleum ether (3.0 L) under stirring and the resulting mixture was stirred for another hour. Filtration through a Buchner funnel and drying in vacuum yielded the final product (540.00 g). A white solid was recovered as the product. Nuclear Magnetic Resonance (NMR) showed that

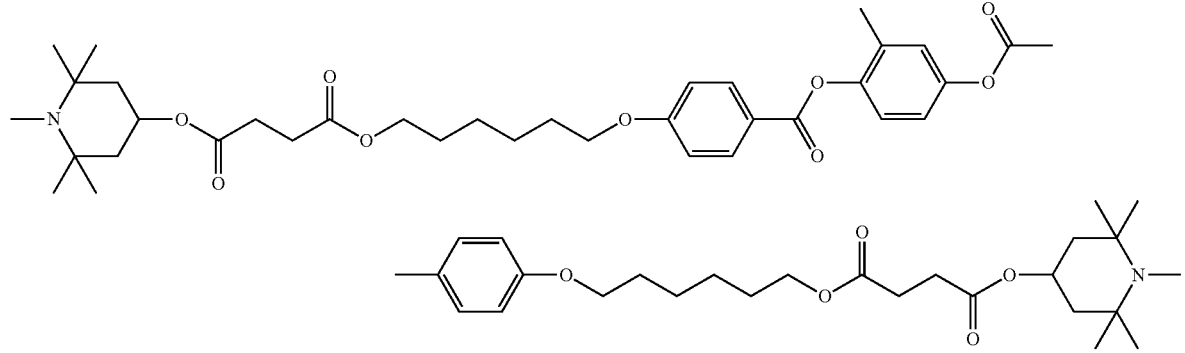

Example 2

Step 1

The procedures of Steps 1 and 2 of Example 1 were followed except that 3-chloro-1-propanol and methyl 4-(3-hydroxypropoxy)benzoate were used in place of 6-chloro-1-hexanol in Step 1 and methyl 4-(6-hydroxyhexoxy)benzoate in Step 2. A white solid was recovered as the product. Nuclear Magnetic Resonance (NMR) showed that the product had a structure consistent with 4-(3-hydroxypropoxy)benzoic acid.

Step 2

To a reaction flask containing 100 mL of chloroform was added the product from Step 1 (9.81 g, 50.0 mmol), acrylic acid (31.5 g, 437.6 mmol), hydroquinone (2.0 g, 18.2 mmol) and p-toluenesulfonic acid (2.0 g, 10.5 mmol). The resulting mixture was refluxed for 6 hours using a Dean-Stark apparatus. The resulting solution was allowed to cool down to room temperature and diluted with a 3 to 4-fold excess of ether, washed with warm water (50° C.) (100 mL×2) and dried over anhydrous magnesium sulfate. After evaporation of the solvent, the recovered product was recrystallized from isopropanol to yield the final product (9.4 g) in a form of white solid. Magnetic Resonance (NMR) showed that the product had a structure consistent with 4-(3-(acryloyloxy)propoxy)benzoic acid.

the product had a structure consistent with 4-hydroxyphenyl 4-((6-((tetrahydro-2H-pyran-2-yl)oxy)hexyl)oxy)benzoate.

Step 5

The procedure of Step 4 of Example 1 was followed except that the product from Step 2 and the product from Step 4 with a molar ratio of 1/1 were used in place of 4-((6-((tetrahydro-2H-pyran-2-yl)oxy)hexyl)oxy)benzoic acid and 2-methylhydroquinone. After filtration, the filtrate was concentrated and poured into methanol with stirring for two hours. The solid was collected by filtration, rinsed with methanol, and dried. The product was used directly for the next step without further purification. A white solid was recovered as the product.

Step 6

To a reaction flask containing 3.00 L of tetrahydrofuran and 2.00 L of methanol was added the product from Step 5 and 2,6-di-tetra-butyl-4-methylphenol and p-toluene sulfonic acid (20.00 g). The solution was stirred for 15 hours at room temperature and concentrated under reduced pressure. The resulting residue was poured into methanol (3.00 L) with stirring. A white solid was collected by filtration. After drying, 405 g of the final product in a form of white solid was yielded. Nuclear Magnetic Resonance (NMR) showed that the product had a structure consistent with 4-((4-(3-(acryloyloxy)propoxy)benzoyl)oxy)phenyl 4-((6-hydroxyhexyl)oxy)benzoate.

Step 7

To a reaction flask containing 1.00 L of toluene was added 1,2,2,6,6-pentamethylpiperidin-4-ol (239.62 g, 1.40 mol), succinic anhydride (140.00 g, 1.40 mol), and 4-(dimethylamino)pyridine. The mixture was heated to reflux for overnight under a nitrogen atmosphere. The resulting solution was concentrated to a minimum amount and 1500 mL of hexane was poured in. A large amount of white solid formed and collected by filtration. The final product was yielded after drying in vacuum (370.7 g). A white solid was recovered as the product. Nuclear Magnetic Resonance (NMR) showed that the product had a structure consistent with 4-oxo-4-((1,2,2,6,6-pentamethylpiperidin-4-yl)oxy)butanoic acid.

Step 8

The procedure of Step 4 of Example 1 was followed except that the product from Step 7 and the product from Step 6 with a molar ratio of 1/1 were used in place of 4-((6-((tetrahydro-2H-pyran-2-yl)oxy)hexyl)oxy)benzoic acid and 2-methylhydroquinone. The product was further purified by column chromatography on silica gel eluting with hexane/ethyl acetate (70/30, v/v) followed by dichloromethane. A white solid was recovered as the product (3.1 g). Nuclear Magnetic Resonance (NMR) showed that the product had a structure consistent with 4-((4-((6-(4-((4-((4-(3-(acryloyloxy)propoxy)benzoyl)oxy)phenoxy)carbonyl)phenoxy)hexyl)oxy)-4-oxobutanoyl)oxy)-1,2,2,6,6-pentamethylpiperidine as represented by the following graphic formula.

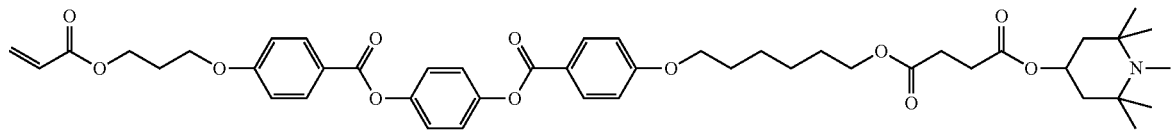

Example 3

Step 1

The procedures of Steps 1 to 8 of Example 2 were followed except that 6-chlorohexan-1-ol and 8-chlorooctan-1-ol were used in place of 3-chloro-1-propanol in Step 1 and 6-chlorohexan-1-ol in Step 3, respectively. A white solid was recovered as the product (3.4 g). Nuclear Magnetic Resonance (NMR) showed that the product had a structure consistent with 4-((4-((8-(4-((4-((4-((6-(acryloyloxy)hexyl)oxy)benzoyl)oxy)phenoxy)carbonyl)phenoxy)octyl)oxy)-4-oxobutanoyl)oxy)-1,2,2,6,6-pentamethylpiperidine as represented by the following graphic formula.

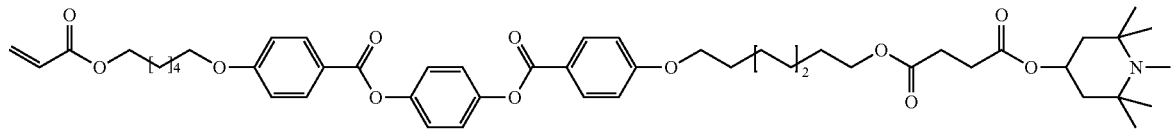

Example 4

Step 1

The procedures of Steps 1 to 6 of Example 2 were followed except 6-chlorohexan-1-ol and 8-chlorooctan-1-ol were used in place of 3-chloropropan-1-ol in Step 1 and 6-chlorohexan-1-ol in Step 3, respectively. The product was recovered as a white solid (48.5 g). Nuclear Magnetic Resonance (NMR) showed that the product had a structure consistent with 4-((4-((6-(acryloyloxy)hexyl)oxy)benzoyl)oxy)phenyl 4-((8-hydroxyoctyl)oxy)benzoate.

Step 2

To a 2 L of single-neckled, round-bottomed flask charged with 1000 mL of methylene chloride was added the product from Step 1 (95.7 g, 151.2 mmol) and ε-caprolactone (138.1 g, 1210.0 mmol). To the resulting solution was added aluminum triisopropylate (9.3 g, 45.4 mmol) and was stirred at room temperature under nitrogen protection for eight hours. The resulting solution was washed with 1 N hydrochloric acid solution (200 mL×3), saturated sodium bicarbonate aqueous solution (200 mL×1), and saturated brine (100 mL×3). Drying over magnesium sulfate, flashing through a silica gel plug column, and evaporation of the solvent yielded a white wax as the product (222.3 g). Nuclear Magnetic Resonance (NMR) showed that the product had a structure consistent with 6-(6-(6-(6-(6-(6-(6-(8-(4-(4-(4-(6-acryloyloxyhexyloxy)benzoyloxy)phenoxycarbonyl)phenoxy)octyloxy) 6-oxohexyloxy)-6-oxohexyloxy)-6-oxohexyloxy)-6-oxohexyloxy)-6-oxohexyloxy)-6-oxohexyloxy)-6-oxohexyloxy)-6-oxohexan-1-ol.

Step 3

To a reaction flask containing 300 mL of toluene was added the product from Step 7 of Example 2 (92.10 g, 0.34 mol) and thionyl chloride (48.46 g, 0.41 mol). The resulting mixture was heated at 80 degree under a nitrogen atmosphere for three hours. Evaporation of the solvent yielded a black sticky material which was used directly without further treatment.

Step 4

To a reaction flask containing 100 mL of dichloromethane was added the product from Step 2 (5.10 g, 3.30 mmol), the product from Step 3 (3.23 g, 9.90 mmol) and triethylamine (1.17 g, 11.6 mmol). The resulting solution was stirred under a nitrogen atmosphere overnight. The resulting solution was washed with 5% sodium hydroxide solution (30 mL×3), saturated sodium bicarbonate aqueous solution (30 mL×1), and saturated brine (30 mL×3). After drying over magnesium sulfate, evaporation of the solvent yielded a black material which was absorbed onto silica gel and a plug column was run on silica gel eluting with ethyl acetate/triethylamine (10/1, v/v). The resulting brown material was dissolved in minimal dichloromethane and precipitated from methanol cooled by acetone-dry ice bath. The resulting white precipitate was collected by filtration and dried in air (4.2 g). Nuclear Magnetic Resonance (NMR) showed that the product had a structure consistent with 4-((4-(6-(6-(6-(6-(6-(6-(6-(6-(8-(4-((4-((6-(acryloyloxy)hexyl)oxy)benzoyl)oxy)phenoxy)carbonyl)phenoxy)octyl)oxy)-6-oxohexyloxy)-6-oxohexyloxy)-6-oxohexyloxy)-6-oxohexyloxy)-6-oxohexyloxy)-6-oxohexyloxy)-6-oxohexyloxy)-4-oxobutanoyl)oxy)-1,2,2,6,6-pentamethylpiperidine as represented by the following graphic formula.

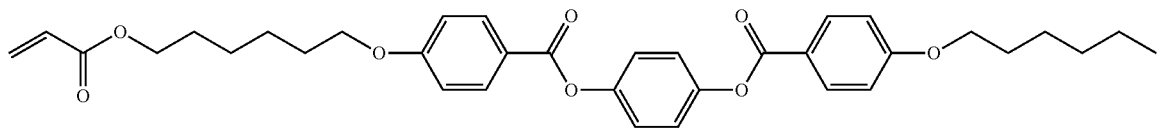

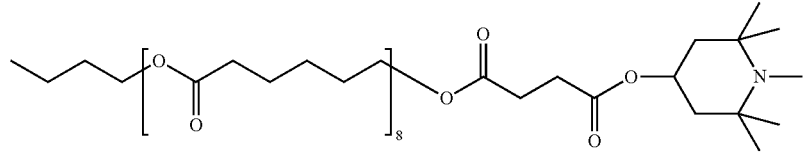

Example 5

Step 1

The procedure of Step 4 of Example 1 was followed except that 3-(3,5-di-tert-butyl-4-hydroxyphenyl)propanoic acid and [1,1'-biphenyl]-4,4'-diol (4 equivalent) were used in place of 4-((6-((tetrahydro-2H-pyran-2-yl)oxy)hexyl)oxy)benzoic acid and 2-methylhydroquinone. The product was further purified by column chromatography on silica gel eluting with hexane/ethyl acetate (70/30, v/v) followed by recrystallization from methanol. White crystals were recovered as the product (2.0 g). Nuclear Magnetic Resonance (NMR) showed that the product had a structure consistent with 4'-hydroxy-[1,1'-biphenyl]-4-yl 3-(3,5-di-tert-butyl-4-hydroxyphenyl)propanoate.

Step 2

To a reaction flask containing 500 mL of diethyl ether was added hydroxybenzoic acid (69.06 g, 0.5 mol), p-toluenesulfonic acid (5.0 g, 0.025 mol). To the resulting mixture was added dihydropyran (63.09 g, 0.75 mol) over a period of 45 min with stirring. After stirring overnight under a nitrogen atmosphere, the mixture was filtered, washed with 300 mL of dry diethyl ether and dried in air. A white solid (82.5 g) was recovered as the product. Nuclear Magnetic Resonance (NMR) showed that the product had a structure consistent with 4-(tetrahydro-2H-pyran-2-yloxy)benzoic acid.

Step 3

The procedures of Steps 4 and 5 of Example 1 were followed except that the product from Step 2 and the product from Step 1 were used in place of 4-((6-((tetrahydro-2H-pyran-2-yl)oxy)hexyl)oxy)benzoic acid and 2-methylhydroquinone. The final product was further purified by recrystallization from ethanol/water. A white solid was recovered as the product (1.09 g). Nuclear Magnetic Resonance (NMR) showed that the product had a structure consistent with 4'-((3-(3,5-di-tert-butyl-4-hydroxyphenyl)propanoyl)oxy)-[1,1'-biphenyl]-4-yl 4-hydroxybenzoate.

Step 4

The procedure of Step 4 of Example 1 was followed except that the product from Step 7 of example 2 and the product from Step 3 with a molar ratio of 1/1 were used in place of 4-((6-((tetrahydro-2H-pyran-2-yl)oxy)hexyl)oxy)benzoic acid and 2-methylhydroquinone. The product was further purified by column chromatography on silica gel eluting from hexane/ethyl acetate (50/50) to ethyl acetate/triethyl amine (10/1). A white solid was recovered as the product (0.5 g). Nuclear Magnetic Resonance (NMR) showed that the product had a structure consistent with 4-((4-(4-(((4'-((3-(3,5-di-tert-butyl-4-hydroxyphenyl)propanoyl)oxy)-[1,1'-biphenyl]-4-yl)oxy)carbonyl)phenoxy)-4-oxobutanoyl)oxy)-1,2,2,6,6-pentamethylpiperidine as represented by the following graphic formula.

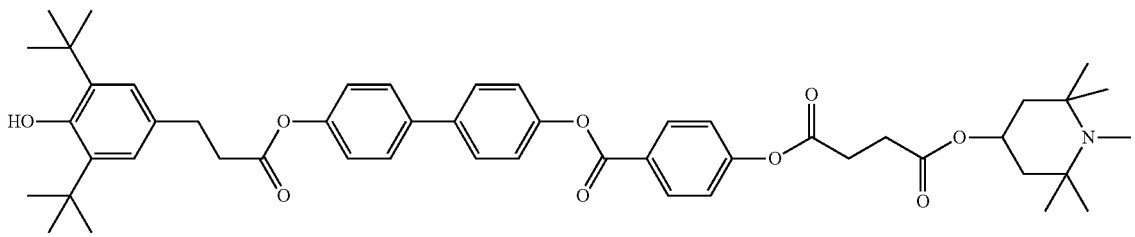 [SMILES: CN1C(C)(C)CC(OC(=O)CCC(=O)Oc2ccc(C(=O)Oc3ccc(-c4ccc(OC(=O)CCc5cc(C(C)(C)C)c(O)c(C(C)(C)C)c5)cc4)cc3)cc2)CC1(C)C]

Example 6

Step 1

To a reaction flask charged with ethyl 3,5-dihydroxybenzoate (10.0 g, 0.055 mol), pyridinium p-toluenesulfonate (2.76 g, 0.025 mol), and 0.5 L of diethyl ether was added dihydropyran (13.85 g, 0.165 mol) over a period of 45 min with stirring. After 3 hours, another 3 equivalents of dihydropyran was added followed by 10 g of anhydrous magnesium sulfate. The reaction was stirred overnight under a nitrogen atmosphere. Evaporation of the solvent yielded a product which was purified by column chromatography on silica gel eluting with hexane/ethyl acetate (85/15, v/v). 8.2 g of product was produced. The product was recovered a viscous liquid. Nuclear Magnetic Resonance (NMR) showed that the product had a structure consistent with ethyl 3,5-bis((tetrahydro-2H-pyran-2-yl)oxy)benzoate.

Step 2

To a reaction flask containing 100 mL of ethanol/water (1/1, v/v) was added the product from Step 2 (8.2 g, 0.0234 mol) and sodium hydroxide (4.7 g, 0.117 mol). The resulting mixture was heated to reflux for 5 hours. After addition of icy water (50 mL), hydrochloric acid (1N) was added to the suspension until the pH value of the mixture reached ~2-3. The aqueous phase was extracted with dichloromethane (4×100 mL). The organic phase was dried over anhydrous sodium sulfate, filtered and concentrated to give the product (7.4 g). Nuclear Magnetic Resonance (NMR) showed that the product had a structure consistent with 3,5-bis((tetrahydro-2H-pyran-2-yl)oxy)benzoic acid.

Step 3

The procedures of Steps 1, 3 to 5 of Example 5 were followed except that the product from Step 2 was used in place of 4-(tetrahydro-2H-pyran-2-yloxy)benzoic acid in Step 3. The product was recovered as a white solid (0.6 g). Nuclear Magnetic Resonance (NMR) showed that the product had a structure consistent with 4-((4-(3-(((4'-((3-(3,5-di-tert-butyl-4-hydroxyphenyl)propanoyl)oxy)-[1,1'-biphenyl]-4-yl)oxy)carbonyl)-5-((4-oxo-4-((1,2,2,6,6-pentamethylpiperidin-4-yl)oxy)butanoyl)oxy)phenoxy)-4-oxobutanoyl)oxy)-1,2,2,6,6-pentamethylpiperidine as represented by the following graphic formula.

crystals (82 g) as the product. Nuclear Magnetic Resonance (NMR) showed that the product had a structure consistent with 4-methoxy-4'-(trans-4-pentylcyclohexyl)biphenyl.

Step 2

To a reaction flask was added the product of Step 1 (80 g) and pyridine hydrochloride (300 g). The resulting mixture was heated to 200° C. for one hour and poured into 1000 mL of water while hot. The water was decanted and the product was dissolved in 500 mL of methylene chloride, washed with distilled water (100 mL×3) and saturated sodium bicarbonate aqueous solution (100 mL×3), dried over anhydrous magnesium sulfate and concentrated. The residue was recrystallized from ethanol yielding white crystals as the final product (75

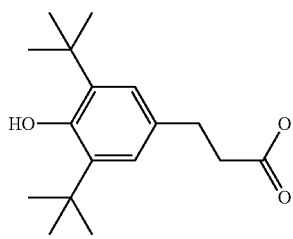
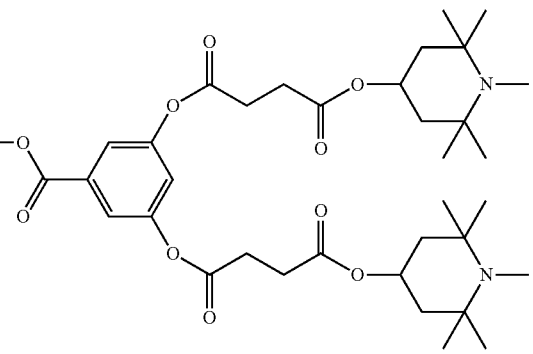

Example 7

Step 1

To a reaction flask containing 500 mL of dimethyl ethylene glycol and 570 mL of water was added 1-bromo-4-(trans-4-pentylcyclohexyl)benzene (43.31 g, 0.285 mol), 4-methoxyphenylboronic acid (88.1 g, 0.285 mol), tetrakistriphenylphosphine palladium (0) (1.64 g, 1.4 mmol) and sodium carbonate (121 g, 1.14 mol) under nitrogen protection. The resulting mixture was degassed by bubbling nitrogen for 10 minutes and heated to reflux for 4 hours. After cooling to room temperature, methylene chloride (1 L) and water (500 mL) were added and the resulting mixture was stirred. The organic layer was recovered, dried over anhydrous magnesium sulfate, filtered and concentrated. The product was purified by recrystallization from ethyl acetate to yield white g). Nuclear Magnetic Resonance (NMR) showed that the product had a structure consistent with 4-hydroxy-4'-(trans-4-pentylcyclohexyl)biphenyl.

Step 3

The procedure of Step 4 of Example 1 was followed except the product from Step 2 and the product from Step 7 of example 2 (1 equivalent) were used in place of 2-methylhydroquinone and 4-((6-(((tetrahydro-2H-pyran-2-yl)oxy)hexyl)oxy)benzoic acid. The purification was done by recrystallization from ethanol/ethyl acetate (50/50, v/v). White crystals (8.5 g) were recovered as the product. Nuclear Magnetic Resonance (NMR) showed that the product had a structure consistent with 1,2,2,6,6-pentamethyl-4-((4-oxo-4-((4'-(trans-4-pentylcyclohexyl)-[1,1'-biphenyl]-4-yl)oxy)butanoyl)oxy)piperidine as represented by the following graphic formula.

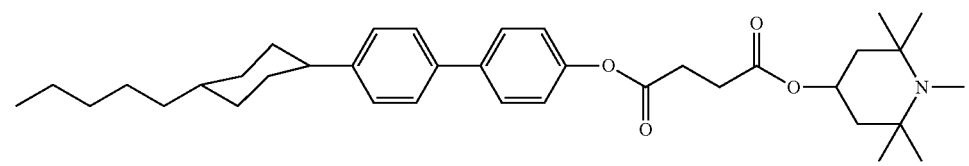 [SMILES: CCCCCC1CCC(c2ccc(-c3ccc(OC(=O)CCC(=O)OC4CC(C)(C)N(C)C(C)(C)C4)cc3)cc2)CC1]

Example 8

Step 1

To a 10 L of reaction flask containing 6 L of distilled water was added hydroquinone (660 g, 6 mol) and sodium carbonate (636 g, 6 mol). To the resulting mixture was added 4-methylbenzoic chloride (773 g, 5 mol) dropwise under nitrogen. After the addition of 4-methylbenzoic chloride was complete, the resulting suspension was stirred for 4 hours at room temperature. The precipitate that formed was filtered, washed with distilled water (6 L), dissolved in the mixture of chloroform (6 L) and distilled water (1 L) and heated to 50° C. with stirring. The organic phase was recovered and cooled to room temperature. The resulting precipitate was filtered and dried under 50° C. A white solid (650 g) was recovered as the product. Nuclear Magnetic Resonance (NMR) showed that the product had a structure consistent with 4-hydroxyphenyl 4-methylbenzoate.

Step 2

The procedures of Steps 1 to 5 of Example 1 were followed except that 8-chloro-1-hexanol was used in place of 6-chloro-1-hexanol in Step 1 and 4-hydroxyphenyl 4-methylbenzoate and 4-((8-((tetrahydro-2H-pyran-2-yl)oxy)octyl)oxy)benzoic acid (1 equivalent) were used in place of 2-methylquinone and 4-((6-((tetrahydro-2H-pyran-2-yl)oxy)hexyl)oxy)benzoic acid in Step 4. A white solid was recovered as the product (499.4 g). Nuclear Magnetic Resonance (NMR) showed that the product had a structure consistent with 4-((4-((8-hydroxyoctyl)oxy)benzoyl)oxy)phenyl 4-methylbenzoate.

Step 3

The procedures of Steps 3 and 4 of Example 4 were followed except that 4-((4-((8-hydroxyoctyl)oxy)benzoyl)oxy)phenyl 4-methylbenzoate was used in place of 6-(6-(6-(6-(6-(6-(6-(6-(8-(4-(4-(4-(6-acryloyloxyhexyloxy)benzoyloxy)phenoxycarbonyl)phenoxy)octyloxy) 6-oxohexyloxy)-6-oxohexyloxy)-6-oxohexyloxy)-6-oxohexyloxy)-6-oxohexyloxy)-6-oxohexyloxy)-6-oxohexan-1-ol. The product was purified by chromatography on silica gel eluting with hexane/ethyl acetate (50/50, v/v). A white solid was recovered as the product (4.2 g). Nuclear Magnetic Resonance (NMR) showed that the product had a structure consistent with 1,2,2,6,6-pentamethyl-4-((4-((8-(4-((4-((4-methylbenzoyl)oxy)phenoxy)carbonyl)phenoxy)octyl)oxy)-4-oxobutanoyl)oxy)piperidine as represented by the following graphic formula.

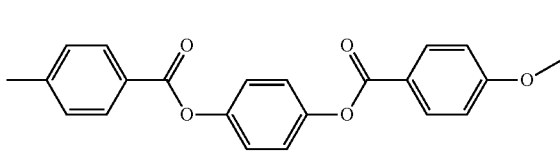

Example 9

Step 1

The procedures of Steps 1 to 5 of Example 1 were followed except that one equivalent of 4-(4-pentylcyclohexyl)phenol was used in place of 2-methylquinone at Step 4. A white solid was recovered as the product (1.1 Kg). Nuclear Magnetic Resonance (NMR) showed that the product had a structure consistent with 4-(trans-4-pentylcyclohexyl)phenyl 4-((6-hydroxyhexyl)oxy)benzoate.

Step 2

The procedure of Step 3 of Example 8 was followed except the product from Step 1 was used in place of 4-((4-((8-hydroxyoctyl)oxy)benzoyl)oxy)phenyl 4-methylbenzoate. A sticky light brown material was recovered as the product (5.0 g). Nuclear Magnetic Resonance (NMR) showed that the product had a structure consistent with 1,2,2,6,6-pentamethyl-4-((4-oxo-4-((6-(4-((4-(trans-4-pentylcyclohexyl)phenoxy)carbonyl)phenoxy)hexyl)oxy)butanoyl)oxy)piperidine as represented by the following graphic formula.

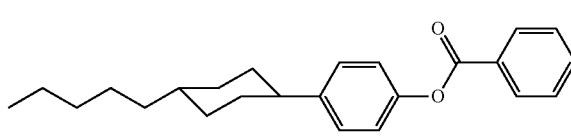

Example 10

Step 1

The procedure of Step 1 of Example 1 was followed except that the product from Step 2 of Example 7 was used in place of methyl 4-hydroxy benzoate. The product was recovered as white crystals (502 g). Nuclear Magnetic Resonance (NMR) showed that the product had a structure consistent with 6-((4'-(trans-4-pentylcyclohexyl)-[1,1'-biphenyl]-4-yl)oxy)hexan-1-ol.

Step 2

The procedure of Step 3 of Example 8 was followed except the product from Step 1 was used in place of 4-((4-((8-hydroxyoctyl)oxy)benzoyl)oxy)phenyl 4-methylbenzoate. A white solid was recovered as the product (3.8 g). Nuclear Magnetic Resonance (NMR) showed that the product had a structure consistent with 1,2,2,6,6-pentamethyl-4-((4-oxo-4-((6-((4'-(trans-4-pentylcyclohexyl)-[1,1'-biphenyl]-4-yl)oxy)hexyl)oxy)butanoyl)oxy)piperidine as represented by the following graphic formula.

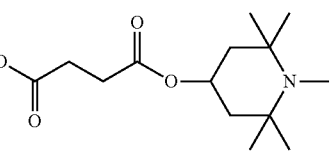

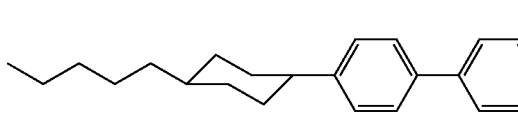
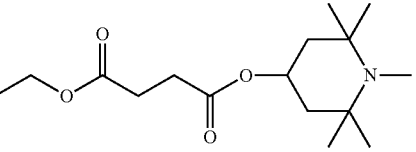

Example 11

To a reaction flask charged with the product from Step 2 of Example 7 (5 g, 16 mmol) diethleneglycol bischloroformate (4.08 g, 15.50 mmol), 1,2,2,6,6-pentamethylpiperidin-4-ol (2.66 g, 16 mmol) and 50 mL of methylene chloride was added pyridine (2.6 g, 31.8 mmol) at 0° C. The mixture was warmed to room temperature and heated to reflux overnight. The resulting mixture was washed with 2N hydrochloric acid aqueous solution (20 mL×3), 5% sodium hydroxide solution (20 mL×1), and distilled water (20 mL×1) and dried over anhydrous magnesium sulfate. After filtration, the filtrate was evaporated to dryness yielding a product which was purified by Combi Flash on silica gel eluting with gradient hexane/ethyl acetate to give the final product in a form of a white solid (2.3 g). Nuclear Magnetic Resonance (NMR) showed that the product had a structure consistent with 1,2,2,6,6-pentamethyl-4-(((2-(2-((((4'-(trans-4-pentylcyclohexyl)-[1,1'-biphenyl]-4-yl)oxy)carbonyl)oxy)ethoxy)ethoxy)carbonyl)oxy)piperidine as represented by the following graphic formula.

4-((6-((tetrahydro-2H-pyran-2-yl)oxy)octyl)oxy)benzoic acid (1 equivalent) were used in place of 2-methylhydroquinone and 4-((6-((tetrahydro-2H-pyran-2-yl)oxy)hexyl)oxy)benzoic acid in Step 4. The product was purified by precipitation from methylene chloride/methanol (1/10, v/v). A white solid was recovered as the product (557.9 g). Nuclear Magnetic Resonance (NMR) showed that the product had a structure consistent with 4'-(benzyloxy)-[1,1'-biphenyl]-4-yl 4-((8-((tetrahydro-2H-pyran-2-yl)oxy)octyl)oxy)benzoate.

Step 3

To a reaction flask containing 2500 mL of tetrahydrofuran was added the product from Step 2 (280.00 g, 0.46 mol) and 10% Pd/C (Palladium on Carbon) (30.00 g). The resulting mixture was hydrogenated up to 50 atm hydrogen pressure at room temperature for 48 hours. After filtration, the filtrate was concentrated to a minimal amount and 1500 mL of methanol was added. The formed precipitate was stirred for two more hours and filtered. The solid was rinsed with methanol (500 mL) and dried in vacuum to yield the final product in a form of white solid (210.00 g). Nuclear Magnetic Resonance (NMR) showed that the product had a structure consistent

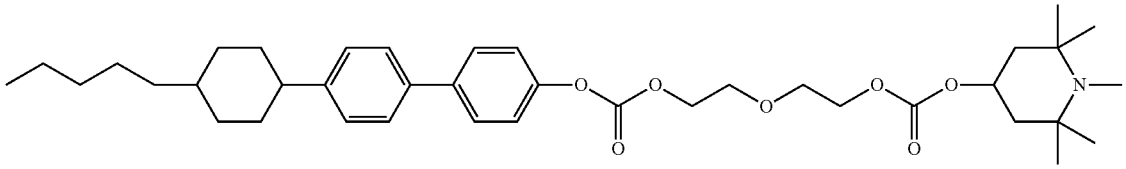 [SMILES: CCCCCC1CCC(c2ccc(-c3ccc(OC(=O)OCCOCCOC(=O)OC4CC(C)(C)N(C)C(C)(C)C4)cc3)cc2)CC1]

Example 12

Step 1

To a reaction flask containing 3000 mL of ethanol was added 4,4'-Dihydroxybiphenyl (279.32 g, 1.50 mol) and sodium hydroxide (60.00 g, 1.50 mol). The solution was heated to reflux. Once the solution turned dark green, benzyl chloride (189.87 g, 1.50 mol) was added. After refluxing for three more hours, the solution was allowed to cool to room temperature. The formed precipitate was collected by filtration and rinsed with ethanol to yield a product which was dissolved in 3000 ml of N,N-dimethylformamide. After filtration, the filtrate was concentrated to a minimal amount under reduced pressure and 3000 mL of distilled water was added. The formed precipitate was stirred for one more hour and collected by filtration, rinsed with distilled water, and dried in vacuum to yield the final product (163.80 g). Nuclear Magnetic Resonance (NMR) showed that the product had a structure consistent with 4'-(benzyloxy)biphenyl-4-ol.

Step 2

The procedures of Steps 1 to 4 of Example 1 were followed except that 8-chloro-1-octanol was used in place of 6-chloro-1-hexanol in Step 1 and 4'-(benzyloxy)biphenyl-4-ol and with 4'-hydroxy-[1,1'-biphenyl]-4-yl 4-((8-((tetrahydro-2H-pyran-2-yl)oxy)octyl)oxy)benzoate.

Step 4

The procedure of Step 5 of Example 1 was followed except that the product from Step 3 was used in place of 2-methyl-1,4-phenylene bis(4-((6-((tetrahydro-2H-pyran-2-yl)oxy)hexyl)oxy)benzoate). A white solid was recovered as the product (4.1 g).

Step 5

The procedure of Step 4 of Example 1 was followed except the product from Step 4 and the product from Step 7 of Example 2 were used in place of 4-((6-((tetrahydro-2H-pyran-2-yl)oxy)hexyl)oxy)benzoic acid and 2-methylhydroquinone. A white solid was recovered as the product (3.8 g). Nuclear Magnetic Resonance (NMR) showed that the product had a structure consistent with 4-((4-(4-((4-((6-(acryloyloxy)hexyl)oxy)benzoyl)oxy)phenoxy)-4-oxobutanoyl)oxy)-1,2,2,6,6-pentamethylpiperidine as represented by the following graphic formula.

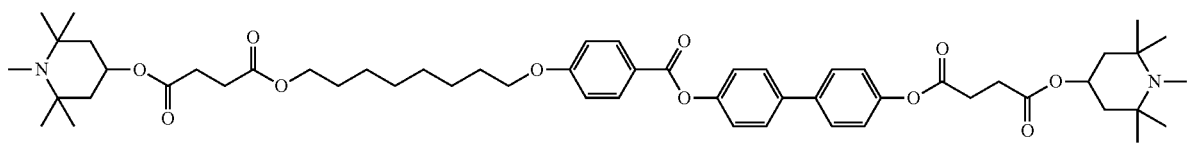

Example 13

Step 1
The procedure of Step 2 of Example 2 were followed except the product from Step 2 of Example 1 was used in place of 4-((3-hydroxypropyl)oxy)benzoic acid. A white solid was recovered as the product (86.5 g). Nuclear Magnetic Resonance (NMR) showed that the product had a structure consistent with 4-(6-(acryloyloxy)hexoxy)benzoic acid.

Step 3
To a reaction flask charged with hydroquinone (880.0 g, 8.0 mol), ferric sulfate hydrate (40.0 g, 0.1 mol) and 6.5 L of diethyl ether was added dihydropyran (672.1 g, 8 mol) over a period of one hour with stirring. After stirring overnight with nitrogen bubbling, the solution was extracted twice with nitrogen-purged solutions of 480 g of sodium hydroxide in 4.800 L of distilled water (total: 12.0 mol). The combined aqueous solutions were extracted with 3.0 L of diethyl ether. Sodium bicarbonate (20.0 g) was added, and the stirred solution was slowly acidified with acetic acid (328.6 g, 5.47 mol). The resulting mixture was stored under 0° C. overnight. The precipitated product was collected by filtration and dried under vacuum. 528.0 g of product was produced in a form of a light brown solid. Nuclear Magnetic Resonance (NMR) showed that the product had a structure consistent with 4-((tetrahydro-2H-pyran-2-yl)oxy)phenol.

Step 4
The procedures of Steps 4 to 5 of Example 1 were followed except that the product from Step 3 and the product from Step 2 (1 equivalent) were used in place of 2-methyl hydroquinone and 4-((6-(((tetrahydro-2H-pyran-2-yl)oxy)hexyl)oxy)benzoic acid in Step 4. A white solid was recovered as the product (216 g). Magnetic Resonance (NMR) showed that the product had a structure consistent with 4-hydroxyphenyl 4-((6-(acryloyloxy)hexyl)oxy)benzoate.

Step 5
The procedures of Steps 3 to 4 of Example 4 were followed expect that the product from Step 4 was used in place of 6-(6-(6-(6-(6-(6-(6-(6-(8-(4-(4-(4-(6-acryloyloxyhexyloxy)benzoyloxy)phenoxycarbonyl)phenoxy)octyloxy) 6-oxohexyloxy)-6-oxohexyloxy)-6-oxohexyloxy)-6-oxohexyloxy)-6-oxohexyloxy)-6-oxohexyloxy)-6-oxohexyloxy)-6-oxohexan-1-ol. The product was purified by Combi Flash on silica gel eluting with gradient hexane/ethyl acetate. A white solid was recovered as the product (3.0 g). Nuclear Magnetic Resonance (NMR) showed that the product had a structure consistent with 4-((4-(4-((4-((6-(acryloyloxy)hexyl)oxy)benzoyl)oxy)phenoxy)-4-oxobutanoyl)oxy)-1,2,2,6,6-pentamethylpiperidine as represented by the following graphic formula.

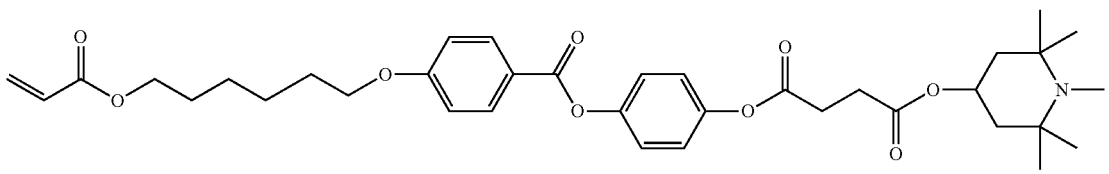 [SMILES: C=CC(=O)OCCCCCCOc1ccc(C(=O)Oc2ccc(OC(=O)CCC(=O)OC3CC(C)(C)N(C)C(C)(C)C3)cc2)cc1]

Example 14

The procedures of Steps 1 to 3 of Example 7 were followed except dihydro-2H-pyran-2,6(3H)-dione was used in place of succinic anhydride in Step 3. A white solid was recovered as the product (3.9 g). Nuclear Magnetic Resonance (NMR) showed that the product had a structure consistent with 1,2,2,6,6-pentamethyl-4-((5-oxo-5-((4'-(4-pentylcyclohexyl)-[1,1'-biphenyl]-4-yl)oxy)pentanoyl)oxy)piperidine as represented by the following graphic formula.

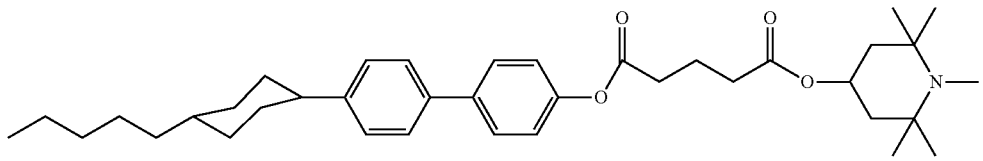 [SMILES: CCCCCC1CCC(c2ccc(-c3ccc(OC(=O)CCCC(=O)OC4CC(C)(C)N(C)C(C)(C)C4)cc3)cc2)CC1]

Part 2—Liquid Crystal Coating Components and Formulations

"LCM" represents liquid crystal monomers.
"PC" represents photochromic materials.
"LCCF" represents liquid crystal coating formulation.

LCM-1 is 1-(6-(8-(4-(4-(4-(8-acryloyloxyhexyl)oxy)benzoyloxy)phenyloxycarbonyl)phenoxy)octyloxy)-6-oxohexyloxy)-6-oxohexyloxy)-6-oxohexyloxy)-6-oxohexyloxy)-6-oxohexyloxy)-6-oxohexyloxy)-6-oxohexyloxy)-6-oxohexan-1-ol which was prepared according to the procedures described in Example 17 of U.S. Pat. No. 7,910,019, which liquid crystal monomer disclosure is incorporated herein by reference.

LCM-2 is commercially available RM257 reported to be 4-(3-acryloyloxypropyloxy)-benzoic acid 2-methyl-1,4-phenylene ester, available from EMD Chemicals, Inc., having the molecular formula of $C_{33}H_{32}O_{10}$.

LCM-3 is 1-(6-(4-(4-(trans-4-pentylcyclohexyl)phenoxycarbonyl)phenoxy)hexyloxy)-2-methylprop-2-en-1-one prepared according to the procedure of Example 1 in U.S. Pat. No. 7,910,019, except that n=0, which disclosure is incorporated herein by reference.

LCM-4 is 1-(6-(6-(6-(6-(6-(6-(6-(8-(4-(4-(4-hexyloxybenzoyloxy)phenoxycarbonyl)-phenoxy)octyloxy)-6-oxohexyloxy)-6-oxohexyloxy)-6-oxohexyloxy)-6-oxohexyloxy)-6-oxohexyloxy)-6-oxohexyloxy)-6-oxohexyloxy)-2-methylprop-2-en-1-one prepared according to the procedures of U.S. Pat. No. 7,910,019, which disclosure is incorporated herein by reference.

PC-A is an indenonaphthopyran that demonstrates a yellow color upon activation.

PC-B is an indenonaphthopyran that demonstrates a purple color upon activation.

PC-C is an indenonaphthopyran that demonstrates a blue-green color upon activation.

PC-D is an indenonaphthopyran that demonstrates a blue color upon activation.

PC-E is an indenonaphthopyran that demonstrates a blue color upon activation.

PC-F is an indenonaphthopyran that demonstrates a blue color upon activation.

PC-G is an indenonaphthopyran that demonstrates a blue color upon activation.

TABLE 1

Photochromic Dyes in Grey Coloring Formulations 1, 2 & 3 (Reported in weight percent based on the total weight of the coloring formulation)

| Photochromic | GREY-1 | GREY-2 | GREY-3 |
|---|---|---|---|
| PC-A | 11.4 | 25.0 | 23.0 |
| PC-B | 7.5 | — | — |
| PC-C | 11.1 | 17.0 | 15.0 |
| PC-D | 14.7 | 20.0 | 10.0 |
| PC-E | 44.8 | — | — |
| PC-F | 10.5 | 18.0 | 25.0 |
| PC-G | — | 20.0 | 27.0 |

LCCF-1 was prepared as follows:

To a suitable flask containing a mixture of anisole (3.99 g) and BYK-322 additive 0.004 g, reported to be an aralkyl modified poly-methyl-alkyl-siloxane available from BYK Chemie, USA), was added LCM-1 (1.08 g), LCM-2 (2.4 g), LCM-3 (1.08 g), LCM-4 (1.44 g), Grey-1 (0.72 g), 4-methoxyphenol (0.006 g), and IRGACURE® 819 (0.09 g, a photoinitiator available from Ciba-Geigy Corporation). Examples 1, 2 and 3 were separately added to LCCF-1 at a molar ratio of 1:3 (Example #:Grey-1). Examples 12, 13 and 14 were added but did not dissolve, so no further testing was performed. The resulting mixture was stirred for 2 hours at 80° C. and cooled to about 26° C. Grey-1 Control contained the same materials as LCCF-1 except without the Example.

LCCF-2 was prepared following the procedure used to prepare LCCF-1 except that Grey 2 (0.78 g) was added to the mixture and Examples 4, 5 and 6 were added to LCCF-2 at a molar ratio of 1:3 (Example #:Grey-2). The same amount of Grey-2 was added to the Grey-2 Control.

LCCF-3 was prepared following the procedure used to prepare LCCF-2 except that Grey 3 (0.78 g) was added to the mixture and Examples 7, 8, 9, 10 and 11 were added to LCCF-3 at a molar ratio of 1:3 (Example #:Grey-3). CYASORB® UV-24, a light absorber available from Cytec Industries, was also added at a molar ratio of 1:3 (UV-24:Grey-3). The resulting mixture was stirred for 2 hours at 80° C. and cooled to about 26° C. Grey-3 Control contained the same materials as LCCF-3 except without the Example.

Part 3—Preparation of Photoalignment Coating Solution

A solution of a photoalignment material of the type described in U.S. patent application Ser. No. 12/959,467 filed on Dec. 3, 2010, which application is incorporated herein by reference was prepared by adding 6 weight percent of the photoalignment material to cyclopentanone, based on the total weight of the solution.

Part 4—Preparation of Transitional Layer Coating Formulation (TLCF)

The TLCF was prepared as follows:

In a 50 mL amber glass bottle equipped with a magnetic stir-bar following materials were added:

Hydroxy methacrylate (1.242 g) from Sigma-Aldrich;
Neopentyl glycol diacrylate (13.7175 g) SR247 from Sartomer;
Trimethylolpropane trimethacrylate (2.5825 g) SR350 from Sartomer;
DESMODUR® PL 340 (5.02 g) from Bayer Material Science;
IRGACURE®-819 (0.0628 g) from Ciba Speciality Chemicals;
DAROCUR® TPO (0.0628 g; from Ciba Speciality Chemicals,
Polybutyl acrylate (0.125 g),
3-Aminopropylpropyltrimethoxysilane (1.4570 g) A-1100 from Momentive Performance Materials;
200 proof absolute anhydrous Ethanol (1.4570 g) from Pharmaco-Aaper; and
Tinuvin 1130 (0.5145 g) from Ciba Specialty Chemicals.

The mixture was stirred at room temperature for 2 hrs.

Part 5—Procedures Used for Preparing and Coating the Substrates

Square substrates measuring 5.08 cm by 5.08 cm by 0.318 cm (2 inches (in.) by 2 in. by 0.125 in.) prepared from CR-390 monomer were obtained from Homalite, Inc were used for Examples 1, 2 and 3. Finished single vision lenses (6 base, 70 mm) prepared from CR-39® monomer were also used for Examples 4-11. Each substrate prepared from CR-39® monomer was cleaned by wiping with a tissue soaked with acetone and dried with a stream of air.

Each of the aforementioned substrates was corona treated by passing on a conveyor belt in Tantec EST Systems Serial No. 020270 Power Generator HV 2000 series corona treatment equipment with a high voltage transformer. The substrates were exposed to corona generated by 53.99 KV, 500 Watts while traveling on a conveyor at a belt speed 3 ft/min.

Coating Procedure for Photoalignment Materials

The photoalignment coating solution prepared in Part 3 was applied to the test substrates by spin-coating on a portion of the surface of the test substrate by dispensing approximately 1.0 mL of the solution and spinning the substrates at 800 revolutions per minute (rpm) for 3 seconds, followed by 1,000 rpm for 7 seconds, followed by 2500 rpm for 4 seconds. A spin processor from Laurell Technologies Corp. (WS-400B-6NPP/LITE) was used for spin coating. Afterwards, the coated substrates were placed in an oven maintained at 120° C. for 30 minutes. The coated substrates were cooled to about 26° C.

The dried photoalignment layer on each of the substrates was at least partially ordered by exposure to linearly polarized ultraviolet radiation using a DYMAX® UVC-6 UV/conveyor system by DYMAX® Corp. having a 400 Watt power supply. The light source was oriented such that the radiation was linearly polarized in a plane perpendicular to the surface of the substrate. The amount of ultraviolet radiation that each photoalignment layer was exposed to was measured using a UV Power Puck™ High energy radiometer from EIT Inc (Serial No. 2066) and was as follows: UVA 0.126 W/cm$^2$ and 5.962 J/cm$^2$; UVB 0.017 W/cm$^2$ and 0.078 J/cm$^2$; UVC 0 W/cm$^2$ and 0 J/cm$^2$; and UVV 0.046 W/cm$^2$ and 2.150 J/cm$^2$. After ordering at least a portion of the photo-orientable polymer network, the substrates were cooled to about 26° C. and kept covered.

Coating Procedure for Liquid Crystal Coating Formulations

The Liquid Crystal Coating Formulations ("LCCF") prepared in Part 2 were each spin coated at a rate of 400 revolutions per minute (rpm) for 6 seconds, followed by 800 rpm for 6 seconds onto the at least partially ordered photoalignment materials prepared as described above on the test substrates. Each coated substrate was placed in an oven at 60° C. for 30 minutes. Afterwards the substrates were cured under two ultraviolet lamps in the UV Curing Oven Machine designed and built by Belcan Engineering in nitrogen atmosphere while running on a conveyor belt at 2 ft/min speed at peak intensity of 0.445 Watts/cm$^2$ of UVA and 0.179 Watts/cm$^2$ of UVV and UV dosage of 2.753 Joules/cm$^2$ of UVA and 1.191 Joules/cm$^2$ of UVV. The cured layers were exposed to corona generated by 53.00 KV, 500 Watts while traveling on a conveyor at a belt speed 3 ft/min.

Coating Procedure for Transitional Layer

The Transitional layer solution prepared in Part 4 was spin coated at a rate of 1,400 revolutions per minute (rpm) for 7 seconds onto the cured LCCF coated substrates with Examples 7, 8, 9, 10 and 11 prepared as described above. Afterwards the coated substrates were cured under two ultraviolet lamps in the UV Curing Oven Machine designed and built by Belcan Engineering in nitrogen atmosphere while running on a conveyor belt at 6 ft/min speed at peak intensity of 1.887 Watts/cm$^2$ of UVA and 0.694 Watts/cm$^2$ of UVV and UV dosage of 4.699 Joules/cm$^2$ of UVA and 1.787 Joules/cm$^2$ of UVV. The cured transitional layers were exposed to corona generated by 53.00 KV, 500 Watts while traveling on a conveyor at a belt speed 3 ft/min. Post curing of the coated substrates was completed at 105° C. for 3 hours.

Part 6—Measurements

Measurement of Clearing Temperatures Upon Heating and Cooling

Approximately 0.1-5 mg of a sample of each of the Examples listed in Table 2 was applied to a VWR Vista Vision™ microscope slide. A FISHERFINEST® Premium cover glass was applied to the sample. The resulting microscope slide was placed onto an INSTEC® HCS302 hot stage that was mounted on the sample stage of an OLYMPUS® BX51 polarized light microscope so that the sample spot was in the optical path of the microscope. The microscope was also equipped with an INSTEC® STC200 temperature controller, so that the temperature of the hot stage was controlled, and a DIAGNOSTIC INSTRUMENTS 11.2 Color Mosaic camera, so that the clearing temperature upon heating and cooling could be observed from a computer display. All of the samples of the Examples listed in Table 2 demonstrated the Nematic phase. Clearing temperatures were measured by observing the samples during heating at a rate of 1° C./min starting at 25° C. Cooling temperatures were observed after turning off the heat.

TABLE 2

Clearing Temperature Data

| Example No. | Clearing Temperature upon Heating (° C.) | Clearing Temperature upon Cooling (° C.) |
|---|---|---|
| Grey-1 Control | 83 | 76 |
| Example 1 | 74 | 69 |
| Example 2 | 88 | 75 |
| Example 3 | 81 | 75 |
| Grey-2 Control | 81 | 76 |
| Example 4 | 77 | 75 |
| Example 5 | 78 | 75 |
| Example 6 | 78 | 75 |
| Grey-3 Control | 83 | 73 |
| Example 7 | 88 | 70 |
| Example 8 | 72 | 67 |
| Example 9 | 73 | 65 |
| Example 10 | 73 | 67 |
| Example 11 | 72 | 67 |

Photochromic Performance Tests Including Absorption Ratio, Optical Response Measurements and Fatigue Prior to response testing on an optical bench, the substrates were conditioned by exposing them to 365 nm ultraviolet light for 10 minutes at a distance of about 14 cm from the source in order to pre-activate the photochromic molecules. The UVA irradiance at the sample was measured with a Licor Model Li-1800 spectroradiometer and found to be 22.2 Watts per square meter. The samples were then placed under a halogen lamp (500 W, 120 V) for about 10 minutes at a distance of about 36 cm from the lamp in order to bleach, or inactivate, the photochromic compound in the samples. The illuminance at the sample was measured with the Licor spectroradiometer and found to be 21.9 Klux. The samples were then kept in a dark environment for at least 1 hour prior to testing in order to cool and continue to fade back to a ground state.

An optical bench was used to measure the optical, properties of the coated substrates and derive the absorption ratio and photochromic properties. Each test sample was placed on the optical bench with an activating light source (a Newport/Oriel Model 66485 300-Watt Xenon arc lamp fitted with a UNIBLITZ® VS-25 high-speed computer controlled shutter that momentarily closed during data collection so that stray light would not interfere with the data collection process, a SCHOTT® 3 mm KG-2 band-pass filter, which removed short wavelength radiation, neutral density filter(s) for intensity attenuation and a condensing lens for beam collimation) positioned at a 30° to 35° angle of incidence to the surface of the test sample. The arc lamp was equipped with a light intensity controller (Newport/Oriel model 68950).

A broadband light source for monitoring response measurements was positioned in a perpendicular manner to a surface of the test sample. Increased signal of shorter visible wavelengths was obtained by collecting and combining separately filtered light from a 100-Watt tungsten halogen lamp (controlled by a constant voltage powder supply) with a split-end, bifurcated fiber optical cable. Light from one side of the tungsten halogen lamp was filtered with a SCHOTT® KG1 filter to absorb heat and a HOYA® B-440 filter to allow passage of the shorter wavelengths. The other side of the light was either filtered with a SCHOTT® KG1 filter or unfiltered. The light was collected by focusing light from each side of the lamp onto a separate end of the split-end, bifurcated fiber optic cable, and subsequently combined into one light source emerging from the single end of the cable. A 4" or 6" light pipe was attached to the single end of the cable to insure proper mixing. The broad band light source was fitted with a UNIB- LITZ® VS-25 high-speed computer controlled shutter that momentarily opened during data collection.

Polarization of the light source was achieved by passing the light from the single end of the cable through a Moxtek, PROFLUX® Polarizer held in a computer driven, motorized rotation stage (Model M-061-PD from Polytech, PI or equivalent). The monitoring beam was set so that the one polarization plane (0°) was perpendicular to the plane of the optical bench table and the second polarization plane (90°) was parallel to the plane of the optical bench table. The samples were run in air, at 23° C.±0.1° C. maintained by a temperature controlled air cell.

To align each sample, a second polarizer was added to the optical path. The second polarizer was set to 90° of the first polarizer. The sample was placed in an air cell in a self-centering holder mounted on a rotation stage. A laser beam (Coherent-ULN 635 diode laser) was directed through the crossed polarizers and sample. The sample was rotated (in 3° steps as coarse moves and in 0.1° steps as fine moves) to find the minimum transmission. At this point the sample was aligned either parallel or perpendicular to the Moxtek polarizer and the second polarizer as well as the diode laser beam was removed from the optical path. The sample was aligned within ±0.5° prior to any activation.

To conduct the measurements, each test sample was exposed to 6.7 W/m$^2$ of UVA from the activating light source for 10 to 20 minutes to activate the photochromic compound. An International Light Research Radiometer (Model IL-1700) with a detector system (Model SED033 detector, B Filter, and diffuser) was used to verify exposure at the beginning of each day. Light from the monitoring source that was polarized to the 0° polarization plane was then passed through the coated sample and focused into a 1" integrating sphere, which was connected to an OCEAN OPTICS® S2000 spectrophotometer or equivalent using a single function fiber optic cable. The spectral information, after passing through the sample, was collected using OCEAN OPTICS® OOIBase32 and OOIColor software, and PPG propriety software. While the photochromic material was activated, the position of the polarizing sheet was rotated back and forth to polarize the light from the monitoring light source to the 90° polarization plane and back. Data was collected for approximately 600 to 1200 seconds at 5-second intervals during activation. For each test, rotation of the polarizers was adjusted to collect data in the following sequence of polarization planes: 0°, 90°, 90°, 0°, etc.

Absorption spectra were obtained and analyzed for each test sample using the Igor Pro software (available from WaveMetrics). The change in the absorbance in each polarization direction for each test sample was calculated by subtracting out the 0 time (i.e., unactivated) absorption measurement for the samples at each wavelength tested. Average absorbance values were obtained in the region of the activation profile where the photochromic response of the photochromic compound was saturated or nearly saturated (i.e., the regions where the measured absorbance did not increase or did not increase significantly over time) for each sample by averaging absorbance at each time interval in this region. The average absorbance values in a predetermined range of wavelengths corresponding $\lambda_{max-vis}$+/−5 nm were extracted for the 0° and 90° polarizations, and the absorption ratio for each wavelength in this range was calculated by dividing the larger average absorbance by the small average absorbance. For each wavelength extracted, 5 to 100 data points were averaged. The average absorption ratio for the photochromic compound was then calculated by averaging these individual absorption ratios.

Change in optical density ($\Delta$OD) from the bleached state to the darkened state was determined by establishing the initial transmittance, opening the shutter from the xenon lamp to provide ultraviolet radiation to change the test lens from the bleached state to an activated (i.e., darkened) state. Data was collected at selected intervals of time, measuring the transmittance in the activated state, and calculating the change in optical density according to the formula: $\Delta$OD=log(% Tb/% Ta), where % Tb is the percent transmittance in the bleached state, % Ta is the percent transmittance in the activated state and the logarithm is to the base 10. Measurements were made at a weighted wavelength range corresponding to CIE Y, described in CIE Technical Report, Colorimetry, CIE 15:2004, 3$^{rd}$ Edition, published by the Commission Internationale De L'Eclairage, Vienna, Austria, which publication is incorporated herein by reference.

The fade half life (T½) is the time interval in seconds for the $\Delta$OD of the activated form of the photochromic compounds in the test samples to reach one half the $\Delta$OD measured after fifteen minutes, or after saturation or near-saturation was achieved, at room temperature after removal of the source of activating light, e.g., by closing the shutter. The $\Delta$OD, fade half life and absorption ratio were all determined prior to fatigue testing.

An Atlas Ci4000 Weather-Ometer® was used for conducting the simulated solar radiation accelerated weathering, i.e., fatigue. The samples were exposed for a 1 hour dark cycle and then a 65 hour light cycle using a boro/boro silicate filtered Xenon arc lamp with an output of 0.25 Watts per square meter at 340 nm. The temperature in the Atlas Ci4000 Weather-Ometer® was maintained at 45° C. and the relative humidity was controlled at 70% humidity. The temperature of the black panel which has a thermometer connected to it and is representative of the test samples was maintained at 55° C.

After the samples underwent this UV exposure fatigue cycle, they were preconditioned and measured on the optical bench to obtain the final $\Delta$OD$_{final}$ under the same conditions as described for the initial testing. The percent fatigue was determined by measuring the difference between the change in optical density ($\Delta$OD) of the test sample before and after accelerated weathering according to the formula: % Fatigue= ($\Delta$OD$_{init}$−$\Delta$OD$_{final}$)/$\Delta$OD$_{init}$×100.

Also determined was the delta b* value. The delta b* value was the measured difference in the bleach state b* value as determined by the measured b*$_{init}$ on the Hunter UltraScan Pro unit prior to exposure in the Atlas Ci4000 Weather-Ometer® minus the measured b*$_{final}$ value on the bleached state of the lens after this UV exposure fatigue cycle of 65 hours. The delta b* represents the amount of yellowing of the lens that occurs during fatigue.

The test results reported in Table 3 were for square substrates prepared as described in Part 5 having a photoalignment layer coated with LCCF-1 containing Examples 1, 2 or 3. A Grey-1 Control was also included. The test results reported in Table 4 were for finished single vision lenses prepared as described in Part 5 having a photoalignment layer coated with LCCF-2 containing Examples 4, 5 or 6. A Grey-2 Control was also included. The test results reported in Table 5 were for finished single vision lenses prepared as described in Part 5 having a photoalignment layer coated with LCCF-3 containing Examples 7, 8, 9, 10 or 11 and a TLCF layer. A Grey-3 Control was also included. All test results were an arithmetic average of duplicate tests.

TABLE 3

Results for Examples 1, 2 and 3 Compared to Grey-1 Control

| Example # | ΔOD | AR | T½ (sec) | % Fatigue (65 hr) | Δb* (65 hr) |
|---|---|---|---|---|---|
| Grey-1 Control | 0.53 | 5.0 | 176 | 36 | 8.6 |
| 1 | 0.54 | 4.4 | 161 | 26 | 6.1 |
| 2 | 0.52 | 4.8 | 168 | 22 | 6.2 |
| 3 | 0.52 | 4.6 | 162 | 22 | 5.7 |

TABLE 4

Results for Examples 4, 5 and 6 Compared to Grey-2 Control

| Example # | ΔOD | AR | T½ (sec) | % Fat (65 hr) | Δb* (65 hr) |
|---|---|---|---|---|---|
| Grey-2 Control | 0.60 | 4.2 | 133 | 25 | 9.2 |
| 4 | 0.62 | 4.0 | 114 | 17 | 7.2 |
| 5 | 0.63 | 4.0 | 135 | 24 | 8.7 |
| 6 | 0.62 | 4.0 | 129 | 24 | 9.0 |

TABLE 5

Results for Examples 7-11 Compared to Grey-3 Control

| Example # | ΔOD | AR | T½ (sec) | % Fat (65 hr) | Δb* (65 hr) |
|---|---|---|---|---|---|
| Grey-3 Control | 0.56 | 3.7 | 164 | 26 | 6.7 |
| 7 | 0.55 | 4.1 | 167 | 15 | 4.3 |
| 8 | 0.55 | 4.1 | 151 | 17 | 4.5 |
| 9 | 0.56 | 4.0 | 153 | 16 | 4.9 |
| 10 | 0.54 | 4.0 | 141 | 18 | 4.8 |
| 11 | 0.56 | 3.5 | 143 | 15 | 4.3 |

The present invention has been described with reference to specific details of particular embodiments thereof. It is not intended that such details be regarded as limitations upon the scope of the invention except insofar as and to the extent that they are included in the accompanying claims.

We claim:

1. A compound represented by the following Formula I,

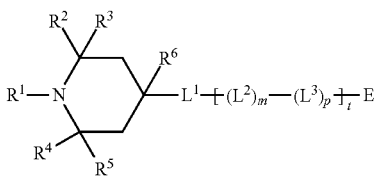

wherein $R^1$ is selected from hydrogen, hydrocarbyl and substituted hydrocarbyl each optionally interrupted with at least one of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from hydrogen, hydrocarbyl and substituted hydrocarbyl, and combinations of two or more thereof, $R^2$, $R^3$, $R^4$ and $R^5$ are each independently selected from hydrogen, hydrocarbyl and substituted hydrocarbyl, $R^6$ is selected from hydrogen, OH, hydrocarbyl and substituted hydrocarbyl each optionally interrupted with at least one of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from hydrogen, hydrocarbyl and substituted hydrocarbyl, and combinations of two or more thereof, $L^1$ is a divalent linking group selected from a bond, or one of the following Formulas IIa, IIb, IIc, IId, or IIe,

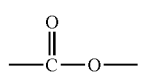

IIa

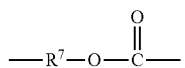

IIb wherein $R^7$ is selected from divalent hydrocarbyl and divalent substituted hydrocarbyl,

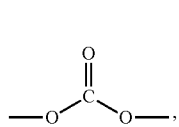

IIc

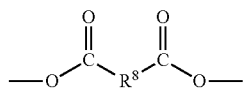

IId wherein $R^8$ is selected from divalent hydrocarbyl and divalent substituted hydrocarbyl, and

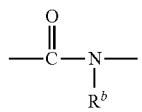

IIe wherein $R^b$ is selected from hydrogen, hydrocarbyl and substituted hydrocarbyl, t is 1 to 4, m is, independently for each t, from 0 to 4, $L^2$ is, independently for each m, selected from divalent linear or branched $C_1$-$C_{25}$ alkyl and divalent linear or branched $C_2$-$C_{25}$ alkenyl, in each case optionally interrupted with at least one of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from hydrogen, hydrocarbyl and substituted hydrocarbyl, and combinations of two or more thereof, p is, independently for each t, from 0 to 4, provided the sum of m and p is at least 1 for each t, $L^3$ is, independently for each p, represented by the following Formula VI,

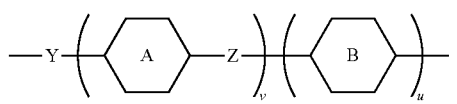

VI

Y is, independently for each p, a divalent linking group selected from a bond, —O—, and —S—, v and u are each independently, for each p, selected from 0 to 5, provided that the sum of v and u is at least 1 for each p that is greater than zero, Z is, independently for each v, a divalent linking group selected from a bond, —O—, —S—, —C(O)—, —C(O)O—, —OC(O)O—, —S(O)—, —SO$_2$—, —N(R$^9$)—, —N(R$^9$)—C(O)—O—, —C(O)—N(R$^9$)—, and —Si(R$^9$)(R$^{10}$)— wherein R$^9$ and R$^{10}$ are each independently selected from hydrogen, hydrocarbyl and substituted hydrocarbyl, the divalent rings,

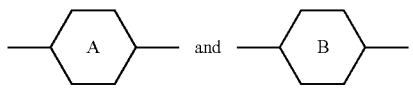

are each independently selected, for each v and each u, from phenylen-1,4-diyl, or substituted phenylen-1,4-diyl, or cyclohexan-1,4-diyl, or substituted cyclohexan-1,4-diyl, or pyrimidin-2,5-diyl, or substituted pyrimidin-2,5-diyl, or pyridine-2,5-diyl, or substituted pyridine-2,5-diyl, or naphthalene-2,6-diyl, or substituted naphthalene-2,6-diyl, or 1,2,3,4-tetrahydronaphthalene-2,6-diyl, or 1,2,3,4-tetrahydronaphthalene-2,6-diyl in which the aromatic ring is substituted, or decahydronaphthalene-2,6-diyl, or indane-2,5(6)-diyl, or fluorene-2,-7-diyl, or phenanthrene-2,7-diyl, or 9,10-dihydrophenanthrene-2,7-diyl, or (1,3,4)thiadiazol-2,5-diyl, or (1,3)thiazol-2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl, and E is selected from hydrogen, hydrocarbyl and substituted hydrocarbyl each optionally interrupted with at least one of —O—, —S—, —C(O)—, —C(O)O—, —OC(O)O—, —S(O)—, —SO$_2$—, —N(R$^9$)—, and —Si(R$^9$)(R$^{10}$)— wherein R$^9$ and R$^{10}$ are each independently selected from hydrogen, hydrocarbyl and substituted hydrocarbyl, and combinations of two or more thereof, provided that a direct L$^1$-L$^2$ link between L$^1$ and L$^2$ is free of two heteroatoms linked together, a direct L$^1$-L$^3$ link between L$^1$ and L$^3$ is free of two heteroatoms linked together, and each direct L$^2$-L$^3$ link between each directly linked L$^2$ and L$^3$ is free of two heteroatoms linked together.

2. The compound of claim 1, wherein,

R$^1$ is selected from hydrogen, linear or branched C$_1$-C$_{25}$ alkyl, linear or branched C$_2$-C$_{25}$ alkenyl, each optionally interrupted with a group selected from cyclohexylen-1,4-diyl, —O—, —C(O)—, and —Si(CH$_3$)$_2$—, and each optionally having at least one hydrogen replaced with F, R$^2$, R$^3$, R$^4$ and R$^5$ are each independently selected from linear or branched C$_1$-C$_{10}$ alkyl, R$^6$ is selected from hydrogen, linear or branched C$_1$-C$_{25}$ alkyl, linear or branched C$_2$-C$_{25}$ alkenyl, each optionally interrupted with a group selected from cyclohexylen-1,4-diyl, —O—, —C(O)—, and —Si(CH$_3$)$_2$—, and each optionally having at least one hydrogen replaced with F, R$^7$ and R$^8$ of L$^1$ are each independently selected from divalent linear or branched C$_1$-C$_{25}$ alkyl, divalent linear or branched C$_2$-C$_{25}$ alkenyl, divalent C$_3$-C$_{12}$ cycloalkyl, divalent C$_3$-C$_{12}$ heterocycloalkyl, divalent aryl, and divalent heteroaryl, m is at least 1 for at least one t, L$^2$ is, independently for each m, selected from divalent linear or branched C$_1$-C$_{25}$ alkyl optionally interrupted with at least one of —O—, —C(O)O—, and —OC(O)O—, p is at least 1 for at least one t, Z is, independently for each v, selected from a bond, —O— and —C(O)O—, the divalent rings,

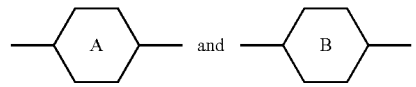

are each independently selected, for each v and each u, from phenylen-1,4-diyl, or substituted phenylen-1,4-diyl, or cyclohexan-1,4-diyl, or substituted cyclohexan-1,4-diyl, provided that at least one divalent ring-A and at least one divalent ring-B are each independently selected from phenylen-1,4-diyl, or substituted phenylen-1,4-diyl, and E is selected from hydrogen, linear or branched C$_1$-C$_{25}$ alkyl, linear or branched C$_2$-C$_{25}$ alkenyl, each optionally interrupted with at least one of —O— and —C(O)O—.

3. The compound of claim 2, wherein,

R$^1$ is selected from hydrogen, or linear or branched C$_1$-C$_8$ alkyl,

R$^2$, R$^3$, R$^4$ and R$^5$ are each independently selected from linear or branched C$_1$-C$_6$ alkyl, R$^6$ is selected from hydrogen, and linear or branched C$_1$-C$_8$ alkyl, L$^1$ is selected from a bond or the divalent linking group represented by Formula IId, wherein R$^8$ is divalent linear or branched C$_1$-C$_6$ alkyl, L$^2$ is, independently for each m, selected from divalent linear or branched C$_1$-C$_{10}$ alkyl optionally interrupted with at least one of —O—, —C(O)O—, and —OC(O)O—, and E is selected from hydrogen and linear or branched C$_1$-C$_{10}$ alkyl optionally interrupted with at least one of —O— and —C(O)O—.

4. The compound of claim 1, wherein L$^1$ is the divalent linking group represented by Formula IId, wherein R$^8$ is divalent linear or branched C$_1$-C$_6$ alkyl.

5. The compound of claim 1, wherein E is substituted with at least one group represented by the following formula,

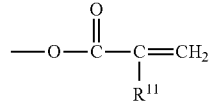

in which R$^{11}$ is selected from hydrogen and linear or branched C$_1$-C$_8$ alkyl.

6. The compound of claim 1, wherein at least one of:

(i) E is substituted with at least one group selected from, a group represented by the following Formula G,

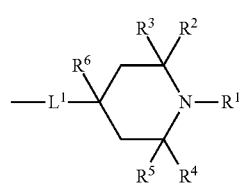

Formula G wherein $R^1$, $R^2$, $R^3$, $R^4$, $R^5$, $R^6$, and $L^1$ are each independently as defined in claim 1, provided that each direct E-$L^1$ link between E and $L^1$ of Formula G is free of two heteroatoms linked together, and a group represented by the following Formula H, Formula H

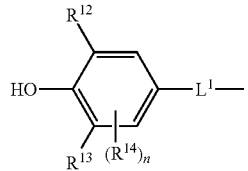

wherein $L^1$ is independently as defined in claim 1, $R^{12}$ and $R^{13}$ are each independently selected from hydrogen, hydrocarbyl, and substituted hydrocarbyl, provided that at least one of $R^{12}$ and $R^{13}$ is selected from hydrocarbyl or substituted hydrocarbyl, and n is 0, 1 or 2, and $R^{14}$ is independently for each n selected from hydrocarbyl and substituted hydrocarbyl, provided that each direct E-$L^1$ link between E and $L^1$ of Formula H is free of two heteroatoms linked together; and (ii) at least one $L^3$ is substituted with at least one group selected from, a group represented by the following Formula G, Formula G

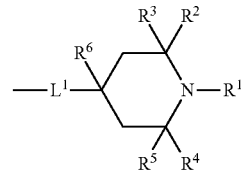

wherein $R^1$, $R^2$, $R^3$, $R^4$, $R^5$, $R^6$, and $L^1$ are each independently as defined in claim 1, provided that each direct $L^3$-$L^1$ link between $L^3$ and $L^1$ of Formula G is free of two heteroatoms linked together, and a group represented by the following Formula H, Formula H

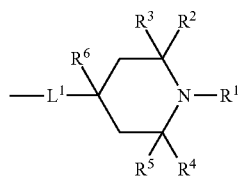

wherein $L^1$ is independently as defined in claim 1, $R^{12}$ and $R^{13}$ are each independently selected from hydrogen, hydrocarbyl, and substituted hydrocarbyl, provided that at least one of $R^{12}$ and $R^{13}$ is selected from hydrocarbyl or substituted hydrocarbyl, and n is 0, 1 or 2, and $R^{14}$ is independently for each n selected from hydrocarbyl and substituted hydrocarbyl, provided that each direct $L^3$-$L^1$ link between $L^3$ and $L^1$ Formula H is free of two heteroatoms linked together.

7. The compound of claim 1, wherein E is substituted with at least one group represented by the following Formula H, Formula H

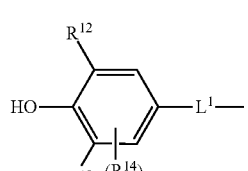

wherein $L^1$ is independently as defined in claim 1, $R^{12}$ and $R^{13}$ are each independently selected from hydrogen, hydrocarbyl, and substituted hydrocarbyl, provided that at least one of $R^{12}$ and $R^{13}$ is selected from hydrocarbyl or substituted hydrocarbyl, and n is 0, 1 or 2, and $R^{14}$ is independently for each n selected from hydrocarbyl and substituted hydrocarbyl, provided that each direct E-$L^1$ link between E and $L^1$ of Formula H is free of two heteroatoms linked together, and at least one $L^3$ is substituted with a group represented by the following Formula G, Formula G

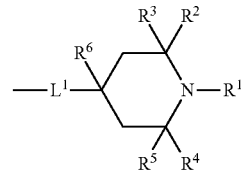

wherein $R^1$, $R^2$, $R^3$, $R^4$, $R^5$, $R^6$, and $L^1$ are each independently as defined in claim 1, provided that each direct $L^3$-$L^1$ link between $L^3$ and $L^1$ of Formula G is free of two heteroatoms linked together.

8. The compound of claim 3, wherein each $L^3$ is independently selected from the following formulas, Formula VII(A)

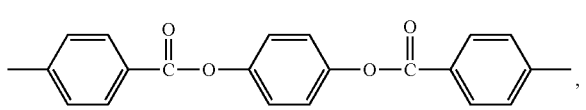

Formula VII(B)

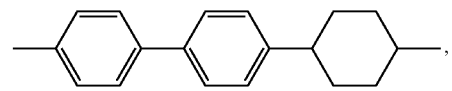

Formula VII(C)

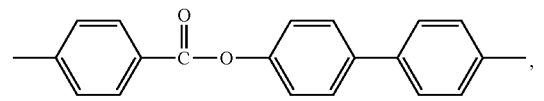

Formula VII(D)

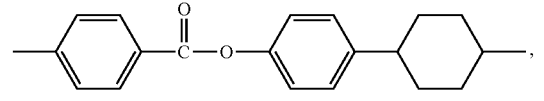

Formula VII(E)

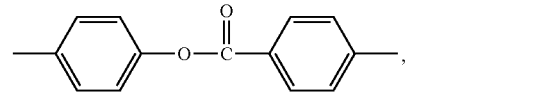

Formula VII(F)

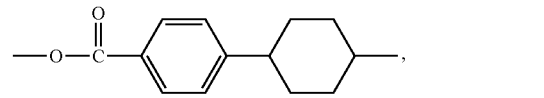

Formula VII(G)

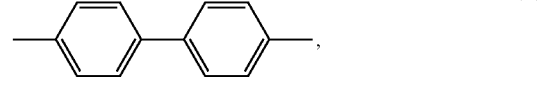

Formula VII(H)
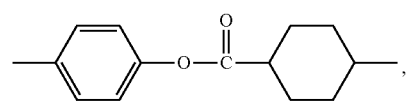
Formula VII(I)
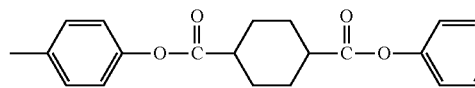 , and
Formula VII(J)
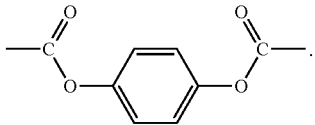 .
9. The compound of claim 1, wherein said compound is selected from at least one compound represented by the following Formulas VIII(A) through VIII(N),
Formula VIII(A)
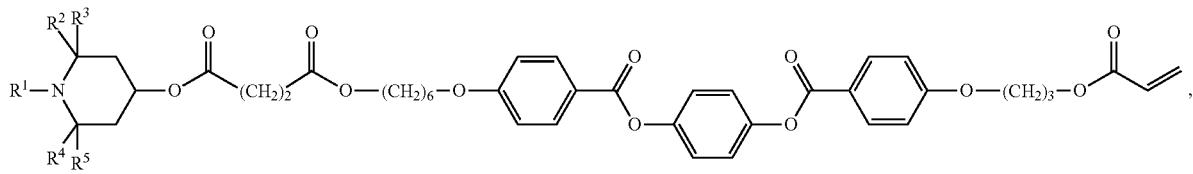 ,
Formula VIII(B)
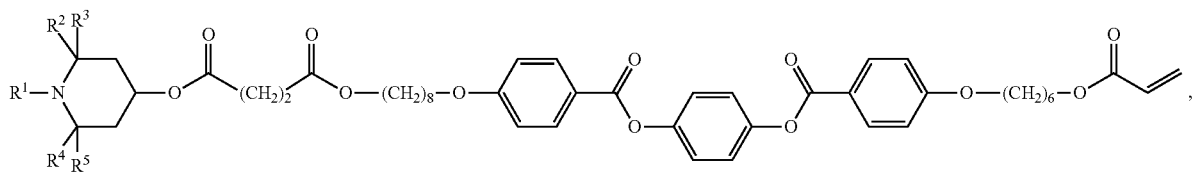 ,
Formula VIII(C)
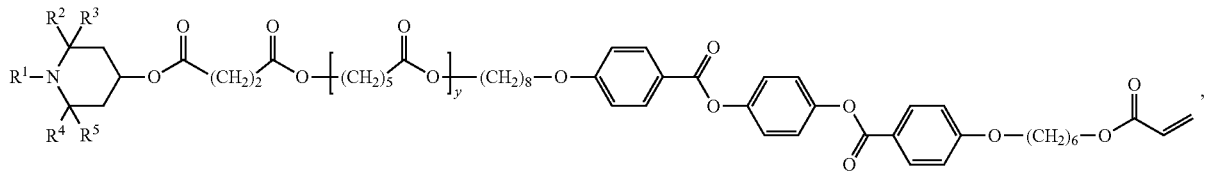 ,
wherein y is from 1 to 25,
Formula VIII(D)
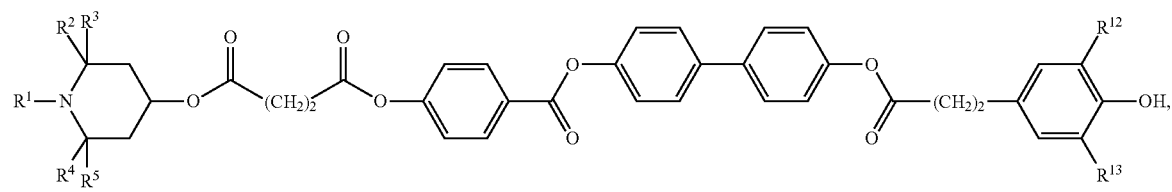 ,
Formula VIII(E)
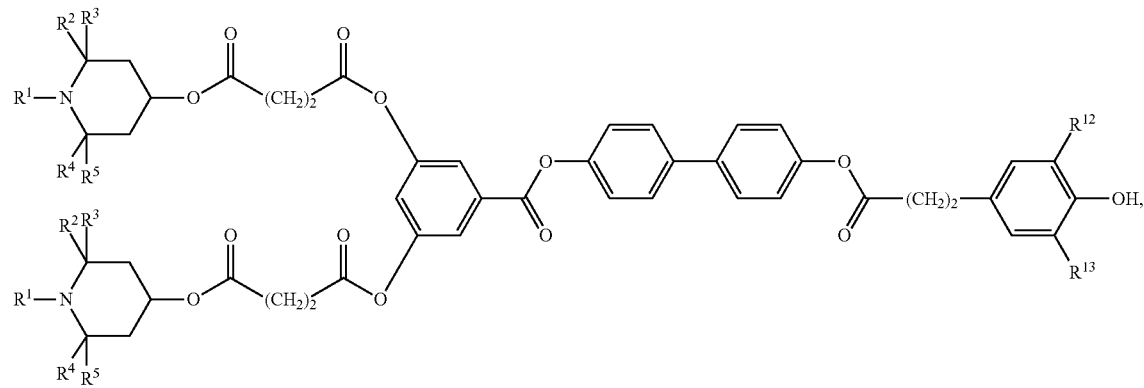 ,

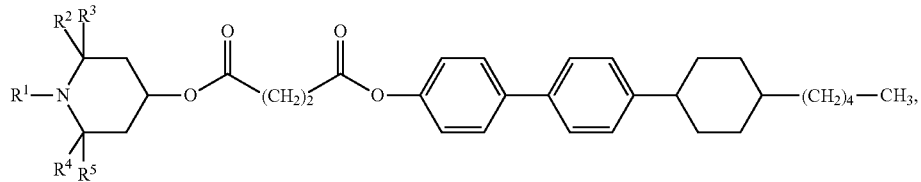
Formula VIII(F)
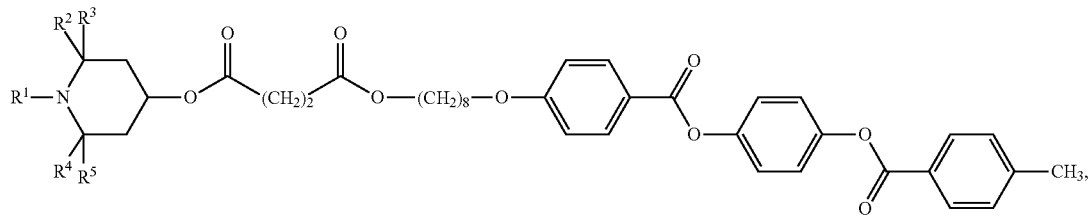
Formula VIII(G)
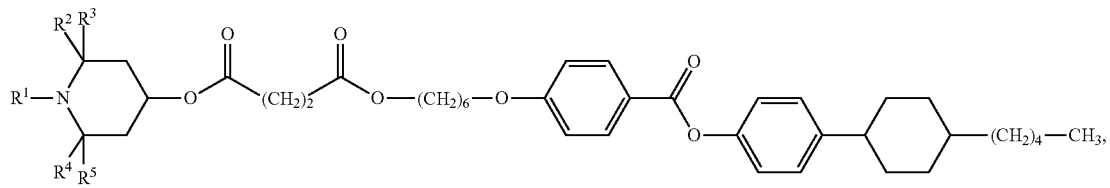
Formula VIII(H)
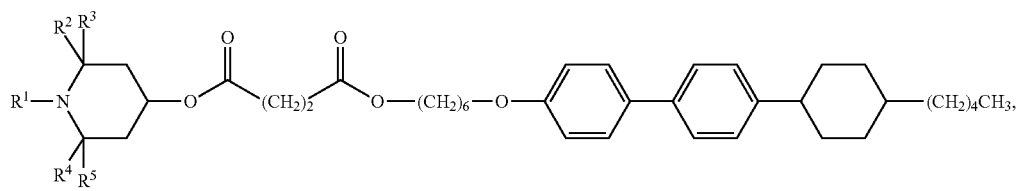
Formula VIII(I)
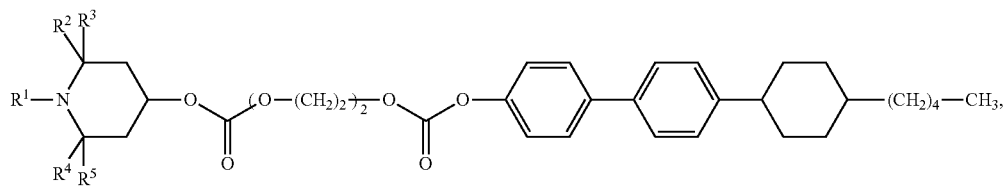
Formula VIII(J)
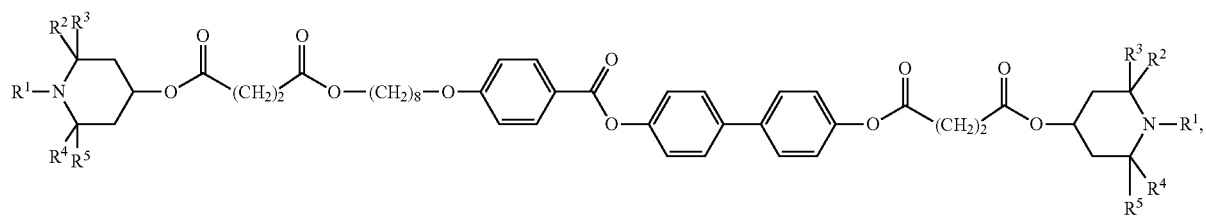
Formula VIII(K)
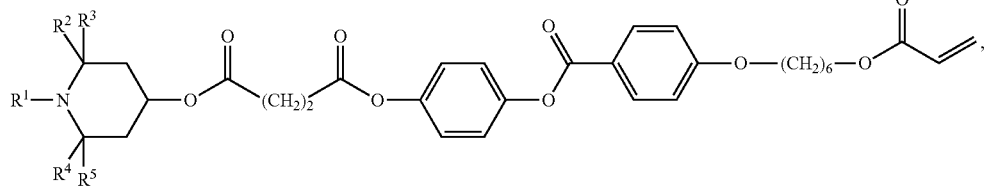
Formula VIII(L)

-continued

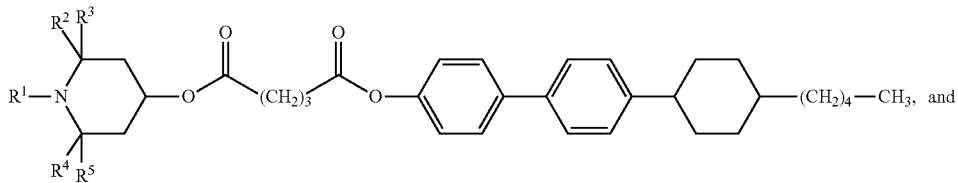

Formula VIII(M)

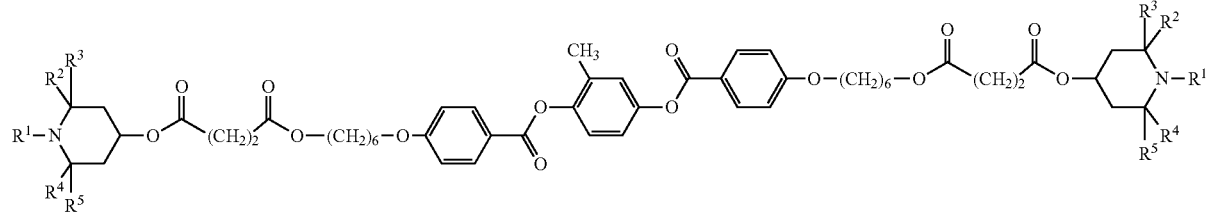

Formula VIII(N)

wherein $R^1$, $R^2$, $R^3$, $R^4$, and $R^5$ are in each case methyl, and $R^{12}$ and $R^{13}$ are in each case tertiary butyl.

10. The compound of claim 1, wherein the compound is a mesogenic compound.

11. A liquid crystal composition comprising the compound of claim 1.

12. The liquid crystal composition of claim 11, further comprising at least one of a photochromic compound, a dichroic compound, and a photochromic-dichroic compound.

13. The liquid crystal composition of claim 12, wherein said photochromic compound or said photochromic-dichroic compound is selected from indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, non-thermally reversible photochromic compounds, and mixtures thereof.

14. An article of manufacture comprising the compound of claim 1.

15. The article of manufacture of claim 14, wherein said article of manufacture is an optical element comprising:
a substrate; and
a layer on at least a portion of a surface of said substrate, wherein said layer comprises the compound of claim 1.

16. The optical element of claim 15, wherein said layer is at least partially aligned by exposing at least a portion of said layer to at least one of a magnetic field, an electric field, linearly polarized radiation, and shear force.

17. The optical element of claim 15, wherein said layer comprises a liquid crystal phase having at least one of a nematic phase, a smectic phase, or a chiral nematic phase.

18. The optical element of claim 15, wherein said optical element is selected from an ophthalmic element, a display element, a window, a mirror, and a liquid crystal cell element.

19. The ophthalmic element of claim 18, wherein said ophthalmic element is selected from a corrective lens, a non-corrective lens, a contact lens, an intra-ocular lens, a magnifying lens, a protective lens, and a visor.

20. The article of manufacture of claim 14, wherein said article of manufacture is a liquid crystal cell comprising:
a first substrate having a first surface;
a second substrate having a second surface, said first surface of said first substrate and said second surface of said second substrate being in spaced opposition from each other, and together defining a space there-between; and
a liquid crystal composition residing within at least a portion of said space, said liquid crystal composition comprising the compound of claim 1.

21. A method of forming an ophthalmic element comprising:
forming a liquid crystal composition comprising the compound of claim 1;
applying said liquid crystal composition to at least a portion of a substrate;
at least partially aligning at least a portion of the liquid crystal composition applied to said substrate, thereby forming an at least partially aligned liquid crystal composition; and
curing, at least partially, the aligned liquid crystal composition.

* * * * *